US008980845B2

(12) United States Patent
Sallam et al.

(10) Patent No.: US 8,980,845 B2
(45) Date of Patent: Mar. 17, 2015

(54) BIOTECHNOLOGICAL PRODUCTION OF CYANOPHYCIN DIPEPTIDES

(75) Inventors: Ahmed Sallam, Münster (DE); Alexander Steinbüchel, Altenberge (DE)

(73) Assignee: Westfälische Wilhelms-Universität Münster, Münster (DE)

( * ) Notice: Subject to any disclaimer, the term of this patent is extended or adjusted under 35 U.S.C. 154(b) by 954 days.

(21) Appl. No.: 12/995,762

(22) PCT Filed: Jun. 15, 2009

(86) PCT No.: PCT/EP2009/057382
§ 371 (c)(1),
(2), (4) Date: Jan. 24, 2011

(87) PCT Pub. No.: WO2009/150252
PCT Pub. Date: Dec. 17, 2009

(65) Prior Publication Data
US 2011/0118177 A1    May 19, 2011

(30) Foreign Application Priority Data

Jun. 13, 2008  (EP) .................... 08158205

(51) Int. Cl.
| C07K 5/06 | (2006.01) |
| C07K 4/04 | (2006.01) |
| C12P 13/04 | (2006.01) |
| A61K 38/05 | (2006.01) |
| C12P 21/06 | (2006.01) |
| A23K 1/16 | (2006.01) |
| A23L 1/305 | (2006.01) |
| A61K 38/16 | (2006.01) |
| C12N 9/52 | (2006.01) |

(52) U.S. Cl.
CPC ............. *C12P 21/06* (2013.01); *A23K 1/1631* (2013.01); *A23L 1/3053* (2013.01); *A61K 38/05* (2013.01); *A61K 38/164* (2013.01); *C12N 9/52* (2013.01)
USPC ........ 514/21.91; 435/106; 530/343; 530/332; 530/333

(58) Field of Classification Search
None
See application file for complete search history.

(56) References Cited

U.S. PATENT DOCUMENTS

| 4,225,579 A | 9/1980 | Kleinberg et al. |
| 7,091,001 B2 | 8/2006 | Radha et al. |
| 2004/0137081 A1 | 7/2004 | Rohdewald |

FOREIGN PATENT DOCUMENTS

WO    95/30744    11/1995

OTHER PUBLICATIONS

Obst, 2002, JBC, 277, 25096-25105.*
Obst, 2002, JBC, 277, 25059-25105.*
Aboulmagd, E. et al., "Molecular characterization of the cyanophycin synthetase from *Synechocystis* sp. strain PCC6308", Arch. Microbiol. 174, pg. 297-306 (2000).
Aboulmagd, E. et al., Heterologous Expression of Cyanophycin Synthetase and Cyanophycin Synthesis in the Industrial Relevant Bacteria *Corynebacterium glutamicum* and *Ralstonia eutropha* and in *Pseudomonas putida* Biomacromolecules 2, p. 1338-1342 (2001).
Adibi S A., "The Oligopeptide Transporter (Pept-1) in Human Intestine: Biology and Function", Gastroenterology 113, p. 332-340 (1997).
Adibi, S. A., " Intestinal Transport of Dipeptides in Man: Relative Importance of Hydrolysis and Intact Absorption", J. Clin. Invest. 50, p. 2266-2275 (1971).
Ahmed, I. And Khan, M. A., "Dietary arginine requirement of fingerling Indian major carp, *Cirrhinus mrigala* (Hamilton)", Aquacult. Nutr. 10, p. 217-225 (2004).
Allen M M et al, "Inclusions: Cyanophycin", Methods Enzymol 167, p. 207-213 (1988).
Allen, M. M. et al., "Cyanophycin Granule Polypeptide Formation and Degradation in the Cyanobacterium Aphanocapsa 6308", J. Bacteriol. 141, p. 687-693 (1980).
Allen, M. M. et al., "Protein Degradation and Synthesis of Cyanophycin Granule Polypeptide in *Aphanocapsa* sp.", J. Bacteriol. 154, p. 1480-1484 (1983).
Appleton, J., "Arginine: Clinical Potential of a Semi-Essential Amino Acid", Altern. Med. Rev. 7, p. 512-522 (2002).
Arino, X. et al., "Effect of sulfur starvation on the morphology and ultrastructure of the cyanobacterium Gloeothece sp. PCC 6909", Arch. Microbiol. 163, p. 447-453 (1995).
Baek, S. H. et al., "*Brevibacillus ginsengisoli* sp. nov., a denitrifying bacterium isolated from soil of a ginseng field", Int. J. Syst. Evol. Microbiol. 56, p. 2665-2669 (2006).
Barbul, A. et al., "Arginine enhances wound healing and lymphocyte immune responses in humans", Surgery 108, pg. Abstract Only (1990).
Barrett, G. C. and Elmore D. T. "Amino Acids and Peptides", Cambridge University Press, Cambridge, UK (1998).
Basson, R. et al., "Report of the International Consensus Development Conference on Female Sexual Dysfunction: Definitions and Classifications", J. Urol. 163, p. 888-893 (2000).
Battaglia, C. et al., "Adjuvant Larginine treatment for invitro fertilization in poor responder patients", Hum. Reprod. 14, p. 1690 (1999).
Bednarz, B. et al., "Effects of oral L-arginine supplementation on exercise-induced QT dispersion and exercise tolerance in stable angina pectoris", Int. J. Cardiol. 75, p. 205-210 (2000).
Besset, A. et al., "Increase in sleep related GH and Prl secretion after chronic arginine aspartate administration in man", Acta Endocrinol. (Copenh). Jan. 1982;99(1):18-23.Abstract Only.
Boger, R. H. et al., "Restoring Vascular Nitric Oxide Formation by L-Arginine Improves the Symptoms of Intermittent Claudication in Patients With Peripheral Arterial Occlusive Disease", J. Am. Coll. Cardiol. 32, p. 1336-1344 (1998).

(Continued)

*Primary Examiner* — Satyanarayana R Gudibande
(74) *Attorney, Agent, or Firm* — Norris McLaughlin & Marcus, P.A.

(57) ABSTRACT

The present invention relates to a process for the enzymatic production of a dipeptide composition from a cyanophycin (CGP) or CGP-like polymer preparation by degrading the polymer preparation with an CGPase, a CGPase particularly adapted for said process, and the use of cyanophycin (CGP) or CGP-like polymers or fragments thereof, notably a dipeptide composition obtained by the process as defined above, as pharmaceutical composition, medicament, or as food or feed substitute.

12 Claims, 9 Drawing Sheets

(56) References Cited

OTHER PUBLICATIONS

Figure 1A:
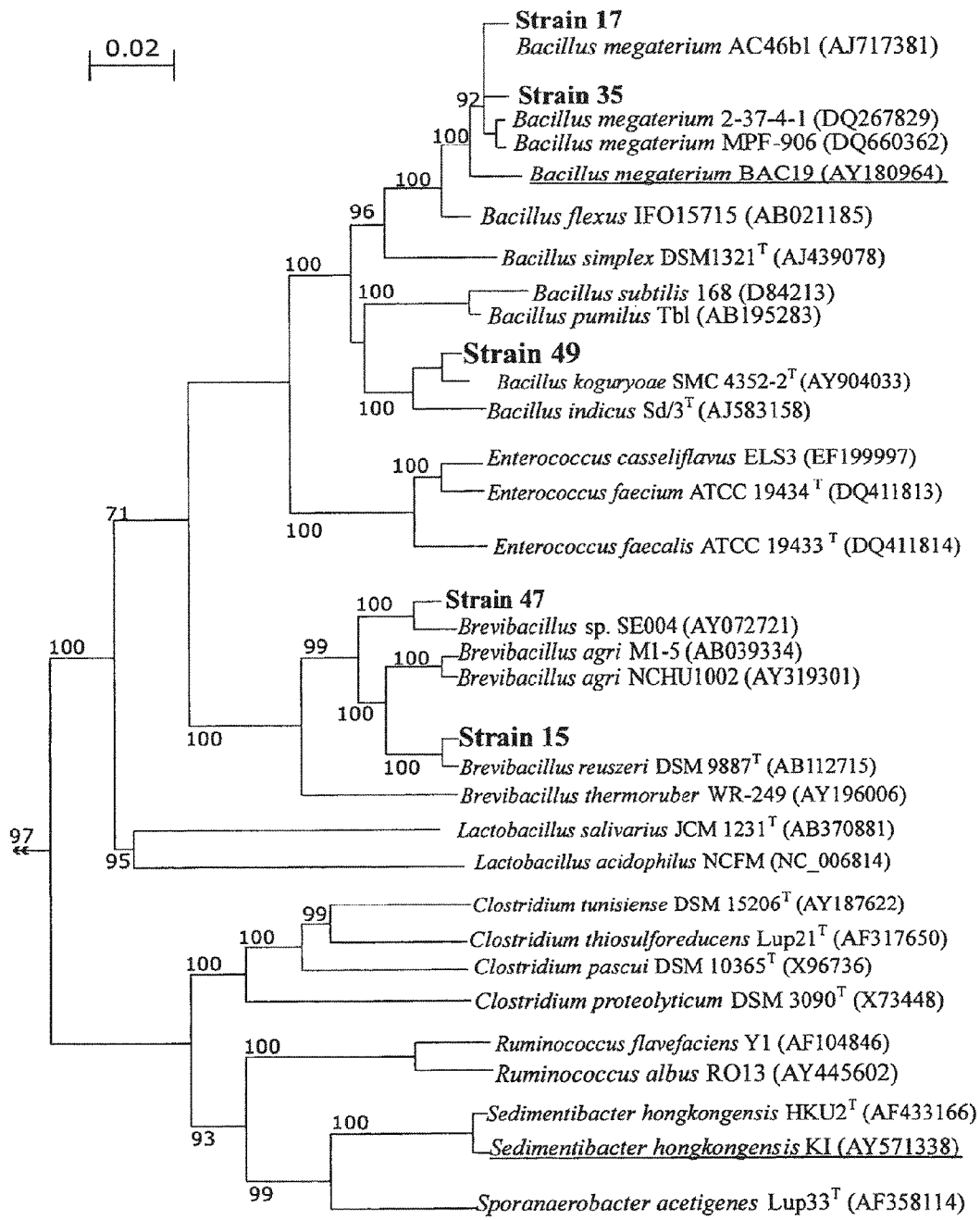

Borodina, I. et al., "Genome-scale analysis of *Streptomyces coelicolor* A3(2) metabolism", Genome Res. 15, p. 820-829 (2005).
Borzi, A., "Cyanophycin an Ideal Bacterial Nitrogen Storage Material with Unique Chemical Properties", Malpighia (1887).
Boutard, V. et al., "Transforming Growth Factor-β Stimulates Arginase Activity in Macrophages", J. Immunol 155, p. 2077-2084 (1995).
Brzozowski, T., "Role of L-Arginine, a substrate for nitric oxide-synthase, in gastroprotection and ulcer healing", J. Gastroenterol. 32, p. 442-452 (1997).
Burtscher, M. et al., "The Prolonged Intake of L-Arginine-L-Aspartate Reduces Blood Lactate Accumulation and Oxygen Consumption During Submaximal Exercise", J. Sports. Sci. Med. 4, 314-322 (2005).
Carr, N. G. "Nitrogen reserves and dynamic reservoirs in cyanobacteria", p. 13-21. In L. J. Rogers and J. R. Gallon 1988.
Christianson, D. W., "Arginase: Structure, Mechanism, and Physiological Role in Male and Female Sexual Arousal", Acc. Chem. Res. 38, p. 191-201 (2005).
Cochrane, V. W., "Physiology of Actinomycetesl,2," Annu. Rev. Microbiol. 15, p. 1-26 (1961).
Cohen, J. S., "Is the sildenafil product information adequate to facilitate informed therapeutic decisions?" Ann. Pharmacother. 35, p. 337-342 (2001).
Cynober, L. A., "Metabolic and therapeutic aspects of amino acids in clinical nutrition", 2nd ed. CRC Press LLC, Boca Raton, (1995).
Daly, et al., "Immune and Metabolic Effects of Arginine in the Surgical Patient" J. M. et al., Ann. Surg. 208, p. 512-523 (1988).
Daniel, H. et al., "From Bacteria to Man: Archaic Proton-Dependent Peptide Transporters at Work" Physiology 21, p. 93-102 (2006).
De-Aloysio, D. et al., Abstract (PubMed) and Cross reference (Appleton, J., Altera. Med. Rev. 7:512-522 (2002)) for the cited reference: De-Aloysio, D. et al., Acta Eur. Fertil. 13:133-167 (1982) For detailed experimental description, please refer to the cross reference, section: "Infertility, Male" (p. 517). Acta Eur. Fertil. 13133-167 (1982).
Dean, W. and Pryor, K., "Growth hormone amino acids as GH secretagogues—a review of the literature", Vit. Res. News (1979). www.vrp.com/amino-acids/growth-hormone-amino-acids-as gh-... (Nov. 24, 2011).
Dock, D. B. et al., "Probiotics enhance the recovery of gut atrophy in experimental malnutrition", Biocell 28, p. 143-150 (2004).
Dufresne, A. et al., "Preparation and Characterization of a Poly(β-hydroxyoctanoate) Latex Produced by *Pseudomonas oleovorans*", Macromolecules 31, 6426-6433 (1998).
Duruy, A. Cross reference (Schmid, et al. 1980 (with partial English translation)) for the references: "Influence on Arginine-aspartate on performance and metabolic changes during a long term activity", Vie. Med. Int. 9:1589 (1965).
Elbahloul, Y. et al., Protamylasse, a Residual Compound of Industrial Starch Production, Provides a Suitable Medium for Large-Scale Cyanophycin Production, Appl. Environ. Microbiol. 71, p. 7759-7767 (2005).
Elsair, "Effects of arginine, administered orally, on the endogenous secretion of the STH-somatomedin complex in young human volunteers", C R Seances Soc Biol Fil. 1985;179(5):608-14, Abstract Only.
Erickson, N. A. et al., "A rapid and sensitive method for the analysis of cyanophycin" p. 5-9 (2001).
Evoy, D. et al. "Immunonutrition: The Role of Arginine", 14, p. 611-617 (1998).
Facchinetti, F. et al., "L-Arginine infusion reduces preterm uterine contractions",J. Perinat. Med. 24, p. 283-285 (1996).
Faix, et al., "In Vitro Transfer of L-Alanine, L-Histidine and Carnosine Across The Rumen Epithelium of Sheep", Acta Vet. Brno. 70, p. 243-246 (2001).
Ferrini, M. et al., "Aging-Related Expression of Inducible Nitric Oxide Synthase and Markers of Tissue Damage in the Rat Penis1", Biol. Reprod. 64 p. 974-982 (2001).

Firoozi, F. et al., "In vivo and in vitro response of corpus cavernosum to phosphodiesterase-5 inhibition in the hypercholesterolaemic rabbit", Br. J. Urol. Int. 96, p. 164-168 (2005).
Flodin, N. W., "The metabolic roles, pharmacology, and toxicology of lysine", J. Am. Coll. Nutr. 16, 7-21 (1997). Abstract Only.
Frey, K. M. et al., "Technical-Scale Production of Cyanophycin with Recombinant Strains of *Escherichia coli*" Appl. Environ. Microbiol. 68 pg. 3377-3384 (2002).
Fuser, G. et al., "Analysis of Genome Sequences for Genes of Cyanophycin Metabolism: Identifying Putative Cyanophycin Metabolizing Prokaryotesa", Macromol. Biosci. 7, p. 278-296 (2007).
Gerritse, G. et al., "Development of a Lipase Fermentation Process That Uses a Recombinant *Pseudomonas alcaligenes* Strain", Appl. Environ. Microbiol. 64, p. 2644-2651 (1998).
Giugliano, D. et al., "L-Arginine for testing endothelium-dependent vascular functions in health and disease", Am. J. Physiol. 273, p. E606-E612 (1997).
Glaser, P. et al., "Identification and Isolation of a Gene Required for Nitrate Assimilation and Anaerobic Growth of *Bacillus subtilis*", J. Bacteriol. 177, p. 1112-1115 (1995).
Griffith, R. S. et al., "A multicentered study of lysine therapy in Herpes simplex infection", Dermatologica 156(5) p. 257-267 (1978). Abstract.
Gupta, M. et al., "Enzyme Activities Related to Cyanophycin Metabolism in Heterocysts and Vegetative Cells of *Anabaena* spp.", J. Gen. Microbiol. 125, p. 17-23 (1981).
Herndon, D. N. et al., "Effects of Recombinant Human Growth Hormone on Donor-site Healing in Severely Burned Children", Ann. Surg. 212 p. 424-429 (1990).
Heukeshoven, J. et al., "Simplified method for silver staining of proteins in polyacrylamide gels and the mechanism of silver staining*", Electrophoresis 6, p. 103-112 (1985).
Holt, L. E. Jr. Cross reference (Appleton, J., Altern. Med. Rev. 7:512-522 (2002)) for the cited reference: Holt, L. E. Jr. and Albanese, A. A., Trans. Assoc. Am. Physicians 58:143-156 (1944)) for detailed description, please refer to the cross reference, section: "Infertility, Male" (p. 517). "Arginine: Clinical Potential of a Semi-Essential Amino Acid", Trans. Assoc. Am. Physicians 58, p. 143-156 (1944).
Holter, J. B. et al., "Protein-Fat Bypass Supplement for Lactating Dairy Cows1"J. Dairy. Sci. 76, p. 1342-1352 (1993).
Hrabak, A. et al. "The inhibitory effect of nitrite, a stable product of nitric oxide (NO) formation, on arginase", FEBS Lett. 390, p. 203-206 (1996).
Hurson, M. et al., "Metabolic Effects of Arginine in a Healthy Elderly Population", J. Parenter. Enteral Nutr. 19, p. 227-230 (1995).
Ingram, L. O. et al., "Effects of Selected Inhibitors on Growth and Cell Division in Agmenellum", Arch. Microbiol. 81, p. 1-12 (1972).
Isidori, A. et al., "A study of growth hormone release in man after oral administration of amino acids", Curr. Med. Res. Opin. 7, p. 475-481 (1981).
Ito, T. Y. et al., "A Double-Blind Placebo-Controlled Study of ArginMax, a Nutritional Supplement for Enhancement of Female Sexual Function", J. Sex Marital Ther. 27, p. 541-549 (2001)).
Joentgen, W. et al., Cross reference (Witte, M. B. and Barbul. A., Wound Rep. Reg. 11:419-423 (2003)) for the cited reference: Jorgensen, P. H and Andreassen, T. T., Acta Chir. Scand. 154:623-626 (1988) for detailed description, please refer to the cross reference, section: "Endocrine/secretagogue effects" (p. 422). "Polyaspartic Acids", Chemical Analysis, 4, p. 175-181, (2003).
Jorgensen, P. H, et al. "Arginine physiology and its implication for wound healing", Acta Chir. Scand. 154, p. 623-626 (1988).
Kernohan, A. F. B. et al., "An oral yohimbine/L-arginine combination (NMI 861) for the treatment of male erectile dysfunction: a pharmacokinetic, pharmacodynamic and interaction study with intravenous nitroglycerine in healthy male subjects", Br. J. Clin. Pharmacol. 59, p. 85-93 (2004).
Kihlberg R A The Microbe As a Source of Food', Rev Microbio. 26, p. 427-466 (1972).
Kircheis G. et al. "Therapeutic Efficacy of L-Ornithine-L-Aspartate Infusions in Patients With Cirrhosis and Hepatic Encephalopathy: Results of a Placebo-Controlled, Double-Blind Study", Hepatology 25, p. 1351-1360 (1997).

(56) References Cited

OTHER PUBLICATIONS

Krehenbrink, M. et al., "Evaluation of non-cyanobacterial genome sequences for occurrence of genes encoding proteins homologous to cyanophycin synthetase and cloning of an active cyanophycin synthetase from *Acinetobacter* sp. strain DSM 587", Arch. Microbiol. 177, p. 371-380 (2002).
Krug, A., Diplom thesis, Institut fur Molekulare Mikrobiologie and Biotechnologie, Westfalische Wilhelms-Universitat, (2001).
Lacks, S. A. et al., "Renaturation of Enzymes after Polyacrylamide Gel Electrophoresiisn the Presence of Sodium Dodecyl Sulfate*", J. Biol. Chem. 225_7467-7473 (1980).
Laemmli, U. K., "Cleavage of Structural Proteins During the Assembly of the Head of Bacteriophage T4", Nature 227, p. 680-685 (1970).
Laidlaw, S. A. "Newer concepts of the indispensable amino acids1-3", Am. J. Clin. Nutr. 46, p. 593-605 (1987).
Lamm, S. et al., "Prelox® for Improvement of Erectile Function: A Review", Eur. Bull. Drug Res. 11, p. 29-37 (2003).
Leopold, C. S. et al., "In Vivo Pharmacokinetic Study for the Assessment of Poly(L-Aspartic Acid) as a Drug Carrier for Colon-Specific Drug Delivery", J. Pharmacokinet. Biopharm. 4, p. 397-406 (1995).
Li, F. et al., "An antimetastatic study of Arg-Asp (RD) on salivary adenoid cystic carcinoma in vivo", Chin. J. Stomatol. (2001). Abstract Only.
Li, F. et al., Antimetastatic effects of arginine-aspartate on salivary adenoid cystic carcinoma in vitro', Chin. J. Stomatol. (2002). Abstract Only.
Li, H. et al., "Pattern of cyanophycin accumulation in nitrogen-fixing and non-nitrogen-fixing cyanobacteria", Arch. Microbiol. 176, p. 9-18 (2001).
Liotenberg, S. et al., "Effect of the nitrogen source on phycobiliprotein synthesis and cell reserves in a chromatically adapting filamentous cyanobacterium", Microbiology 142, p. 611-622 (1996).
Lu J. et al. "Ingestion, assimilation and utilization of raw Spirulina by larval tilapia *Oreochromis niloticus* during larval development", Aquaculture, 254, p. 686-692 (2004).
Luiking, Y. C. et al., "Effects of long-term oral L-arginine on esophageal motility and gallbladder dynamics in healthy humans", Am. J. Physiol. 274, p. G984-G991 (1998).
Macintyre, J. G., "Growth Harmone and Athletes", Sports Med. (1987). Abstract Only.
Mackerras, A. H. et al., "Transient accumulations of cyanophycin in *Anabaena cylindrica* and Synechocystis 6308", J. Gen. Microbiol. 136, p. 2057-2065 (1990).
Marcell, T. J. et al., "Oral Arginine Does Not Stimulate Basal or Augment Exercise-Induced GH Secretion in Either Young or Old Adults", J. Gerontol. 54, p. 395-399 (1999).
Modolell M. et al. "Reciprocal regulation of the nitric oxide synthase/arginase balance in mouse bone marrow-derived macrophages by TH1 and TH2 cytokines", Eur. J. Immunol 25, p. 1101-1104 (1995).
Mooibroek, H. et al., "Assessment of technological options and economical feasibility for cyanophycin biopolymer and high-value amino acid production", Appl. Microbiol. Biotechnol. 77, p. 257-267 (2007).
Moore, et al., "*Pseudomonas* Nonmedical", Prokaryotes, Chapter 3.3.21, p. 646-703, May 1999.
Mroueh, A., "Effect of Arginine on Oligospermia*", Fertil. Steril. 2, p. 217-219 (Mar. 1970).
Murrell G. A. C. et al. "Modulation of tendon healing by nitric oxide", Inflamm. Res. 46, p. 19-27 (1997).
Musicki, B. et al., "Phosphorylated Endothelial Nitric Oxide Synthase Mediates Vascular Endothelial Growth Factor-Induced Penile ErectionI", Biol. Reprod. 70, p. 282-289 (2004).
Nakaki T. and Kato R, "Beneficial Circulatory Effect of L-Arginine", Jpn J. Pharmacol. 66, p. 167-171 (1994).
Narasimha D. L. R. et al. Nutritional Quality of the Blue-Green Alga *Spirulina platensis* Geitler', J. Sci. Food Agric. 33, p. 456-460 (1982).

Nesterenko, M. V. et al., "A simple modification of Blum's silver stain method allows for 30 minute detection of proteins in polyacrylamide gels", J. Biochem. Biophys. Methods 3, p. 239-242 (1994).
Obst, M. et al., "Degradation of Cyanophycin by Sedimentibacter hongkongensis Strain KI and *Citrobacter amalonaticus* Strain G Isolated from an Anaerobic Bacterial Consortium", Appl. Environ. Microbiol. 71, p. 3642-3652 (2005).
Obst, M. et al., "Isolation and Characterization of Gram-Positive Cyanophycin-Degrading acterias Kinetic Studies on Cyanophycin Depolymerase Activity in Aerobic Bacteria", Biomacromolecules 5, p. 153-161 (2004).
Obst, M. et al., "Isolation of Cyanophycin-degrading Bacteria, Cloning and Characterization of an Extracellular Cyanophycinase Gene (cphE) from *Pseudomonas anguilliseptica* Strain BI", J. Biol. Chem. 277, pp. 25096-25105 (2002).
Obst, M. et al., "Cyanophycin an Ideal Bacterial Nitrogen Storage Material with Unique Chemical Properties", pp. 167-194. In J. M. Shively (ed.), Inclusions in Prokaryotes, vol. 1. Springer-Verlag, Berlin, 2006.
Ohtsuka Y. and Nakaya "Effect of Oral Administration of L-Arginine on Senile Dementia", J. Am. J. Med. 108 p. 439 (2000).
Oppermann-Sanio F. B. et al., "Occurrence, functions and biosynthesis of polyamides in microorganisms and biotechnological production", Naturwissenchaften, 89, p. 11-22 (2002).
Penny R. et al., "Sequential Arginine and Insulin Tolerance Tests on the Same Day", J. Clin. Endocrinol. 29, pp. 1499-1501 (1969).
Pezza, V. et al., "Study of Supplemental Oral l-Arginine in Hypertensives Treated With Enalapril + Hydrochlorothiazide", Am. J. Hypertens, 11, pp. 1267-1270 (1998).
Rao R. N. et al. "Cosmid Shuttle Vectors for Cloning and Analysis of *Streptomyces* DNA", Methods Enzymol. 153, pp. 166-198 (1987).
Richter R. et al. "Cyanophycinase, a peptidase degrading the cyanobacterial reserve material multi-L-arginyl-polyL-aspartic acid (cyanophycin)", Eur. J. Biochem. 263, pp. 163-169 (1999).
Roberts J. M. "Objective Evidence of Endothelial Dysfunction in Preeclampsia"Am. J. Kidney Dis. 33, pp. 992-997 (1999).
Rohdewald, P., "A Review of the French Maritime Pine Bark Extract (Pycnogenol®), a Herbal Medication With Diverse Clinical Pharmacology", Int. J. Clin. Pharmacol. Ther. 40, pp. 158-168 (2002).
Ross, E., "The Nutritional Value of Dehydrated, Blue-Green Algae", Poult-Sci. 69, pp. 794-800 (1990).
Roweton, S. et al., "Poly(aspartic Acid): Synthesis, Biodegradation, and Current Applications", J. Environ. Polym. Degrad. 5, pp. 175-181 (1997).
Sallam and Steinbüchel, "Cyanophycin-degrading bacteria in digestive tracts of mammals, birds and fish and consequences for possible applications of cyanophycin and its dipeptides in nutrition and therapy", J. App. Microbiol. pp. 474-484, (2009).
Sallam, A., and A. Steinbüchel. "Biotechnological Process for Production of β-Dipeptides from Cyanophycin on a Technical Scale and Its Optimization", Applied and Environmental Microbiology, pp. 29-38, Jan. 2009.
Sallam, A., and A. Steinbüchel. "Anaerobic and Aerobic Degradation of Cyanophycin by the Denitrifying Bacterium *Pseudomonas alcaligenes* Strain DIP1 and Role of Three Other Coisolates in a Mixed Bacterial Consortium", Applied and Environmental Microbiology, pp. 3434-3443, Jun. 2008.
Sallam, A., and A. Steinbüchel, "Dipeptides in nutrition and therapy: cyanophycin-derived dipeptides as natural alternatives and their biotechnological production", Appl. and Microbiol Biotechnol. pp. 815-828, (2010).
Sallam, A., and A. Steinbüchel, "Clostridium Sulfidigenes sp. nov., a mesophilic, proteolytic, thiosulfate- and sulfur-reducing bacterium isolated from pond sediment", Int'l. Journal of Systematic and Evol. Micro. pp. 1-7 (2009).
Sambrook, J. et al., Molecular cloning a Laboratory Manual, 2nd ed. Cold Spring Harbor, N.Y., Appendix A: Bacterial Media, Antibiotics, and Bacterial Strains, 1989.
Sanchez, A. et al., "Cholesterolemic Effects of the The Lysine/Arginine Ratio in Rabbits After Initial Early Growth" Nutr. 38, pp. 229-238 (1998).
Sanders P. W. "Salt-Sensitive Hypertension: Lessons From Animal Models", Am. J. Kidney Dis. 28, pp. 775-782 (1996).

(56) References Cited

OTHER PUBLICATIONS

Schacter, A. et al., "Treatment of Oligospermia with the Amino Acid Arginine", Int. J. Gynaecol. Obstet. 11, pp. 206-209 (1973).
Schacter, A. et al., "Treatment of Oligospermia With the Amino Acid Arginine", J. Urol. 110, pp. 311-313 (1973).
Schaffer, M. R. et al., "Inhibition of Nitric Oxide Synthesis in Wounds: Pharmacology and Effect on Accumulation of Collagen in Wounds in Mice", Eur. J. Surg. 165, pp. 262-267 (1999).
Schellen, et al., "Arginine aspartate in the treatment of oligozoospermia", Dermatol. Monatsschr. 164, pp. 578-580 (1978). (English Summary).
Schmid, P. et al., "Influence on Arginine-aspartate on performance and metabolic changes during a long-term activity", Leistungssport, 10, pp. 486-495 (1980) and translation.
Schwamborn, M., "Chemical synthesis of polyaspartates: a biodegradable alternative to currently used polfcarboxylate homo- and copolymers", Polym. Degrad. Stab. 59, pp. 39-45 (1998).
Seifter, E. et al., "Arginine: An Essential Amino Acid for Injured Rats", Surgery 84, pp. 224-230 (1978).
Sellier, J., (Cross reference (Burtscher, M. et al., J. Sports. Sci. Med. 4:314-322 (2005)) for the cited reference: Sellier, J., Rev. Med. Toulouse 5:879 (1979)) for detailed description, please refer to the introduction of the cross reference (p. 314). "The Prolonged Intake of L-Arginine-L-Aspartate Reduces Blood Lactate Accumulation and Oxygen Consumption During Submaximal Exercise", Rev. Med. Toulouse 5879 (1979).
Sherman, D. M. et al., "Heterocyst Development and Localization of Cyanophycin in $N_2$-Fixing Cultures of Anabaena Sp. PCC 7120 (Cynaobacteria)", J. Phycol. 36, pp. 932-941 (2000).
Shi, H. P. et al., "Supplemental dietary arginine enhances wound healing in normal but not inducible nitric oxide synthase knockout mice", Surgery 128, pp. 374-378 (2000).
Simon, R. D., "Inclusion bodies in the cyanobacteria cyanophycin, polyphosphate, polyhedral bodies", Dept. of Biology, pp. 199-225 (1987).
Simon, R. D. et al., "Determination of the Structure of the Novel Polypeptide Containing Aspartic Acid and Arginine Which Is Found in Cyanobacteria" Biochim. Biophys. Acta, 420, pp. 165-176 (1976).
Simon, R. D., Arch. "The Effect of Chloramphenicol on the Production of Cyanophycin Granule Polypeptide in the Blue-Green Alga *Anabaena cylindrical*", Microbiol. 92, pp. 115-122 (1973a).
Simon, R. D., "The Biosynthesis of Multi-L-Arginyl-Poly(L-Aspartic Acid) in the Filamentous Cyanobacterium *Anabaena cylindrica*", Biochim. Biophys. Acta., 422, pp. 407-418 (1976).
Simon, R. D., "Measurement of the Cyanophycin Granule Polypeptide Contained in the Blue-Green Alga *Anabaena* cylindrical", J. Bacteriol. 114, pp. 1213-1216 (1973b).
Smith, S. D. et al., "Improvement in Interstitial Cystitis Symptom Scores During Treatment With Oral L-Arginine", J. Urol. 158, pp. 703-708 (1997).
Stallmeyer, B. et al., "The Function of Nitric Oxide in Wound Repair. Inhibition of Inducible Nitric Oxide-Synthase Severely Impairs Wound Reepithelialization", J. Invest. Dermatol. 113, pp. 1090-1098 (1999).
Stanislavov, R. and Nikolova, V., "Prelox® for Improvement of Erectile Function: A Review", Int. J. Impot. Res. 14 (4, pp. )565 (2002).
Stanislavov, R. and Nikolova, V., J. Sex Marit. Ther., 29, pp. 207-213 (2003). Cross reference (Lamm, S. et al., "Treatment of Erectile Dysfunction with Pycnogenol and L-arginine", Eur. Bull. Drug Res. 11:29-37 (2003)) for the cited reference: Stanislavov, R. and Nikolova, V., Int. J. Impot. Res. 14(4):565 (2002); for detailed description, please refer to the cross reference, section: "Long Term Prelox®; Regimen" (p. 33).
Stephan et al., "Interrelation between Cyanophycin Synthesis, 1-Arginine Catabolism and Photosynthesis in the Cyanobacterium Synechocystis Sp. Strain PCC 6803", Z. Naturforsch. 55c, (2000).
Suminski, R. R. et al., "Acute Effect of Amino Acid Ingestion and Resistance Exercise on Plasma Growth Hormone Concentration in Young Men", Int. J. Sport Nutr. 7, pp. 48-60 (1997).
Swanson, B., "A Pilot Study of the Safety and Efficacy of Supplemental Arginine to Enhance Immune Function in Persons With HIV/AIDS", Nutrition 18, pp. 688-690 (2002).
Tanimura, "Studies on Arginine in Human Semen: Part I. The Arginine Contents of Normal and Sterile Human Semen", J., Bull. Osaka Med. School 13, pp. 76-83 (1967).
Vodovotz, Y. et al., "Mechanisms of Suppression of Macrophage Nitric Oxide Release by Transforming Growth Factor β", J. Exp. Med. 178, pp. 605-613 (1993).
Voet, D. and Voet, J. G., Biochemistry. 3th ed. John Wiley and Sons Inc., New York (2004)).
Voss, I. et al., "Application of a KDPG-aldolase gene-dependent addiction system for enhanced production of cyanophycin in *Ralstonia eutropha* strain H16", Metabol. Eng. 8, pp. 66-78 (2006).
Wascher, T. C. et al., "Effects of low-dose L-Arginine on insulin-mediated vasodilatation and insulin sensitivity", Eur. J. Clin. Invest. 27, pp. 690-695 (1997).
Watanabe, G. H. et al., "Effects of oral administration of L-arginine on renal function in patients with heart failure"; J. Hypertens. 18, 229-234 (2000).
Weber, K. et al., "SDS-PAGE to Determine the Molecular Weight of Proteins: the Work of Klaus Weber and Mary Osborn : The Reliability of Molecular Weight Determinations by Dodecyl Sulfate-Polyacrylamide Gel Electrophoresis" (Weber, K., and Osborn, M. (1969) J. Biol. Chem. 244, 4406-4412); J. Biol. Chem. vol. 281, No. 24, Issue of Jun. 16, p. e19, 2006.
Wei, L. H. et al., "Elevated arginase I expression in rat aortic smooth muscle cells increases cell proliferation"; Proc. Natl. Acad. Sci. USA 98, 9260-9264 (2001).
Wingard, L. L. et al., "Cyanophycin Production in a Phycoerythrin-Containing Marine Synechococcus Strain of Unusual Phylogenetic Affinity"; Appl. Environ. Microbiol. vol. 68, 1772-1777 (2002).
Witte, M. B. and Barbul A., "Arginine physiology and its implication for wound healing" Wound Rep. Reg. p. 11, 419-423 (2003).
Yamasaki, K. et al., "Reversal of Impaired Wound Repair in iNOS-deficient Mice by Topical Adenoviral-mediated iNOS Gene Transfer"; J. Clin. Invest. 101, p. 967-971 (1998).
Yokoyama, M. et al., "Characterization and Anticancer Activity of the Micelle-forming Polymeric Anticancer Drug Adriamycin-conjugated Poly(ethylene glycol)-Poly(aspartic acid) Block Copolymer" Cancer Res. 6, p. 1693-1700 (1990).
Yu, Y. M. et al., "Arginine and ornithine kinetics in severely burned patients: increased rate of arginine disposal"; Am. J. Physiol. Endocrinol. Metab. 280, p. E509-E517 (2001).
Ziegler, K. et al., "Molecular characterization of cyanophycin synthetase, the enzyme catalyzing the biosynthesis of the cyanobacterial reserve material multi-L-arginyl-poly-L-aspartate (cyanophycin)"; Eur. J. Biochem. 254, p. 154-159 (1998).
Ziegler, K. et al., "Cyanophycin Synthetase-Like Enzymes of Non-Cyanobacterial Eubacteria: Characterization of the Polymer Produced by a Recombinant Synthetase of *Desulfitobacterium hafniense*"; Naturforsch. 57c, p. 522-529 (2002).
Zinc, S. 2004. Diplom thesis, Institut fur Molekulare Mikrobiologie und Biotechnologie, Westfalische Wilhelms-Universitat (Translation p. 15).
Zorgniotti and Lizza 1994, (Cross reference Appleton, J.Altern. Med. Rev. 7:512-522 (2002)).
Geueke et al.; "Bacteria β-peptidyl aminopeptidases: on the hydrolytic degradation of β-peptides" Appl. Microbiol Biotechnol (2007) 74: pp. 1197-1204.
Grimble at al.; "The significance cif peptides in clinical nutrition"; Annu. Rev. Nutr. 14: pp. 419-447 (1994).
Law, et al.; "The structural basis of β-peptide-specificcleavage by the serine protease cyanophycinase"; J. Mol. Biol. (2009) 392, pp. 393-404.
Oppermann-Saino et al; "Cyanophycin"; Biopolymers, 7; pp. 83-106 (2003).

* cited by examiner

BIOTECHNOLOGICAL PRODUCTION OF CYANOPHYCIN DIPEPTIDES

This application is a 371 of PCT/EP2009/057382, filed Jun. 15, 2009, which claims foreign priority benefit under 35 U.S.C. §119 of the European Patent Application No. 08158205.8 filed Jun. 13, 2008.

The present invention relates to a process for the enzymatic production of a dipeptide composition from a cyanophycin (CGP) or CGP-like polymer preparation by degrading the polymer preparation with an CGPase, a CGPase particularly adapted for said process, and the use of cyanophycin (CGP) or CGP-like polymers or fragments thereof, notably a dipeptide composition obtained by the process as defined above, as pharmaceutical composition, medicament, or as food or feed substitute.

BACKGROUND OF THE INVENTION

Three different poly(amino acid)s are known to occur naturally: poly(ε-L-lysine) (ε-PL), poly(γ-glutamic acid) (γ-PGA), and cyanophycin (CGP). Poly(amino acid)s are present in many environments and fulfil different functions for the producing organisms (Obst, M. et al., Biomacromolecules 5:1166-1176 (2004)). For example, Cyanophycin (multi-L-arginyl-poly-[L-aspartic acid]), which is known also as Cyanophycin Granule Polypeptide (CGP), which was discovered in cyanobacteria more than 100 years ago (Borzi, A., Malpighia 1:28-74 (1887)) provides the organism with nitrogen, carbon and energy. It contains five nitrogen atoms in every building block and thereby represents an ideal intracellular nitrogen reserve (Mackerras, A. H. et al., J. Gen. Microbiol. 136:2057-2065 (1990)). The biocompatibility and complete biodegradability of poly(amino acid)s make them ideal candidates for many applications in human life in the fields of biomedicine, agriculture, agrochemistry, personal care, and pharmacy (Obst, M. et al., Biomacromolecules 5:1166-1176 (2004)).

Several species of cyanobacteria including the blue green algae *Spirulina* have been promoted as nutritional sources for humans and animals (Kihlberg, R., A. Rev. Microbiol. 26:427-466 (1972)). CGP itself was discovered in 1887 in cyanobacteria. Most genera of cyanobacteria harbor a functional cyanophycin synthetase gene (cphA) and synthesize CGP (Mackerras, A. H. et al., J. Gen. Microbiol. 136:2057-2065 (1990)). Genes coding for CphA were identified also in heterotrophic bacteria (Krehenbrink, M. et al., Arch. Microbiol. 177:371-380 (2002); Füser, G. et al., Macromol. Biosci. 7:278-296 (2007)). The branched polymer occurs in the cytoplasm as insoluble intracellular membraneless granules (Allen, M. M. et al., J. Bacteriol. 154:1480-1484 (1983)). It consists of equimolar amounts of arginine and aspartate arranged in the form of poly(aspartic acid) (PAA) backbone, with arginine moieties linked to the β-carboxyl group of each aspartic acid by its α-amino group (Simon, R. D. et al., Biochim. Biophys. Acta 420:165-176 (1976)). For large scale production, cyanobacterial cphA genes were heterologously cloned in *Escherichia coli, Corynebacterium glutamicum, Ralstonia eutropha* and *Pseudomonas putida*. CGP from recombinant bacteria contains a little lysine (Voss, I. et al., Metabol. Eng. 8:66-78 (2006)). CGP is widely spread in different natural habitats and is degraded by intracellular or by extracellular CGPases (CphB, CphE, respectively). Bacteria possessing CphE were found in various habitats; $CphE_{Pa}$ and $CphE_{Bm}$ were isolated and characterized from *P. anguliseptica* BI and *B. megaterium* BAC19, respectively (Obst, M. et al., J. Biol. Chem. 277:25096-25105 (2002); Obst, M. et al., Biomacromolecules 5:153-161 (2004)). CGP degradation occurs also in anaerobic habitats by strictly or facultative anaerobic bacteria such as *Sedimentibacter hongkongensis* KI or *P. alcaligenes* DIP1, respectively (Obst, M. et al., Appl. Environ. Microbiol. 71:3642-3652 (2005); Sallam, A. et al., Submitted for publication (2008)). All known CGPases produced water soluble β-dipeptides from CGP which are then transported into the cells to be further catabolized (Sallam, A. et al., Submitted for publication (2008)).

Protein digestion and transport is essential for life. In ruminants for instance, the major part of dietary protein is degraded by the rumen flora to amino acids and peptides. Amino acids are incorporated into microbial protein or passed to next parts of the digestive tract or absorbed directly across the rumen wall into the blood (Faix, Š. et al., Acta Vet. Brno. 70:243-246 (2001)). However, Tri- and dipeptides are more efficiently utilized than free amino acids, have greater nutritional value, are better absorbed [up to 185% greater than free amino acids (Adibi, S. A., J. Clin. Invest. 50:2266-2275 (1971)) and retain more nitrogen than intact protein contributing to enhance weight gain (Dock, D. B. et al., Biocell 28:143-150 (2004)). Absorption studies in patients with genetically impaired transport of certain amino acids showed normal absorption of these amino acids if administered as dipeptides. This indicated the presence of specialized and effective transport systems for dipeptides (Adibi, S. A., Gastroenterology 113:332-340 (1997)). Therefore, hydrolyzed protein diets are frequently applied as feed additives to recovery malnourished cases (Dock, D. B. et al., Biocell 28:143-150 (2004)).

The semi-essential amino acid arginine plays several pivotal roles in cellular physiology, and thus is applied in therapeutic regimens for many cardiovascular, genitourinary, gastrointestinal, or immune disorders (for review see (Appleton, J., Altern. Med. Rev. 7:512-522 (2002)). The essential amino acid lysine is known as food additive for human and animal, has antiviral activity against Herpes simplex virus, and improves calcium absorption in the small intestine, and hence acts against osteoporosis (Cynober, L. A., Metabolic and therapeutic aspects of amino acids in clinical nutrition. 2nd ed. CRC Press LLC, Boca Raton, USA (2003)). The non-essential amino acid aspartate serves among others as a precursor for L-arginine, for energy metabolism (Voet, D. et al., Biochemistry. 3th ed. John Wiley and Sons Inc., New York (2004)), and is used in drug delivery for cations or for other amino acids (Cynober, L. A., Metabolic and therapeutic aspects of amino acids in clinical nutrition. 2nd ed. CRC Press LLC, Boca Raton, USA (2003)). Because amino acids have higher bioavailability in the dipeptide form, their administration as dipeptides was clinically approved and are available in market products (Duruy, A. et al., Vie. Med. Int. 9:1589 (1965); Duruy, A., Med. Int. 1:203 (1966); Sellier, J., Rev. Med. Toulouse 5:879 (1979); De-Aloysio, D. et al., Acta Eur. Fertil. 13:133-167 (1982); Rohdewald, P., Int. J. Clin. Pharmacol. Ther. 40:158-168 (2002); Lamm, S. et al., Eur. Bull. Drug Res. 11:29-37 (2003)).

Until now, no direct applications are known for CGP itself. Previous studies on CGP were motivated by CGP as a potential source for a biodegradable PAA (Mooibroek, H. et al., Appl. Microbiol. Biotechnol. 77:257-267 (2007)). The latter has many potential applications (Obst, M. et al., Biomacromolecules 5:1166-1176 (2004)) as a component in dialysis membranes, artificial skin and orthopedic implants or as drug carrier. PAA could also substitute non-biodegradable polyacrylates for which many technical applications are described. This is the first study on the biodegradation of CGP by mammalian, avian and fish gut flora, and subsequently on the potential applications of CGP and the dipeptides thereof as nutritional and/or therapeutic additives.

Several samples of mammalian, avian and fish gut flora were investigated for cyanophycin degradation. All samples achieved complete anaerobic CGP degradation over incubation periods of 12-48 h at 37° C. CGP degrading bacteria were found in all samples and were highly concentrated in cecum flora from rabbit and sheep and digestive tract flora from carp fish. A total of 62 axenic cultures were isolated and degraded CGP aerobically, 46 thereof degraded CGP also anaerobically over incubation periods ranging from 24 h to 7 days. HPLC analysis revealed that all isolates degraded CGP to its constituting dipeptides. Eight strains were identified by 16S rDNA sequencing and were affiliated to the genera *Bacillus, Brevibacillus, Pseudomonas, Streptomyces* and *Micromonospora*. CGP could be found in three different *Spirulina platensis* commercial products which contained 0.06-0.15% (wt/wt) CGP. It was now found that CGP can be degraded extracellularly CGP degradation, as well as the first evidence on CGP biodegradability in the digestive tract, and subsequently, the potential application of CGP and its dipeptides in nutrition and therapy as highly bioavailable sources for arginine, lysine, aspartate and possibly other amino acids.

CGP accumulates in cyanobacteria during the transition from the exponential to the stationary growth phase (Mackerras, A. H. et al., J. Gen. Microbiol. 136:2057-2065 (1990); Sherman, D. M. et al., J. Phycol. 36:932-941 (2000)). Most genera of cyanobacteria harbor a functional cyanophycin synthetase gene (cphA) and synthesize CGP (Simon, R. D. 1987. Inclusion bodies in the cyanobacteria: cyanophycin, polyphosphate, polyhedral bodies, pp. 199-225. In P. Fay and C. van Baalen (ed.), The Cyanobacteria, Elsevier, Amsterdam, The Netherlands; Allen, M. M. et al., Methods Enzymol. 167:207-213 (1988); Mackerras, A. H. et al., J. Gen. Microbiol. 136:2057-2065 (1990); Liotenberg, S. et al., Microbiology 142:611-622 (1996); Wingard, L. L. et al., Appl. Environ. Microbiol. 68:1772-1777 (2002)). cphA genes were also identified in heterotrophic bacteria (Krehenbrink, M. et al., Arch. Microbiol. 177:371-380 (2002); Ziegler, K. et al., Naturforsch. 57c:522-529 (2002)). The polymer occurs in the cytoplasm as membraneless granules and is insoluble at neutral pH as well as in physiological ionic strength (Allen, M. M. et al., J. Bacteriol. 141:687-693 (1980)). CGP accumulates under limiting conditions including low temperature, low light intensity, phosphorous or sulfur limitation (Stephan et al., Z. Naturforsch. 55:927-942 (2000)). In cyanobacteria, the molecular mass of the polymer strands range from 25 to 100 kDa (Simon, R. D., Biochim. Biophys. Acta 422:407-418 (1976)), while those from recombinant strains exhibit a lower range (25 to 30 kDa) and polydispersity. Furthermore, it was found that the polymer from recombinant strains contained lysine as an additional amino acid constituent (Ziegler, K. et al., Eur. J. Biochem. 254:154-159 (1998); Aboulmagd, E. et al., Biomacromolecules 2:1338-1342 (2001)). CGP functions as a temporary nitrogen, energy and possibly carbon reserve (Li, H. et al., Arch. Microbiol. 176:9-18 (2001); Elbahloul, Y. et al., Appl. Environ. Microbiol. 71:7759-7767 (2005)). Because CGP contains five nitrogen atoms in every building block, it fulfills the criteria for the perfect intracellular nitrogen reserve (Simon, R. D. 1987. Inclusion bodies in the cyanobacteria: cyanophycin, polyphosphate, polyhedral bodies, pp. 199-225. In P. Fay and C. van Baalen (ed.), The Cyanobacteria, Elsevier, Amsterdam, The Netherlands).

The intracellular degradation of CGP is catalyzed by highly specific cyanophycinases (CphB) occurring in the cytoplasm and proceeds via an α-cleavage mechanism resulting in the formation of β-dipeptides (Richter, R. et al., Eur. J. Biochem. 263:163-169 (1999)). CGP represents a valuable substrate also for bacteria not capable of CGP accumulation (Obst, M. et al., Appl. Environ. Microbiol. 71:3642-3652 (2005); Sallam, A., and A. Steinbüchel. 2007a). *Clostridium sulfatireducens* sp. nov., a new mesophilic, proteolytic bacterium isolated from a pond sediment, able to reduce thiosulfate, sulfur and transiently sulfate), many of such bacteria were shown to possess extracellular cyanophycinases that degrades CGP to its utilizable dipeptides, which can be transported into the cell and further utilized (Sallam, A., and A. Steinbüchel. 2007b. Anaerobic and aerobic degradation of cyanophycin by the denitrifying bacterium *Pseudomonas alcaligenes* strain DIP1-Role of other three co-isolates in the mixed bacterial consortium. Submitted for publishing.) Several examples of these enzymes were isolated and characterized, such as $CphE_{Pa}$ from the Gram-negative bacterium *Pseudomonas anguilliseptica* strain BI. This extracellular enzyme exhibited, similar to CphB, an α-cleavage mechanism for CGP degradation (Obst, M. et al., J. Biol. Chem. 277:25096-25105 (2002)).

Also Gram-positive bacteria were found to excrete CGPases when the extracellular $CphE_{Bm}$ was isolated from *Bacillus megaterium* strain BAC19 (Obst, M. et al., Biomacromolecules 5:153-161 (2004)), both $CphE_{Pa}$ and $CphE_{Bm}$ were identified as serine-type hydrolases. Recent studies revealed that extracellular CGP degradation can be catalyzed also by CGPases from strict as well as facultative anaerobic bacteria, such as *Sedimentibacter hongkongensis* strain KI (Obst, M. et al., Appl. Environ. Microbiol. 71:3642-3652 (2005)) and *Pseudomonas alcaligenes* strain DIP1 (Sallam, A., and A. Steinbüchel. 2007b. Anaerobic and aerobic degradation of cyanophycin by the denitrifying bacterium *Pseudomonas alcaligenes* strain DIP1-Role of other three co-isolates in the mixed bacterial consortium. Submitted for publishing), respectively. All investigated CGPases yielded β-Asp-Arg dipeptides as cleavage products, however, (Asp-Arg)$_2$ tetrapeptides were additionally detected in case of $CphE_{Bm}$ (Obst, M. et al., Biomacromolecules 5:153-161 (2004)).

Until recently, no practical applications were known for CGP itself or for the dipeptides thereof. On contrast, economically important applications have been established for poly(aspartic acid) (PAA), which is a structural element (polymer backbone) of CGP, as a substitute for non-biodegradable polyacrylates (Schwamborn, M., Polym. Degrad. Stab. 59:39-45 (1998)). PAA can be also employed in many fields including paper, paint and oil industries (reviewed by Joentgen, W. et al. 2003. Polyaspartic acids. pp. 175-499. In: S. R. Fahnestock and A. Steinbüchel (ed.), Biopolymers, vol 7. Wiley, Weinheim). Biomedical applications have also been described for PAA (Leopold, C. S. et al., J. Pharmacokinet. Biopharm. 4:397-406 (1995); Yokoyama, M. et al., Cancer Res. 6:1693-1700 (1990)). Only recently, biomedical applications for CGP-dipeptides and possibly for CGP itself were revealed, these applications depend in first place on the astonishing wide spread of CGP-degrading bacteria in numerous investigated mammalian, avian, and fish flora, this indicated that CGP is probably degradable within the respective digestive tracts, On the other hand, the elevated bioavailability of amino acids if administrated in the dipeptide or tripeptide form is a well known theory and is effectively applied in several therapeutic fields. Thus, CGP and/or its β-dipeptides can be considered as potential natural food and/or therapeutic additives for the near future (Sallam, A., and A. Steinbüchel. 2007c. Potential of cyanophycin and its β-dipeptides as possible additives in therapy, food and feed industries).

The production and efficient isolation of CGP in semi-technical amounts was established only during the last few years. Several bacterial strains of *E. coli, Raistonia eutropha, Pseudomonas putida* and *Acinetobacter baylyi* strain ADP1 were applied, the later showed the maximum CGP yield of about 46% (wt/wt) (Obst, M. et al., pp. 167-194. In J. M. Shively (ed.), Inclusions in Prokaryotes, vol. 1. Springer-Verlag, Berlin, Heidelberg (2006)). However, the required substrates and cultivation conditions are also crucial factors for choosing the economically appropriate CGP-producer.

It was now found that pure CGP-dipeptides can be prepared in an economical large scale process which starts from CGP-containing biomass and ends with pure CGP-dipeptides. Because strain *P. alcaligenes* DIP1 could show high enzyme productivity on simple growth requirements. This strain was found ideal for such a technical process.

Cyanophycin contains five nitrogen atoms in every building block and therefore accomplishes exactly the criteria for a perfect dynamic intracellular nitrogen reserve (Simon, R. D. 1987. Inclusion bodies in the cyanobacteria: cyanophycin, polyphosphate, polyhedral bodies, pp. 199-225. In P. Fay and C. van Baalen (ed.), The Cyanobacteria, Elsevier, Amsterdam, The Netherlands); its amount fluctuates according to the needs of the cells (Carr, N. G. 1988. Nitrogen reserves and dynamic reservoirs in cyanobacteria, p. 13-21. In L. J. Rogers and J. R. Gallon (ed.), Biochemistry of the algae and cyanobacteria, Annual Proceedings of the Phytochemical Society of Europe, Clarendon, Oxford.). The polymer accumulates in cyanobacteria when the protein synthesis is diminished either naturally during the transition from the exponential to the stationary growth phase (Simon, R. D., Arch. Microbiol. 92:115-122 (1973a)) or by addition of inhibitors of protein biosynthesis (e.g. chloramphenicol) (Ingram, L. O. et al., Arch. Microbiol. 81:1-12 (1972); Simon, R. D., J. Bacteriol. 114:1213-1216 (1973b)) and the polymer disappears when balanced growth resumes (Mackerras, A. H. et al., J. Gen. Microbiol. 136:2057-2065 (1990)). CGP accumulation is also promoted by phosphorous limitation (Stephan et al., Z. Naturforsch. 55:927-942 (2000)), sulfure limitation (Ariño, X. et al., Arch. Microbiol. 163:447-453 (1995)), low temperature, low light intensity or a combination of these factors (Obst, M. et al., Biomacromolecules 5:1166-1176 (2004)).

Different methods were developed for determination and quantification of either purified CGP or its content in cells. Arginine content of CGP was quantified colorimetrically either in hydrolyzed or in unhydrolyzed polymer by the Sakagushi reagent (Simon, R. D., J. Bacteriol. 114:1213-1216 (1973b)). The amino acid constituents of the purified cyanophycin could be determined by HPLC (Aboulmagd, E. et al., Arch. Microbiol. 174:297-306 (2000)). For rapid and sensitive determination of cyanophycin, a method based on $^1$H nuclear magnetic resonance (NMR) was developed (Erickson, N. A. et al., Biochim. Biophys. Acta. 1536:5-9 (2001)).

CGP degradation (intra- or extracellular) leads mainly to the release of its utilizable dipeptides, these are then split intracellularly to their constituting amino acids to be engaged into cell metabolism. Intracellular degradation of cyanophycin is catalyzed by cyanophycinases (CphB). The first cyanophycinase was described in heterocysts and vegetative cells of *Anabaena cylindrica* by Gupta, M. et al., J. Gen. Microbiol. 125:17-23 (1981). The enzyme is a monomeric 29.4 kDa, serine-type, and a cyanophycin-specific exopeptidase, its main degradation product was aspartate-arginine dipeptides via an α-cleavage mechanism (Richter, R. et al., Eur. J. Biochem. 263:163-169 (1999)). In the last few years, aerobic and anaerobic bacteria able to degrade cyanophycin by extracellular cyanophycinases (CphE) were isolated (Obst, M. et al., J. Biol. Chem. 277:25096-25105 (2002)); Obst, M. et al., Biomacromolecules 5:153-161 (2004); Obst, M. et al., Appl. Environ. Microbiol. 71:3642-3652 (2005); Sallam, A., and A. Steinbüchel. 2007b. Anaerobic and aerobic degradation of cyanophycin by the denitrifying bacterium *Pseudomonas alcaligenes* strain DIP1-Role of other three co-isolates in the mixed bacterial consortium. Submitted for publishing). Similar to CphB, the previously characterized extracellular CGPases; $CphE_{Pa}$ and $CphE_{Bm}$, from *Pseudomonas anguilliseptica* strain B1 and *Bacillus megaterium* strain BAC19, respectively, were identified as serine-type, cyanophycin-specific enzymes and produced CGP-dipeptides as degradation products, however, (Asp-Arg)$_2$ tetrapeptides were additionally detected in case of $CphE_{Bm}$. Labeling studies of $CphE_{Pa}$ showed that the enzyme hydrolyses CGP at the carboxyl-terminus and successively releases β-Asp-Arg dipeptides from the degraded polymer chain end (for review see Obst, M. et al., Biomacromolecules 5:1166-1176 (2004)). Moreover, a third extracellular cyanophycinase ($CphE_{al}$) from *Pseudomonas alcaligenes* DIP1 was recently applied in crude form for the technical production of CGP-dipeptides (Sallam, A., and A. Steinbüchel. 2008b. Biotechnological process for the technical production of β-dipeptides from cyanophycin. Under preparation).

The production and efficient isolation of CGP in semi-technical amounts were established only during the last few years. Several bacterial strains of *Escherichia coli, Ralstonia eutropha, Pseudomonas putida* and *Acinetobacter baylyi* were successfully applied (Obst, M. et al., Biomacromolecules 5:1166-1176 (2004)). However, the biotechnological relevance of CGP was based theoretically on being a source for poly(aspartic acid) which has high potential for industrial applications [e.g. for water treatment; paper and leather industries, as dispersing agent (Roweton, S. et al., J. Environ. Polym. Degrad. 5:175-181 (1997); Mooibroek, H. et al., Appl. Microbiol. Biotechnol. 77:257-267 (2007)) or as biodegradable substitute for polyacrylate (Schwamborn, M., Polym. Degrad. Stab. 59:39-45 (1998)). PAA has also potential biomedical applications as a component in dialysis membranes, artificial skin, orthopaedic implants and as drug carrier (Leopold, C. S. et al., J. Pharmacokinet. Biopharm. 4:397-406 (1995)).

As set forth above, biomedical applications for CGP-dipeptides and possibly for CGP itself were revealed, this indicated that CGP is probably degradable within the mammalian and fish digestive tracts; this represented the polymer and the dipeptides thereof as potential natural food and/or therapeutic additives for the near future. Accordingly, a large scale process for the production of dipeptides from CGP using crude $CphE_{al}$ from *P. alcaligenes* strain DIP1 was recently constructed. This original process comprised three phases; Phase I: large scale extraction and purification of CGP, Phase II: large scale production of crude $CphE_{al}$ powder, Phase III: degradation of CGP to its dipeptides was set up as described hereinbefore. It was now found, the latter two phases of the original process can be greatly optimized for future applications. Moreover, $CphE_{al}$ was technically purified from the crude powder and the biochemical characteristics thereof were revealed.

SUMMARY OF THE INVENTION

The present invention thus provides
(1) a process for the enzymatic production of a dipeptide composition from a cyanophycin (CGP) or CGP-like polymer preparation, which process comprises degrading the polymer preparation with an CGPase;

(2) a preferred embodiment of the process of (1) above, wherein the CGPase
(i) has a molecular weight of 45 kDa, an optimum temperature of 50° C., and an optimum pH range of 7-8.5 and degrades CGP into β-Asp-Arg; and/or
(ii) is the *P. alcaligenes* DIP1 CGPase CphE$_{al}$ having been deposited with the DSMZ as DSM 21533, or is a mutant, derivative or fragment thereof capable of cleavage of CGp or CGP-like polymers into dipeptides;
(3) a CGPase as defined in (2) above; and
(4) a composition, pharmaceutical composition, medicament, food or feed supplement comprising a cyanophycin (CGP) or a CGP-like polymer or fragments thereof;
(5) the use of a cyanophycin (CGP) or a CGP-like polymer or fragments thereof for preparing a medicament for nutritional therapy, or as food or feed supplement;
(6) a method for nutritional therapy of a patient in need thereof, said method comprising administering to the patient a suitable amount of a composition comprising cyanophycin (CGP) or a CGP-like polymer or fragments thereof;
(7) preferred embodiments of (4) to (6) above, wherein the composition, pharmaceutical composition, medicament, food or feed supplement comprises dipeptides or a dipeptide mixture derived from the CGP or a CGP-like polymer by enzymatic proteolysis, preferably the dipeptide mixture being composed of β-aspartate-arginine and β-aspartate-lysine and/or being obtainable by the process of (1) or (2) above.

SHORT DESCRIPTION OF THE FIGURES

Figure 1B:
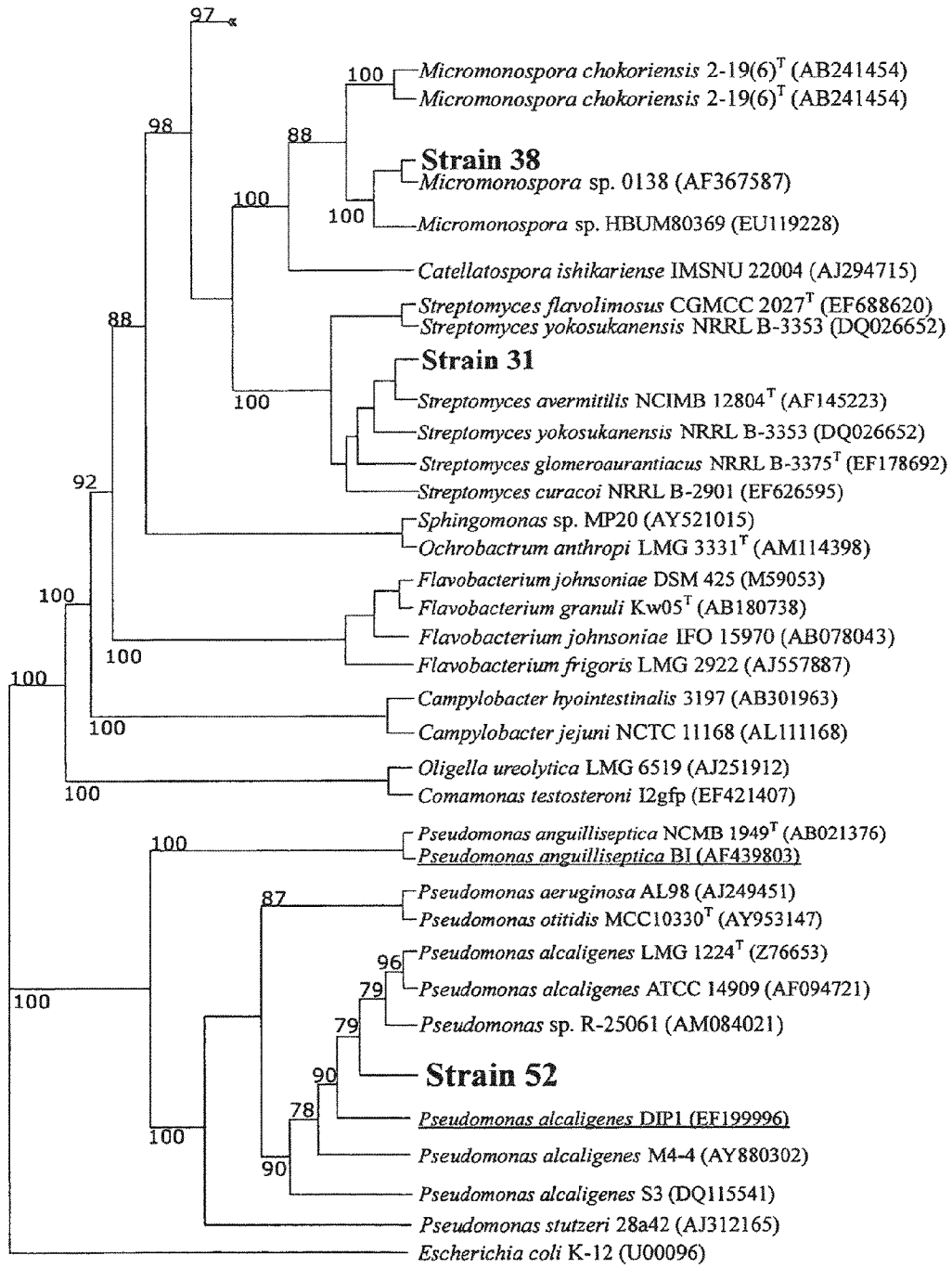

FIG. 1: Neighbour-joining tree based on 16S rDNA sequences showing the estimated phylogenetic relationships among the CGP degrading bacteria isolated previously as well as during this study. Bolded strains were isolated during this study. Underlined strains were previously investigated for CGP degradation (Obst, M. et al., J. Biol. Chem. 277: 25096-25105 (2002); Obst, M. et al., Biomacromolecules 5:153-161 (2004); Obst, M. et al., Appl. Environ. Microbiol. 71:3642-3652 (2005); Sallam, A. et al., Submitted for publication (2008)). *E. coli* K12 was used as outgroup. Accession numbers are given in parentheses. Bootstrap values are shown as percentages of 100 replicates. Bar, 2% sequence divergence.

Figure 2:

FIG. 2: Degradation halos caused by the extracellular CGPase form *P. alcaligenes* strain DIP1 on CGP-overlay agar plate; CphE: the crude powder before the degradation phase (phase III), CphE R: the recovered powder after the degradation phase.

Figure 3:
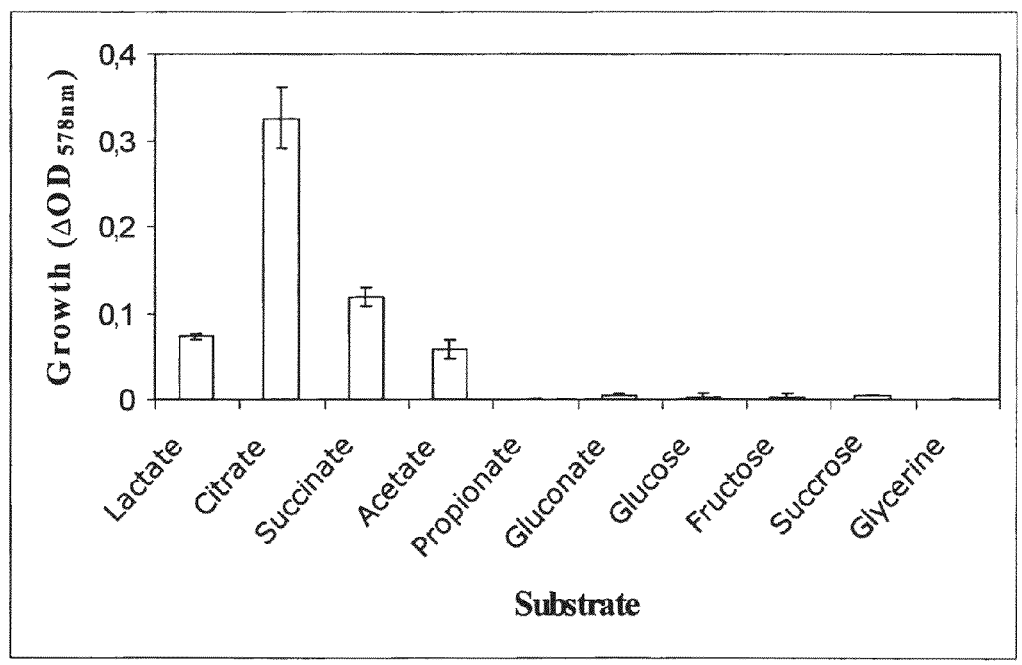

FIG. 3: Growth of *P. alcaligenes* strain DIP1 on different substrates. Cultivations were applied in 100 ml Klett-flasks with baffles; each flask contained 10 ml of SM medium and 1 g l$^{-1}$ of the tested substrate. Experiments were performed in duplicates which were inoculated from a preculture grown under the same test conditions. Growth was monitored by the increase in OD$_{578\,nm}$ after an incubation period of 24 h at 30° C.

Figure 4:
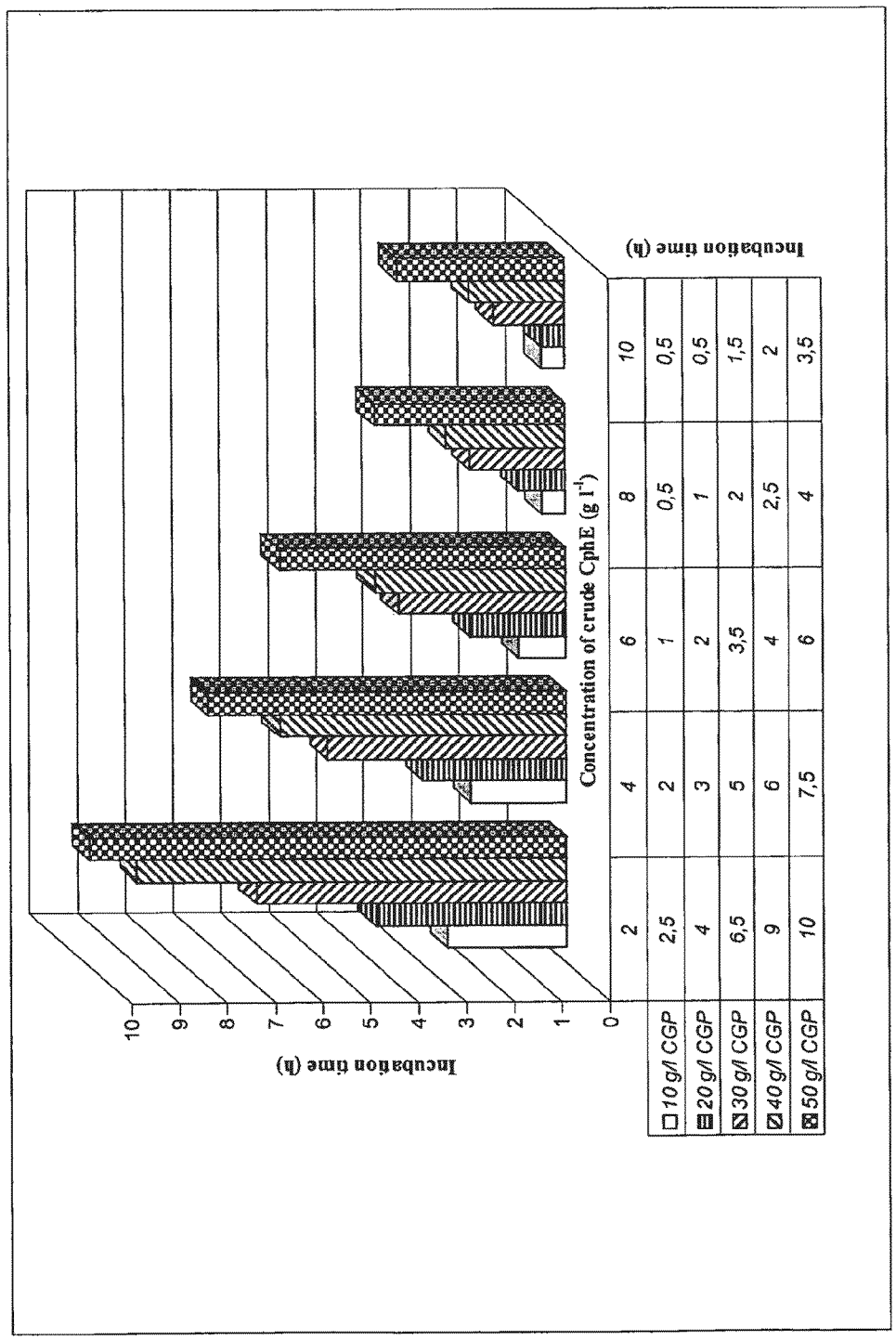

FIG. 4: The required incubation periods for the complete degradation of different CGP concentrations (10-50 g/l) under the catalytic effect of different crude CphE concentrations (1-10 g/l). The reaction tubes were incubated at 30° C. in a tube rotator with rotation rate of 3 rpm. The highest tested concentration of CGP (50 g/l) could be degraded within 10 h in the presence of 2 g/l crude CphE powder.

Figure 5:
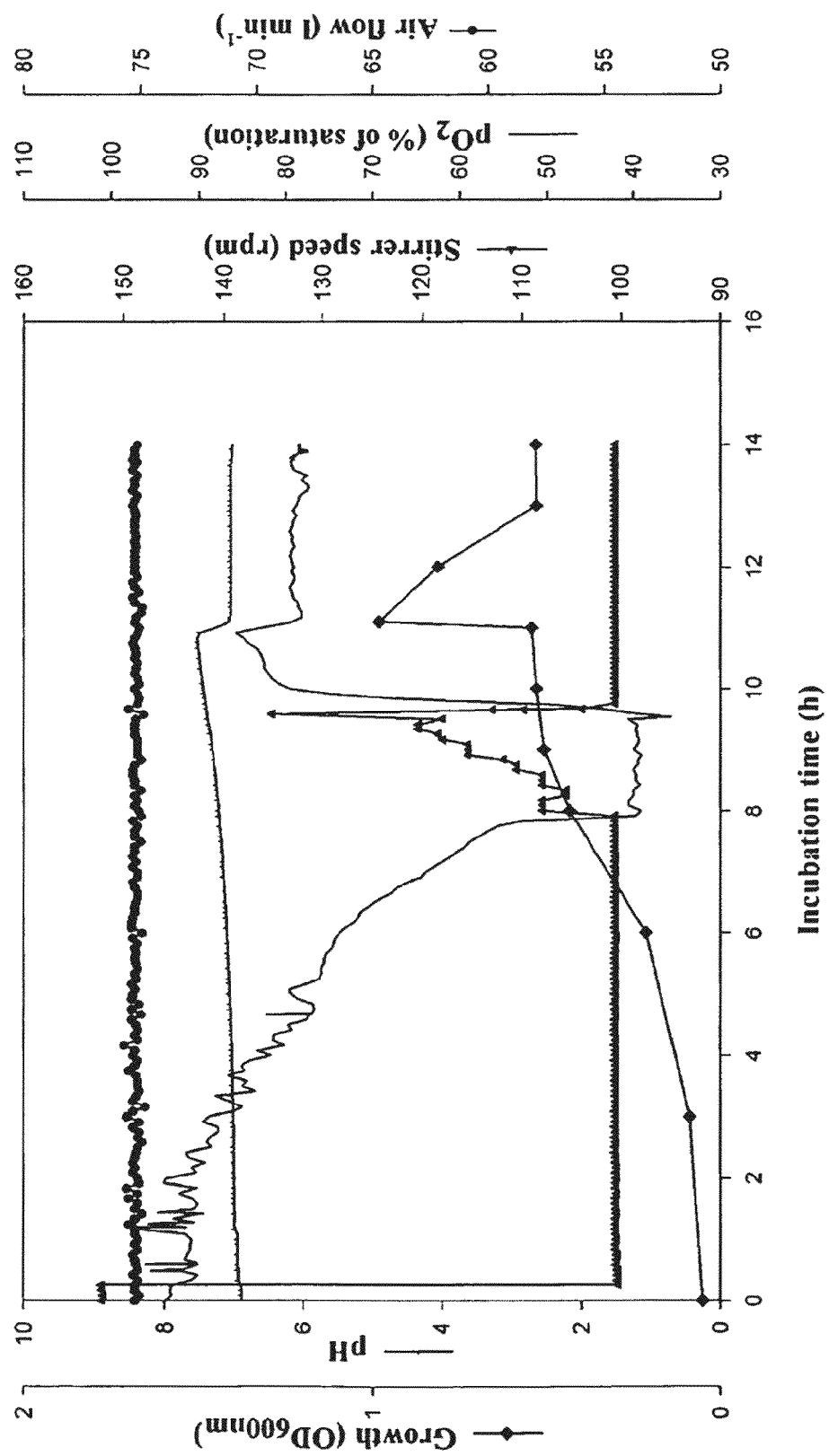

FIG. 5: Batch fermentation of *P. alcaligenes* DIP1 in Biostat D650 stirred tank reactor containing 420 l SM medium with g/l sodium citrate and inoculated with 4% (vol/vol) preculture. The preculture was cultivated in 2 l baffled-flasks containing 1 l of the same medium and incubated for 12 h at 30° C. The fermentation parameters and cultivation conditions in the Biostat D650 reactor were; pH of 6.9-7.5, temperature of 30° C., and aeration at 0.2 vvm. pO$_2$ was set to a minimum of 40% and was adjusted automatically by stirring which otherwise was kept at 100 rpm. The arrow indicates the time of induction. * Optical density at 600 nm (OD$_{600}$), ♦). * pH, ⊥). * Stirrer speed (rpm), ▲). * pO$_2$ (% of saturation), -). * Air flow (1 min$^{-1}$), ●).

Figure 6:
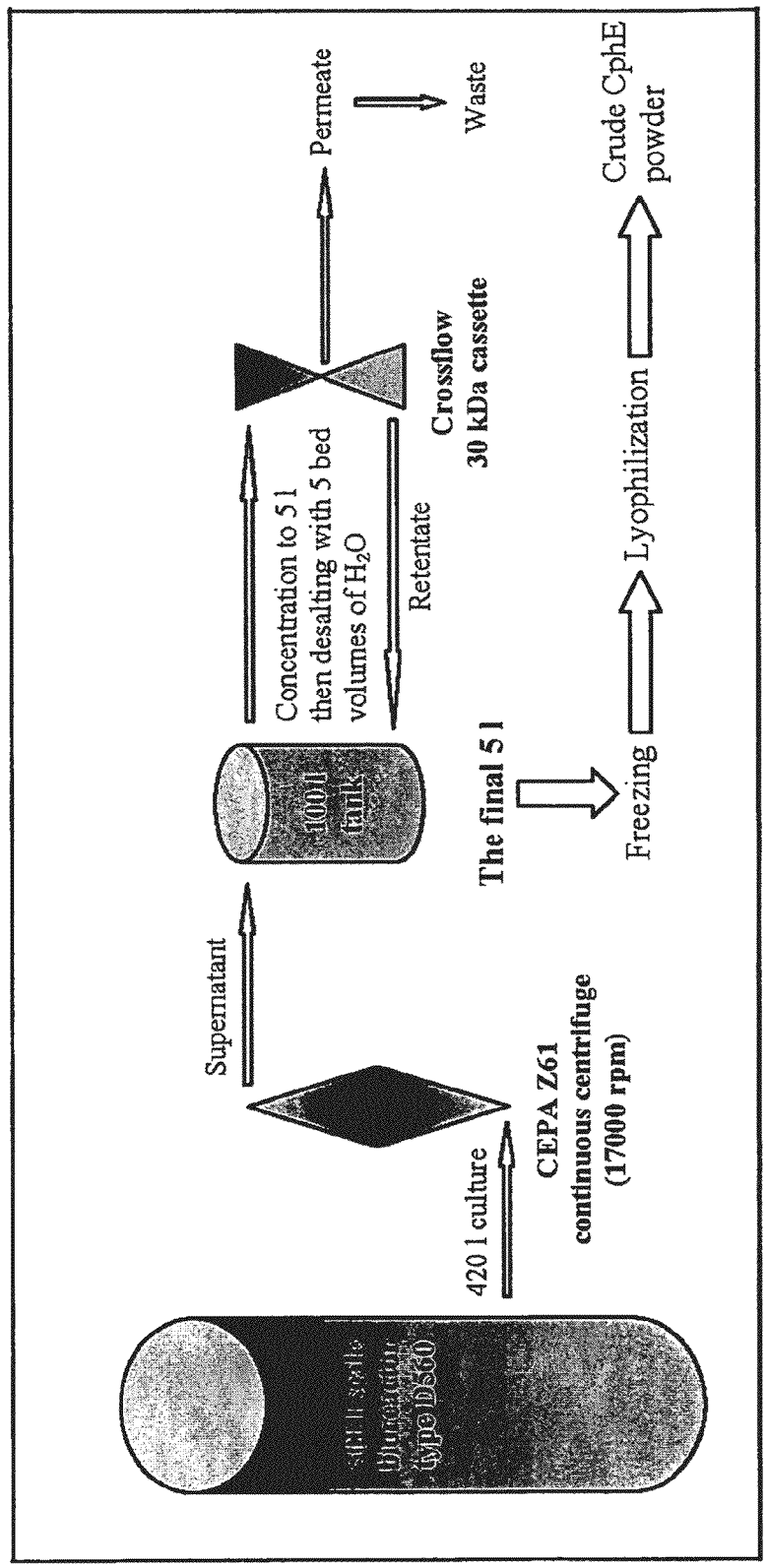

FIG. 6: A continuous system for harvesting, concentration and desalting of proteins in the fermentation supernatant of *P. alcaligenes* strain DIP1 (phase II). For harvesting, a CEPA Z41 continuous centrifuge was used to separate the cells, the supernatant was collected in a central 100 l tank. For concentration, a cross flow unit with a 30 kDa cassette was connected to the central tank; the concentrated retentate was re-pumped into the tank while the permeate was directly discarded. The flow rate of the cross flow was adjusted to maintain only 50 l in the tank. The final concentrated 5 l were desalted with 5 bed volumes of H$_2$O, frozen at −30° C., and lyophilized.

Figure 7:
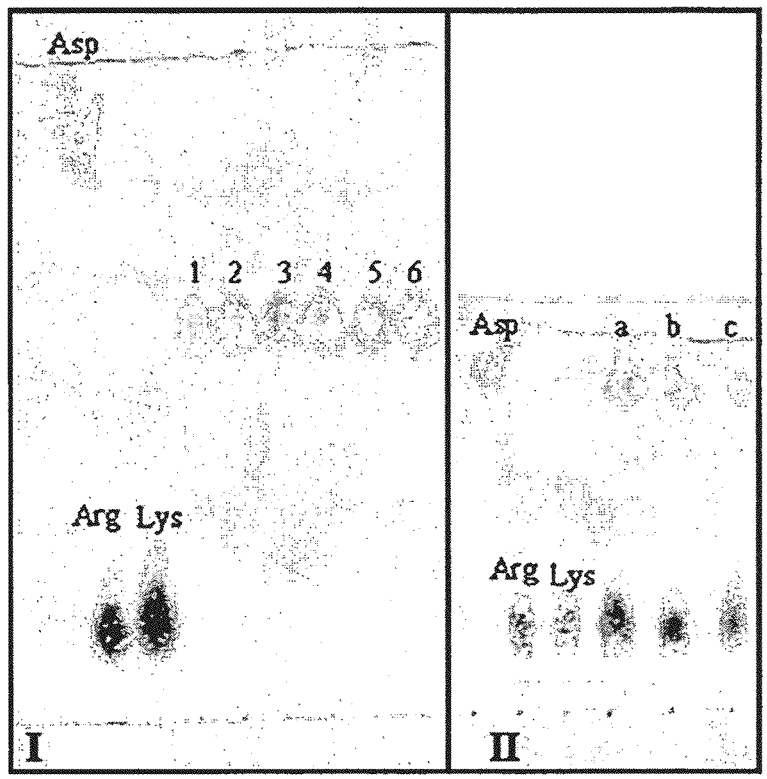

FIG. 7: TLC plates for the quality control of the produced CGP-dipeptides, I: Standard amino acids and direct dipeptide samples taken after the tested filtration systems; 1: 30 kDa.-COP. cross flow cassette. 2: filter-membrane (10 kDa.-COP). 3: filter-membrane (5 kDa.-COP). 4: filter-membrane (1 kDa.-COP). 5: filter-membrane (0.5 kDa.-COP). 6: CGP-dipeptides (final charge after cross flow and lyophilization). II: Standard amino acids and hydrolyzed samples of; a: CGP-dipeptides (final charge after cross flow and lyophilization). b: Asp-Arg dipeptides. c: Asp-Lys dipeptides. (b, c; Sigma Aldrich, Deisenhofen, Deutschland). only one spot was indicated for all direct samples (I) while hydrolyzed samples showed typical spots for the standard amino acids aspartate, arginine and lysine (II).

Figure 8:
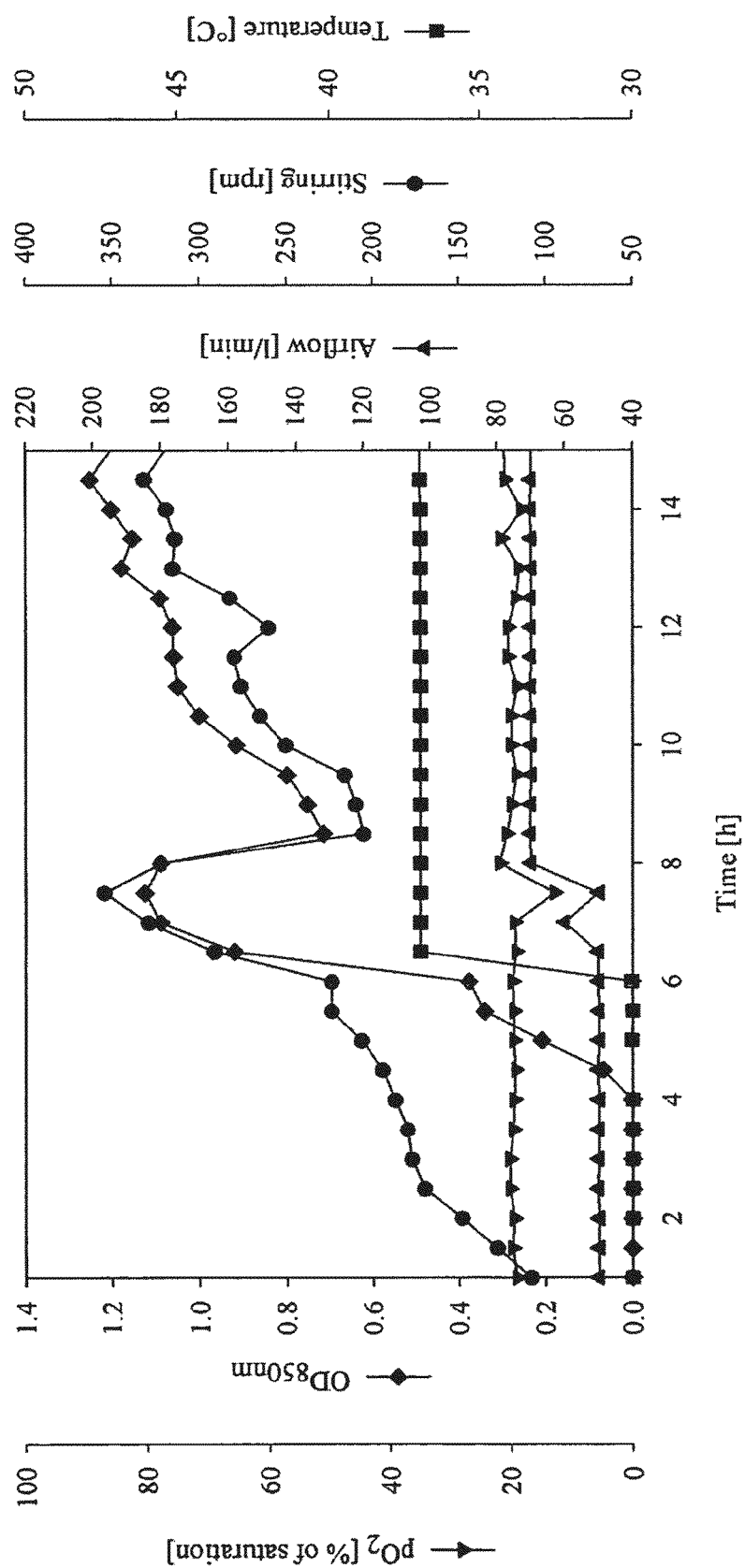

FIG. 8: Batch fermentation of *E. coli* DH1 (pMa/c5-914::cphA$_{PCC6803}$) in Biostat D650 stirred tank reactor containing 400 l of 7% (vol/vol) protamylase medium with 100 mg l$^{-1}$ ampicillin. The preculture (4%, vol/vol) was prepared in 2 l flasks each containing 1 l of the same medium as that for fermentation and incubated for 20 h at 30° C. Fermentation parameters and cultivation conditions in the Biostat D650 reactor were pH 7.5, aeration at 0.17 vvm, pO$_2$ was kept constant at 20% and was adjusted automatically by stirring. Fermentation was run for 15 h, the first 6 h at 30° C. then at 37° C. to induce expression of CGP-synthetase. Turbidity (OD$_{850}$) (♦), pO$_2$ (% of saturation) (▼), Aeration (l/min) (▲), Stirring (rpm) (●), Temperature (° C.) (■).

Figure 9:
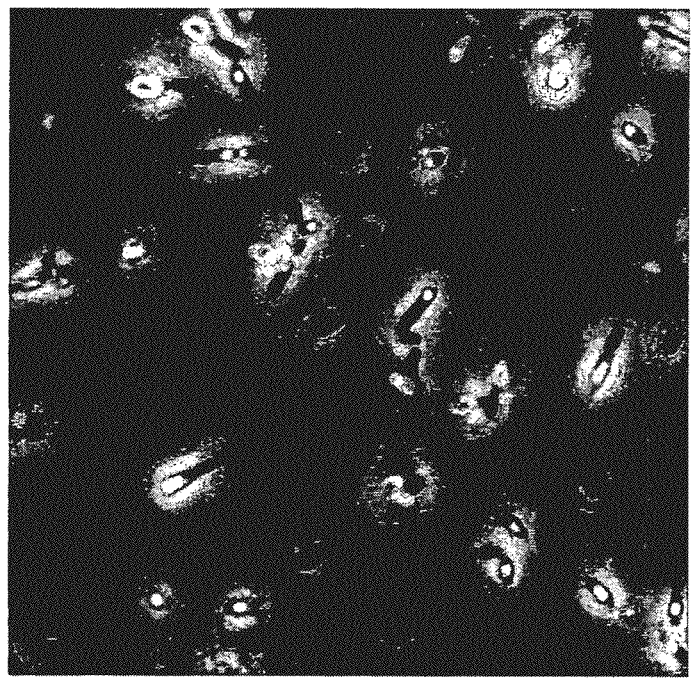

FIG. 9: Phase-contrast micrograph of cells of *E. coli* DH1 (pMA/c5.914::cphA$_{PCC6803}$) at the 15$^{th}$ h of fermentation in Biostat D650 reactor on 7% (vol/vol) protamylasse medium. CGP grana appear as light-reflecting accumulations in the cells. Bar; 10 μm.

Figure 10:
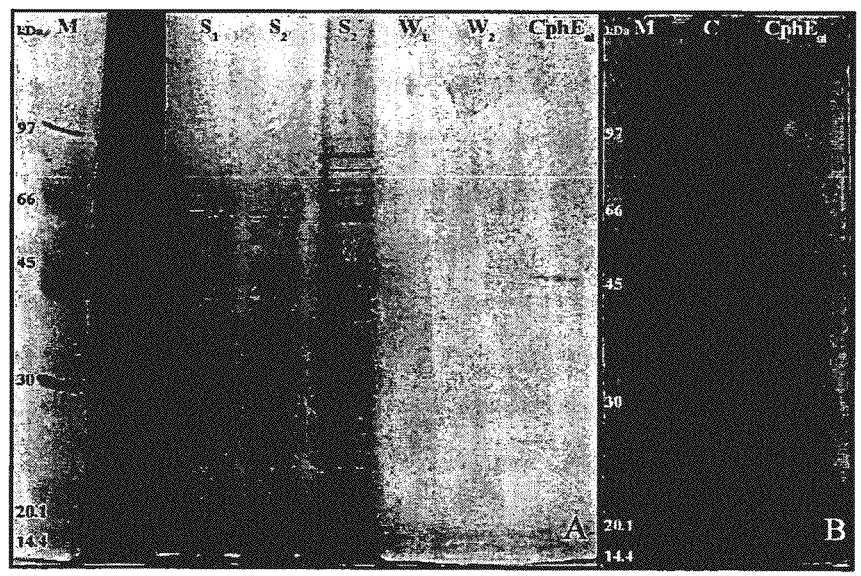

FIG. 10: SDS-PAGE of purification steps of CphE$_{al}$ from *P. alcaligenes* strain DIP1 via specific binding on CGP. Gel A: SDS-PAGE stained by silver nitrate method; M: molecular mass standard proteins, C: control of crude CphE$_{al}$, S1: supernatant sample immediately after mixing CGP and crude CphE$_{al}$ together, S2: supernatant sample after 6 min binding time, S2': same as S1 after 10 folds concentration, W1, W2: supernatant samples after both washing steps. Gel B: SDS-PAGE with triple-volume of the purified CphE$_{al}$ as in A and stained longer with silver nitrate. Few other low-concentrated protein bands can be observed in addition to that of CphE$_{al}$ at 45 kDa.

DETAILED DESCRIPTION OF THE INVENTION

In the process of aspect (1) of the invention the dipeptide composition may be composed of a single dipeptide or of a mixture of dipeptides. It is however preferred that the dipeptides comprise amino acid residues selected from aspartate, arginine, lysine and other amino acid residues present in the CGP-like polymer. Particularly preferred is that the dipeptides are selected from β-aspartate-arginine and β-aspartate-lysine.

A "CGP" and "CGP-like polymer" according to the invention is a peptidic structures essentially comprised of one or more dipeptide units, preferably said dipeptides units are composed of two of the following amino acid residues aspartic acid, arginine, lysine, glutamic acid, citrulline, ornithine, canevanine and the like.

A great variety of CGPases known in the art may be utilized for the CGP degradation (see Tables 2 and 4). It is, however, preferred that the CGPase is a CGPase from *P. alcaligenes*, particularly preferred from *P. alcaligenes* strain DIP1. According to aspect (2) of the invention the CGPase (i) has a molecular weight of 45 kDa, an optimum temperature of 50° C., and an optimum pH range of 7-8.5 and degrades CGP into β-Asp-Arg; and/or (ii) is the *P. alcaligenes* DIP1 CGPase CphE$_{al}$ having been deposited with the DSMZ as DSM 21533, or is a mutant, derivative or fragment thereof capable of cleavage of CGP or CGP-like polymers into dipeptides. The mutants, derivatives or fragments of the aforementioned native CGPase include fragments (having at least 50 consecutive amino acid residues of the native sequence, preferably N- and/or C-terminal truncation products, wherein up to 50, up to 30, or up to 10 terminal amino acid residues are removed), derivatives (notably fusion products with functional proteins and peptides such as secretion peptides, leader sequences etc., and reaction products with chemical moieties such as PEG, alcohols, amines etc.) and mutants (notably addition, substitution, inversion and deletion mutants, having at least 80%, preferably at least 90%, most preferably at least 95% sequence identity with the native enzyme on the amino acid basis or wherein 1 to 20, preferably 1 to 10, consecutive or separated amino acid residues are added, substituted, inverted and/or deleted; for substitution mutants conservative substitution is particularly preferred), provided, however, that said modified CGPases have the enzymatic activity of the native CGPase.

The process of aspects (1) and (2) of the invention may further comprise preparing the CGP or CGP-like polymer preparation by culturing a prokaryotic or eukaryotic producing cell line. The producing cell line may be any cell line capable of producing the CGP or CGP-like polymer. It is preferred that the producing cell line is selected from *Escherichia coli, Raistonia eutropha, Acinetobacter baylyi, Corynebacterium glutamicum, Pseudomonas putida*, yeast strains, and plant biomass. Particularly preferred producing cell lines are *Raistonia eutropha* H16-PHB⁻4-Δeda (pBBR1MCS-2::cphA$_{6308}$/edaH16) and *E. coli* DH1 (pMa/c5-914::cphA$_{PCC6803}$).

The above process may further comprise the steps of isolating, purifying and/or chemically modifying the CGP product obtained by cultivating the producing cell line. Such isolation, purification and chemical modification separation may be effected by methods well established in the art.

It is however preferred for the process of aspects (1) and (2) that the CGP product obtained by cultivating the producing cell line is directly, i.e. without isolation or purification subjected to degradation with the CGPase.

In another preferred embodiment the process of aspects (1) and (2) further comprises purifying or separating the degradation product and/or chemically modifying the degradation product. Again, such purification, separation or chemical modification may be effected by methods well established in the art.

Aspect (3) of the invention pertains to a CGPase that
(i) has a molecular weight of 45 kDa, an optimum temperature of 50° C., and an optimum pH range of 7-8.5 and degrades CGP into β-Asp-Arg; and/or
(ii) is the *P. alcaligenes* DIP1 CGPase CphE$_{al}$ having been deposited with the DSMZ as DSM 21533, or is a mutant, derivative or fragment thereof capable of cleavage of CGp or CGP-like polymers into dipeptides. As to the mutants, derivatives and fragments it is referred to the definition given above.

The pharmaceutical composition, medicament, food or feed supplement according to aspects (4), (5) and (6) of the invention may further contain pharmaceutically or dietetically acceptable suitable carriers, binders etc. They may further contain additional active compounds for the respective pharmaceutical purpose.

The pharmaceutical composition is particularly suitably for nutritional therapy. The type of nutritional therapy of course depends on the amino acids present within the Composition/medicament as will be apparent from the following:

Recent advances in nutritional therapy of critically ill patients rendered a good understanding of the necessity of certain amino acids for maintaining tissue protein homeostasis during illness (Witte, M. B. and Barbul A., Wound Rep. Reg. 11:419-423 (2003)). Previously, amino acids were either classified as nonessential (dispensable) or essential (non-dispensable). However, with better understanding of the in vivo physiology involving amino acids, an alternative classification was proposed that redefines the requirements of certain amino acids as being conditionally non-dispensable (Laidlaw, S. A. and Kopple, J. D., Am. J. Clin. Nutr. 46:593-605 (1987)). This made the use of such amino acids, solely or as part of a complete nutritional regimen, attractive to improve nutritional outcome, immune response, and tissue recovery. In the following section, findings regarding the physiology and the mechanism of action of the three amino acids, that also constitute CGP, are discussed. These amino acids are: the nonessential L-Aspartate, the semi-essential L-Arginine, and the essential amino acid L-Lysine. A special emphasis is given on arginine due to its numerous physiological effects.

L-Aspartate: The nonessential L-Aspartate has a molecular mass of 133.10 g/mol and is a dicarboxylic amino acid. Most L-Aspartate can be found in proteins while small amounts thereof are also found in the free form in body fluids and in plants (Barrett, G. C. and Elmore D. T. Amino Acids and Peptides. Cambridge University Press, Cambridge, UK (1998)). L-Aspartate is a constituent of the natural biopolymer CGP and the synthetic sweetener Aspartame. Aspartic acid is slightly soluble in water and more water-soluble in the salt form. Dietary aspartate is absorbed from the small intestine by active transportation to enter the portal circulation then transported to the liver, where much of it is metabolized to protein, purines, pyrimidines plants (Barrett, G. C. and Elmore D. T. Amino Acids and Peptides. Cambridge University Press, Cambridge, UK (1998)). L-Aspartate can also serve as a source for energy in the citric acid cycle and thus is supposed to be effective against fatigue (see also below: Asp-Arg). Aspartate is used in drug delivery for cations like $Mg^{2+}$, $K^+$, $Ca^{2+}$, $Zn^{2+}$, or for other amino acids to increase their bioavailability (Cynober, L. A. Metabolic and therapeutic aspects of amino acids in clinical nutrition. 2nd ed. CRC Press LLC, Boca Raton, USA (2003)).

L-Arginine: L-Arginine is a strongly basic amino acid with a molecular mass of 174.2 g/mol and is found in most proteins. It contains four nitrogen atoms per molecule, and is therefore the most abundant nitrogen carrier in humans and animals (Appleton, J., Altern. Med. Rev. 7:512-522 (2002)). Arginine is essential for fish (Ahmed, I. and Khan, M. A., Aquacult. Nutr. 10:217-225 (2004)) whereas in mammals, it is considered semi-essential because it can be compensated via nutritional intake or via de novo synthesis (endogenous). In the kidney, most endogenous arginine is derived from Citrulline, a by-product of glutamine metabolism in the gut or liver. However, because arginine biosynthesis does not increase to compensate depletion or inadequate supply, dietary intake (approximately 5-6 g/day for an average human, Witte, M. B. and Barbul. A., Wound Rep. Reg. 11:419-423 (2003)) remains the primary determinant of plasma arginine levels. About 50% of the ingested arginine is directly utilized in the small bowel while the rest is released into the portal circulation. In general, about the half of ingested arginine is rapidly converted to ornithine, primarily by the enzyme arginase (Modolell, M. et al., Eur. J. Immunol. 25:1101-1104 (1995); Witte, M. B. and Barbul. A., Wound Rep. Reg. 11:419-423 (2003)). Ornithine, in turn, can be metabolized to glutamate and proline, or through the enzyme ornithine decarboxylase into polyamines (Boutard, V. et al., J. Immunol. 155:2077-2084 (1995)). Rest arginine is processed by one of four other enzymes: nitric oxide synthase (to become nitric oxide), arginine:glycine amidinotransferase (to become creatine), arginine decarboxylase (to become agmatine), or arginyl-tRNA synthetase (to become arginyl-tRNA, a precursor to protein synthesis) (Vodovotz, Y. et al., J. Exp. Med. 178:605-613 (1993)).

Arginine has significant effects on endocrine functions in humans and animals, particularly on adrenal and pituitary secretory functions. However, little is known about the exact mechanism by which arginine exerts these effects. Arginine is the biologic precursor of nitric oxide (NO), an endogenous messenger molecule involved in a variety of endothelium-dependent physiological effects in the cardiovascular system (Witte, M. B. and Barbul. A., Wound Rep. Reg. 11:419-423 (2003)). Thus, many of the clinical effects of arginine are thought to be mediated by its effects on endothelial-derived relaxing factor. NO-synthase has two variants (Rohdewald, P. and Ferrari V., Patent Application US2004137081 (2004); the constitutive (cNOS) with its isoforms; eNOS (in vascular endothelial lining) and nNOS (in neurons), and the inducible variant (iNOS) found in macrophages, white blood cells, fibroblasts, endothelial cells, and keratinocytes. The function of NO may differ with its cellular source; fibroblast NO supports collagen synthesis, while endothelial NO affects angiogenesis, and macrophage NO is cytostatic to bacteria (Rohdewald, P. and Ferrari V., Patent Application US2004137081 (2004). On the other hand, arginase shares and competes on the natural substrate of NOS, namely; L-Arginine. L-hydroxyarginine and nitrite, the intermediate and end product, respectively, of the NO pathway, are both strong arginase inhibitors (Hrabak, A. et al., FEBS Lett. 390: 203-206 (1996)). Conversely, urea, the end product of arginase activity, inhibits NO formation and NO-dependent processes (Witte, M. B. and Barbul. A., Wound Rep. Reg. 11:419-423 (2003)).

Arginine in cardiovascular conditions: Arginine proved to be beneficial if administrated to patients with cardiovascular conditions in numerous clinical trials (reviewed by Appleton, J., Altern. Med. Rev. 7:512-522 (2002)). For example, oral arginine supplementation dramatically improved exercise capacity and tolerance in patients with angina pectoris (Bednarz, B. et al., Int. J. Cardiol. 75:205-210 (2000)), and significantly improved their blood flow, arterial compliance, and renal function in cases with congestive heart failure (CHF) (Watanabe, G. H. et al., J. Hypertens. 18:229-234 (2000)). Animal studies suggested anti-atherogenic effects of supplemental arginine, including improved vasodilatation, inhibition of plaque formation, decreased thickening of the aortic tunica intima, and a normalized platelet aggregation in hypercholesterolemic human adults (Nakaki, T. and Kato R., Jpn J. Pharmacol. 66:167-171 (1994)). Moreover, early provision of arginine improved hypertension, prevented renal failure in rats and humans (Sanders, P. W., Am. J. Kidney Dis. 28:775-782 (1996)), and enhanced the response of hypertensive patients to medicaments such as enalapril (Pezza, V. et al., Am. J. Hypertens. 11:1267-1270 (1998)). Additionally, arginine significantly improved symptoms of intermittent claudication (Böger, R. H. et al., J. Am. Coll. Cardiol. 32:1336-1344 (1998)), and of preeclampsia (Roberts, J. M., Am. J. Kidney Dis. 33:992-997 (1999)).

Arginine in growth hormone (GH) secretion and athletic performance: Growth hormone is responsible for enhancing muscle growth, burning fat and maintaining the immune system, however, its secretion begins to decline in the human body by the age of thirty (reviewed by Dean, W. and Pryor, K., Growth hormone: amino acids as GH secretagogues—a review of the literature. Vit. Res. News; available at the website vrp.com (2001)). Although the mechanism is not well understood, arginine is known to enhance GH secretion. Furthermore, clinicians routinely use an arginine infusion test to determine the responsiveness of the pituitary gland to releasing GH in humans (Penny, R. et al., J. Clin. Endocrinol. 29:1499-1501 (1969)). Low dose intravenous (IV) infusion of arginine was associated with a 52% rise in serum arginine and a significant increase in serum GH levels. On the other hand, oral arginine, unlike IV arginine, was suggested to be ineffective means of enhancing GH secretion (Marcell, T. J. et al., J. Gerontol. 54:395-399 (1999)), while high doses of oral arginine aspartate were suggested to act as a growth hormone secretagogue only at night (Besset, A. et al., Acta Endocrinol. 99:18-23 (1982)). In fish, arginine is an essential amino acid, thus, dietary arginine is essential for optimum growth and efficient feed utilization and its deficiency causes reduced growth rate, lowered immune response, and increased mortality (Ahmed, I. and Khan, M. A., Aquacult. Nutr. 10:217-225 (2004)).

Arginine in wound, burns, critical trauma, and senile dementia: Because arginine is intimately involved in cell signaling through the production of nitric oxide and with cell proliferation through its metabolism to ornithine and the other polyamines, numerous studies showed that its supplementation is essential for healing. This effect is not dependant on the route of administration and is supposed to be associated with the synthesis pathways of collagen, NO, ornithine, and polyamines (Witte, M. B. and Barbul. A., Wound Rep. Reg. 11:419-423 (2003)).

Collagen synthesis is essential for scar formation, which is the basis for most mammalian healing. Rats fed arginine-free diet showed impaired wound healing while humans and animals fed arginine-enriched diet had improved collagen deposition and wound breaking strength (Barbul, A. et al., Surgery 108:331-336 (1990)). Arginine effect on collagen synthesis is supposed to be mediated in part via NO synthesis because iNOS inhibitors decreased collagen deposition and retarded healing of incisional wounds, whereas higher levels of NO metabolites were found in wound fluids after arginine-supplementation (Murrell, G. A. C. et al., Inflamm. Res. 46:19-27 (1997); Schäffer, M. R. et al., Eur. J. Surg. 165:262-267 (1999)). Effects of NO on wound healing are even suggested to be systemically mediated (Witte, M. B. and Barbul. A., Wound Rep. Reg. 11:419-423 (2003)) because: 1) arginine-free nutrition inhibits the induced NO synthesis in several organs not only at the wound site; 2) NO mediates inflammation-induced edema and inhibits cell infiltration into granulomas; 3) the effect of NO on wound healing is not only iNOS-mediated since eNOS knock-out mice also show impaired healing; and 4) iNOS inhibitors have a high lethality in high concentrations. Additionally, while wound contraction contributes largely to the closure of open wounds, excisional wounds closure is delayed by iNOS inhibition (Stallmeyer, B. et al., J. Invest. Dermatol. 113:1090-1098 (1999)) and iNOS knock-out mice show delayed closure of excisional wounds that can be reversed by transfection with iNOS-cDNA (Yamasaki, K. et al., J. Clin. Invest. 101:967-971 (1998)). All this data led to believing that arginine metabolism via NOS is essential for the positive effects of arginine on healing (Shi, H. P. et al., Surgery 128:374-378 (2000)).

Induction or overexpression of arginase, which represents the first step in polyamine biosynthesis, enhances endothelial cell proliferation (Wei, L. H. et al., Proc. Natl. Acad. Sci. USA 98:9260-9264 (2001); Witte, M. B. and Barbul. A., Wound Rep. Reg. 11:419-423 (2003)). Arginine is also known to enhance wound healing by stimulating host and wound T-cell responses, which then increase fibroblastic responses (Barbul, A. et al., Surgery 108:331-336 (1990)). In healthy humans, arginine enhances the mitogenic activity of peripheral blood lymphocytes and greatly reduces post-traumatic impairment in lymphocyte blastogenesis (Daly, J. M. et al., Ann. Surg. 208:512-23 (1988)). Arginine has been shown to be critical for bone marrow lymphocyte differentiation. Because T-lymphocytes are essential for normal wound healing, T-cell depleted mice and rats have a significantly impaired wound healing. Other studies showed that the beneficial effects of supplemental arginine on wound healing are similar to the effects of administered GH to wounded animals or burned children (Jorgensen, P. H and Andreassen, T. T., Acta Chir. Scand. 154:623-626 (1988); Herndon, D. N. et al., Ann. Surg. 212:424-9 (1990)), which is due to the well-known high secretagogue activity of arginine on the pituitary and pancreatic glands. This was confirmed by tests on hypophysectomized animals where arginine did not affect wound healing (Wei, L. H. et al., Proc. Natl. Acad. Sci. USA 98:9260-9264 (2001); Witte, M. B. and Barbul. A., Wound Rep. Reg. 11:419-423 (2003)).

Seifter, E. et al., Surgery 84:224-230 (1978) showed that arginine becomes essential in post-traumatic situations; arginine-deficient rats subjected to minor trauma showed significantly more weight loss and mortalities. Also burn injuries significantly increase arginine oxidation and fluctuation in its reserves. The often used total parenteral nutrition (TPN) increases conversion of arginine to ornithine and proportionally increases irreversible arginine oxidation. Elevated arginine oxidation, coupled with limited de novo synthesis, make arginine conditionally essential in severely burned patients receiving TPN (Yu, Y. M. et al., Am. J. Physiol. Endocrinol. Metab. 280:E509-E517 (2001)). Several other studies demonstrated that arginine reduces length of hospital stay, acquired infections, immune impairment among burn and trauma patients (Appleton, J., Altern. Med. Rev. 7:512-522 (2002)), and lipid peroxidation in elderly patients with senile dementia (Ohtsuka, Y. and Nakaya J., Am. J. Med. 1:108-439 (2000)). These numerous observations, coupled with relative safety, made the use of arginine very attractive for the care of traumatized, burned, or seriously ill patients (Witte, M. B. and Barbul. A., Wound Rep. Reg. 11:419-423 (2003)).

Arginine in immunomodulation and cancer: Arginine is a potent immunomodulator and was shown to have beneficial effects in catabolic conditions such as sepsis and postoperative stress (Evoy, D. et al. Nutrition 14:611-617 (1998); Appleton, J., Altern. Med. Rev. 7:512-522 (2002)). Arginine may also be of benefit in individuals with HIV/AIDS. The combination of glutamine, arginine, and HMB (hydroxymethylbutyrate) prevented loss of lean body mass in individuals with AIDS (Swanson, B., Nutrition 18:688-690 (2002)). Animal and human trials showed that large doses of arginine may interfere with tumor induction and that short-term supplementation with large doses of arginine assists in maintaining of the immune functions during chemotherapy (Appleton, J., Altern. Med. Rev. 7:512-522 (2002)). Arginine in diabetes and insulin resistance: Reduced plasma arginine level and impaired endothelium-dependent relaxation are observed in humans and animals with diabetes mellitus (DM). Endothelial NO deficiency was supposed to be a likely reason for this. Therefore, arginine supplementation was suggested to improve these conditions; IV arginine reduced blood pressure and platelet aggregation in patients with DM type 1 (Giugliano, D. et al., Am. J. Physiol. 273:E606-E612 (1997)), while low-dose IV arginine improved insulin sensitivity in obese and type 2 DM patients as well as in healthy subjects (Wascher, T. C. et al., Eur. J. Clin. Invest. 27:690-695 (1997)). Arginine may also counteract lipid peroxidation and thereby reduce microangiopathic long-term complications of DM. Moreover, a double-blind trial showed that oral arginine supplementation significantly improved peripheral and hepatic insulin sensitivity in patients with type 2 DM (Appleton, J., Altern. Med. Rev. 7:512-522 (2002)).

Arginine in gastrointestinal conditions: The action of arginine on NO, gastrin, and polyamines which exerts its hyperemic, angiogenic, and growth-promoting effects were associated with an acceleration in ulcer healing during preliminary studies (Brzozowski, T., J. Gastroenterol. 32:442-452 (1997)). Additionally, NO plays an important role in the regulation of gastrointestinal motility. Oral arginine supplementation significantly decreased the frequency and intensity of chest pain attacks in patients with esophageal motility disorders (Appleton, J., Altern. Med. Rev. 7:512-522 (2002)). Similarly, the L-Arginine-NO pathway is involved in the regulation of gallbladder motility and L-Arginine ingestion increased fasting and residual gallbladder volumes (Luiking, Y. C. et al., Am. J. Physiol. 274:984-991 (1998)). Arginine in genitourinary conditions: A survey carried out in the United States (1999) indicated that 31% of men and 43% of women aged 18 to 59 years have varying degrees of sexual dysfunction (Christianson, D. W., Acc. Chem. Res. 38:191-201 (2005)). This problem can have physiological or psychological reasons or both. In men, sexual dysfunction is briefly described as erectile dysfunction (impotence or ED), whereas in women, sexual dysfunction is classified in four main categories: hypoactive sexual desire, orgasmic disorder, sexual pain disorder, and sexual arousal disorder (Basson, R. et al., J. Urol. 163:888-893 (2000)). The latter, defined as the inability to achieve or maintain sufficient sexual excitement including clitoral erection and genital engorgement, is analogous to male ED in being caused by deficiency in genital blood circulation. This can result in both genders from physiological defects in the enzyme-catalyzed reactions governing blood flow into and out of the corpus cavernosum, a muscularized chamber of expandable tissue that becomes engorged with blood in the erect penis or clitoris (Christianson, D. W., Acc. Chem. Res. 38:191-201 (2005)).

Penile erection, in particular, is a hemodynamic process involving increased arterial inflow and restricted venous outflow following central or peripheral sexual stimulation (Musicki, B. et al., Biol. Reprod. 70:282-289 (2004)). The involvement of NO, generated by both endothelial NO synthase (eNOS) and the neuronal penile NO synthase (PnNOS) as the main mediator of penile erection, is well documented. NO diffuses to the adjacent target smooth muscle tissue stimulating guanylylcyclase to produce cyclic guanosine monophosphate (cGMP) leading to relaxation of the corpora cavernosa (Ferrini, M. et al., Biol. Reprod. 64:974-982 (2001)). Conversely, erection is terminated when cGMP-specific phosphodiesterases (PDEs) hydrolyze cGMP to 5'-GMP leading to smooth muscle contraction (Firoozi, F. et al., Br. J. Urol. Int. 96:164-168 (2005)). Thus, L-Arginine and drugs acting on the L-Arginine-NO pathway are attractive as therapeutics for ED. Moreover, selective inhibitors of PDEs as Sildenafil citrate (Viagra®), which inhibit cGMP degradation and thereby prolong erection, are widely applied. However, Sildenafil has a systemic vasodilating and hypotensive effect leading to a broad range of side effects starting from headaches, and may even reach death (Cohen, J. S., Ann. Pharmaco. Ther. 35:337-342 (2001)).

L-Arginine "nutraceuticals" are often explored as remedies for male and female sexual arousal. For example; long term or supplementation with supra-physiologic doses of dietary L-Arginine enhanced intracavernosal pressure and erectile function in rat (Moody et al. 1997), and men, respectively. Long term L-Arginine supplementation improved ED in men with abnormal nitric oxide metabolism (Zorgniotti and Lizza 1994), while in another study on women, L-Arginine nutritional supplement improved satisfaction with overall sexual life in 73.5% of the tested subjects (Ito, T. Y. et al., J. Sex Marital Ther. 27:541-549 (2001)). On the other hand, NOS is not the only enzyme affecting penile erection, arginase shares its sole substrate arginine and is coexpressed with NOS in smooth muscle tissue in male and female genitalia. Therefore, arginase inhibition may enhance the NO-dependent physiological processes required for sexual arousal. Because many arginase inhibitors have no apparent effect on systemic arterial blood pressure, it became another potential target for the treatment of sexual dysfunction (Christianson, D. W., Acc. Chem. Res. 38:191-201 (2005)).

Arginine in infertility and pregnancy: Arginine is required for normal spermatogenesis in men (Appleton, J., Altern. Med. Rev. 7:512-522 (2002)). Over 50 years ago, researchers found that feeding adult men on arginine deficient diet for nine days decreased sperm counts by 90% and increased the percentage of non-motile sperms approximately 10-folds (Holt, L. E. Jr. and Albanese, A. A., Trans. Assoc. Am. Physicians 58:143-156 (1944)). Oral administration of 0.5 g arginine-HCl per day to infertile men for several weeks markedly increased sperm counts and motility in a majority of tested patients, and resulted in successful pregnancies (Tanimura, J., Bull. Osaka Med. School 13:84-89 (1967)). Similar effects on oligospermia and conception rates have been reported in other preliminary trials (Tanimura, J., Bull. Osaka Med. School 13:84-89 (1967); De-Aloysio, D. et al., Acta Eur. Fertil. 13:133-167 (1982)) and improved fertility. However, when baseline sperm counts were less than 10 million/ml, arginine supplementation could not help (Mroueh, A., Fertil. Steril. 21:217-219 (1970); Appleton, J., Altern. Med. Rev. 7:512-522 (2002)).

Oral arginine supplementation for women poorly responding to in vitro fertilization improved ovarian response, endometrial receptivity, and pregnancy rate in one study (Battaglia, C. et al., Hum. Reprod. 14:1690-1697 (1999)). Additionally, intravenous arginine infusion (30 g over 30 min) in women with premature uterine contractions, transiently reduced uterine contractility (Facchinetti, F. et al., J. Perinat. Med. 24:283-285 (1996)). Further evidence from human and animal studies indicated that nitric oxide inhibits uterine contractility during pregnancy and may help and thereby acting against preterm labor and delivery (Appleton, J., Altern. Med. Rev. 7:512-522 (2002)).

In patients with interstitial cystitis (IC), oral arginine over six months significantly decreased urinary voiding discomfort, abdominal pain, and vaginal/urethral pain. Urinary frequency during day and night was also significantly decreased (Smith, S. D. et al., J. Urol. 158:703-708 (1997); Appleton, J., Altern. Med. Rev. 7:512-522 (2002)).

L-Lysine: L-Lysine is an essential basic amino acid, has a molecular weight of 146.19 g/mol, and carries a positive charge at physiological pH. While the D-stereoisomer of lysine is not biologically active, L-Lysine is a known food additive for human and animal (Cynober, L. A. Metabolic and therapeutic aspects of amino acids in clinical nutrition. 2nd ed. CRC Press LLC, Boca Raton, USA (2003)). Ingested L-Lysine is absorbed from the lumen of the small intestine into the enterocytes by active transport. A portion thereof is metabolized within the enterocytes and the rest is transported via the portal circulation to the liver to participate in protein biosynthesis or to be metabolized to L-alpha-aminoadipic acid semialdehyde, which is further metabolized to acetoacetyl-CoA. L-Lysine that is not metabolized in the liver is transported to the various tissues of the body (Cynober, L. A. Metabolic and therapeutic aspects of amino acids in clinical nutrition. 2nd ed. CRC Press LLC, Boca Raton, USA (2003)).

Lysine has many functions. It serves as a precursor for glycogen, glucose and lipids or it serves directly for energy production. It is concentrated in muscles, promotes bone growth, and enhances the formation of collagen (Voet, D. and Voet, J. G., Biochemistry. 3th ed. John Wiley and Sons Inc., New York (2004)). Collagen is the basic matrix of the connective tissues (see before), skin, cartilage, and bone. Lysine deficiency may contribute to reduced growth and immunity, impaired sperm health, along with an increase in urinary calcium. This latter fact suggested that adequate lysine may help prevent osteoporosis through better absorption and deposition of calcium (Flodin, N. W., J. Am. Coll. Nutr. 16:7-21 (1997)). L-Lysine became popular as a nutritional supplement when some studies showed that it can decrease the recurrence rate of herpes simplex infections and in stimulating growth hormone secretion (see below).

Recommended dosages, side effects, and contraindications: Supplemental doses of the above discussed amino acids are largely variable depending on the conditions to be treated. However, the normal dietary needs of the essential amino acid lysine for average human are estimated to be 0.75-1 g daily to avoid deficiency problems. Doses of arginine used in clinical research have varied considerably, from as little as 0.5 g per day for oligospermia to as much as 30 g per day for cancer, preeclampsia, and premature uterine contractions. Significant adverse effects have not been reported on the supplementation of the discussed amino acids throughout this article. However, many of the mentioned clinical applications need to be confirmed with more controlled as well as long-term studies. This article summarizes only the positive reports on the effects of these amino acids, whereas, contra-reports also exist where many of these effects could not be confirmed (for complete reviews see Flodin, N. W., J. Am. Coll. Nutr. 16:7-21 (1997); Appleton, J., Altern. Med. Rev. 7:512-522 (2002); and Dean, W. and Pryor, K., Growth hormone: amino acids as GH secretagogues—a review of the literature. Vit. Res. News; available at the website vrp.com (2001)).

Dipeptides and mixtures of aspartate, arginine and lysine in clinical therapy: Aspartate and arginine are favorably administrated together as dipeptides or in mixtures to provide higher bioavailability for both amino acids and thereby increase their effectiveness in lower doses. The administration of both amino acids was investigated during several studies for the treatment of different physiological disorders. In general, both amino acids can be administrated in the dipeptide form for all the above-mentioned applications for the free amino acids. The following section summarizes though, the research results reported specifically on the combined administration form. These reports emerged from studies on wound therapy, on endocrine conditions as the GH secretary disorders and enhancing athletic performance, or on genitourinary conditions including erectile dysfunction and male and female infertility.

Arginine-aspartate was tested clinically in 1965 for the first time against physical and psychic asthenia (Duruy, A. and Baujat, J. P., Vie. Med. Int. 9:1589 (1965)) and the positive effect was later confirmed (Duruy, A., Med. Int. 1:203 (1966)). Other studies showed that long-term administration of arginine-aspartate improves aerobic energy metabolism and performance (Sellier, J., Rev. Med. Toulouse 5:879 (1979); Schmid, P. et al., Leistungssport 10:486-495 (1980)). Arginine-aspartate supplementation enhanced wound healing and the immune functions of T-cells (Barbul, A. et al., Surgery 108:331-336 (1990)). Other positive effects were also reported on athletic performance; for example on lipid metabolism, where arginine intake for only 2 weeks caused sinking in the total cholesterol concentrations (Hurson, M. et al., J. Parenter. Enteral Nutr. 19:227-230 (1995)). Thus, L-Arginine-L-Aspartate (Sargenor®) is widely used by athletes and patients to increase training effects as well as exercise tolerance. Impressive effects on enduring performance in this field have been reported after prolonged intake of L-Arginine-L-Aspartate causing decreased blood lactate concentrations and heart rates during submaximal exercise and increased oxygen uptake with workload increments (Schmid, P. et al., Leistungssport 10:486-495 (1980); Sellier, J., Rev. Med. Toulouse 5:879 (1979); Burtscher, M. et al., J. Sports. Sci. Med. 4:314-322 (2005)).

Dietary supplementation with 30 g/d arginine aspartate for 2 weeks to healthy elderly human volunteers enhanced wound collagen accumulation significantly (Witte, M. B. and Barbul. A., Wound Rep. Reg. 11:419-423 (2003)). When 250 mg/kg/day of oral arginine aspartate were administrated to five healthy subjects aged 20 to 35 for seven days, a 60% rise in GH occurred during slow wave sleep (Besset, A. et al., Acta Endocrinol. 99:18-23 (1982)). Another group of researchers achieved promising results after treating 12 normal adults with one large dose (37.5 g) of oral arginine aspartate, which caused small but significant release of serum hGH (Elsair 1987). This made arginine aspartate interesting for body builders wishing to take advantage of the anabolic properties of the hGH (Macintyre, J. G., Sports Med. 4:129-142 (1987)).

Orally administered L-Arginine-L-Aspartate was also reported to induce positive effects in treatment of some types of cancer. For example it induced antimetastatic effects on salivary adenoid cystic carcinoma in mice, accompanied by inhibited pulmonary metastatic foci formation and prolonged survival. Further in vitro and in vivo experiments confirmed these results (Li, F. et al., Chin. J. Stomatol. 36:464-466 (2001); Li, F. et al., Chin. J. Stomatol. 37:87-89 (2002); Appleton, J., Altern. Med. Rev. 7:512-522 (2002)).

In the field of dental health, plaque, the closely adhering spongy organic material on teeth surfaces, was found to accept peptides of certain size and shape within its matrix. Furthermore, peptides of 2-4 amino acid units, one or more of which is arginine, were shown to be stored in plaque protected from dilution and to effectively restore mouth pH to a non-carious level (6.1 or higher). It was further shown that these oligomers are effective even when provided simultaneously with carbohydrates. This suggested the inclusion of such peptides in common dental products such as toothpastes and chewing gum (Kleinberg, I., U.S. Pat. No. 4,225,579 (1980)).

L-Arginine-L-Aspartate was also applied for the treatment of genitourinary disorders. ED is common in 25% of males aged 45-70 years with moderate erectile dysfunction and in 10% with severe erectile dysfunction (Kernohan, A. F. B. et al., Br. J. Clin. Pharmacol. 59:85-93 (2004)). Recently, "L-arginyl aspartate" was used as a component of several pharmaceuticals for the treatment of male ED such as Prelox® (Lamm, S. et al., Eur. Bull. Drug Res. 11:29-37 (2003)). Clinical studies on the components of Prelox® showed improved erectile function in 5% and 92% of forty men with ED after receiving 3 doses of 1 g of "L-arginyl aspartate" (Sargenor®) (1.7 g arginine daily) alone, or together with Pycnogenol® (stimulates NOS secretion), respectively (Stanislavov, R. and Nikolova, V., J. Sex Marit. Ther. 29:207-213 (2003)). During a long term study, fifty men aged between 45 and 60 having ED, lowered volume of semen, reduced sperm motility and morphological abnormalities of sperms, were treated first with Sargenor® alone for 1 month. 10% of these men experienced normal erection. After addition of Pycnogenol® to the treatment for the second month, the percentage of men with normal erection increased to 80%. The treatment was continued for a period of one year during which sperm quality was significantly improved and 42% of the couples achieved pregnancy (Stanislavov, R. and Nikolova, V., Int. J. Impot. Res. 14(4):565 (2002); Lamm, S. et al., Eur. Bull. Drug Res. 11:29-37 (2003)). The later observation confirmed previous studies on the use of arginine-aspartate where several months supplementation increased sperm count and quality (Tanimura, J., Bull. Osaka Med. School 13:84-89 (1967); Schellen, T. M. and Declerq, J. A., Dermatol. Monatsschr. 164:578-80 (1978); De-Aloysio, D. et al., Acta Eur. Fertil. 13:133-167 (1982)) and improved fertility (Schacter, A. et al., J. Urol. 110:311-13 (1973); Schacter, A. et al., Int. J. Gynaecol. Obstet. 11:206-209 (1973)).

Clinical reports on dipeptides consisting of aspartate and lysine hardly exist because this dipeptide is not available in large amounts. However, this dipeptide form of lysine could be effective in the application fields known for free lysine or its salts (see before), in people with genetic deficiency in lysine transporters, or simply as a food additive, with higher bioavailability than free lysine, for human and animals. Arginine and lysine work synergistically to release growth hormone (GH) (Suminski, R. R. et al., Int. J. Sport Nutr. 7:48-60 (1997)) and their concentrations are very important in human and animal nutrition (Ahmed, I. and Khan, M. A., Aquacult. Nutr. 10:217-225 (2004)). Low lysine: arginine ratios have hypocholesterolemic effect (Sánchez, A. et al., Nutr. 38:229-238 (1998)) and thus, patents were made for protein mixtures with Arg:Lys ratio of at least 5.5:1 to be used for patients with cardiovascular diseases (Radha, C. et al., U.S. Pat. No. 7,091, 001 (2006)). In contrast, and because proteins of herpes simplex virus are rich in L-Arginine, high lysine to arginine ratio in the diet is known to help reducing viral replication, healing times, and the cytopathogenicity during outbreaks (Griffith, R. S. et al., Dermatologica 156(5): 257-267 (1978)). Thus, in herpes prevention and treatment, avoiding arginine-rich foods and eating more lysine-rich foods is suggested to be helpful.

Recent research has suggested that therapy using L-Lysine and L-Arginine together is useful and possibly even better than the arginine/ornithine combination in stimulating hGH, and thereby improving muscle building, weight gain, and immune support. In 15 healthy male subjects aged 15 to 20 years old, 1.2 g of arginine pyroglutamate combined with L-Lysine hydrochloride significantly elevated GH levels from two to eight times after consuming the amino acid mixture (Isidori, A. et al., Curr. Med. Res. Opin. 7:475-481 (1981)). Another study indicated that ingestion of 1.5 g arginine and 1.5 g lysine ingested under resting conditions causes an acute increase in GH secretion (Suminski, R. R. et al., Int. J. Sport Nutr. 7:48-60 (1997)).

To simulate the natural conditions inside the digestive tracts, the prepared gut "juice" was used as inoculum and as nutritional supplement in anaerobic Hungate tubes containing CGP. The complete degradation of CGP in all tubes indicates that CGP can be easily degraded in such anaerobic milieu like that of the digestive tracts. This was also confirmed by the short degradation periods which are analogous to those observed previously for strict and facultative anaerobic CGP degrading bacteria (Obst, M. et al., Appl. Environ. Microbiol. 71:3642-3652 (2005); Sallam, A. et al., Submitted for publication (2008)).

During this study, and for the first time the wide spread of CGP degrading bacteria in animal, avian and fish digestive tracts is demonstrated (Table 1, 2). The morphological diversity between the CGP degrading colonies observed during purification procedures and later between the resulting axenic culture was also shown by previous studies on environmental samples, which showed wide spread of CGP degraders among prokaryotes (Table 2). On the other hand, the capability to degrade CGP seems to be more spread among species of particular genera; investigations on extracellular CGP degradation until today show that CGP degraders are wide spread among the genera *Pseudomonas* and *Bacillus* (Obst, M. et al., J. Biol. Chem. 277:25096-25105 (2002); Obst, M. et al., Biomacromolecules 5:153-161 (2004); Sallam, A. et al., Submitted for publication (2008), this study). However, this might be associated with the applied laboratory conditions which might have favorized these bacteria or simply because of the predominance of these bacterial genera in nature. Additionally, many CGP degrading bacteria, unlike strains of genera *Pseudomonas* and *Bacillus*, are extremely hard to be brought to axenic cultures without loosing the ability to degrade CGP (Obst, M. et al., Appl. Environ. Microbiol. 71:3642-3652 (2005); Krug, A., Diplom thesis, Institut für Molekulare Mikrobiologie and Biotechnologie, Westfälische Wilhelms-Universität, Münster, Germany (2001)) and are usually disregarded.

Partial CGP degradation was observed only for axenic cultures, under anaerobic conditions, and for only 8 strains from 46 strains that degraded CGP anaerobically. A plausible reason for this is the lack of natural interactions between these strains and others as in their natural milieu, which leads often to the accumulation or exhaustion of limiting or necessary substances, respectively. This is in accordance with previous observations on the strict anaerobic endospore former *S. hongkongensis* strain KI where growth and CGP utilization were largely enhanced in the presence of its co-isolate *Citrobacter amalonaticus* strain G (Obst, M. et al., Appl. Environ. Microbiol. 71:3642-3652 (2005)).

Among the eight identified isolates, several strains showed capability of anaerobic CGP degradation although they belong to genera known to be aerobic like *Bacillus* or *Pseudomonas*. However, strains of *B. subtilis* and *B. megaterium* are known to grow anaerobically and some are known to reduce nitrate (Glaser, P. et al., J. Bacteriol. 177:1112-1115 (1995)). Similarly, anaerobic growth and nitrate reduction of members of genus *Pseudomonas* is well investigated (Sallam, A. et al., Submitted for publication (2008)). Species of *Micromonospora*, *Streptomyces* and *Brevibacillus* are also known to be facultative anaerobic (Cochrane, V. W., Annu. Rev. Microbiol. 15:1-26 (1961); Borodina, I. et al., Genome Res. 15:820-829 (2005); Baek, S. H. et al., Int. J. Syst. Evol. Microbiol. 56:2665-2669 (2006)). In general, the recent investigations on CGP degradation point toward a wide spread of CGP degrading bacteria among the facultative anaerobes.

Although CGP and its dipeptides are simple proteinacious substances of natural origin, clinical studies are required to bring these substances to the market. The wide spread of CGP degrading bacteria in gut flora of each of the mammalian, avian or fish tested during this work, provides the first evidence that orally administrated CGP would be fast and easily degraded at least microbially. The isolation of such bacteria from the lower digestive tract of different animals and birds (Table 1) indicates that if the digestion of CGP was not completed in the upper digestive tract, it would possibly continue in the lower part.

HPLC analysis reveled that dipeptides were the degradation products of CGP by all 62 isolates. No dipeptide oligomers of higher order like ($\beta$-Asp-Arg)$_2$ tetrapeptides were produced from CGP. This is in accordance with the effect of the CGPases from *P. anguilliseptica* strain BI (Obst, M. et al., J. Biol. Chem. 277:25096-25105 (2002), *S. hongkongensis* strain KI (Obst, M. et al., Appl. Environ. Microbiol. 71:3642-3652 (2005)) and *P. alcaligenes* strain DIP1 (Sallam, A. et al., Submitted for publication (2008)). Only in case of *Bacillus megaterium* strain BAC19, such oligomers of higher order were detected (Obst, M. et al., Biomacromolecules 5:153-161 (2004)). *Spirulina* is known for centuries for its nutritional and therapeutic effects and is consumed as food in many countries until today. The protein content of *Spirulina* is known to reach over 60% (Narasimha, D. L. R. et al., J. Sci. Food Agric. 33:456-460 (1982)). The presence of CGP in market-available products of *Spirulina platensis* indicates that CGP might participate in the well-being effect of regular consumption of *Spirulina*. However, the determined CGP contents in the analyzed samples varied largely and were relatively low. This is in agreement with previous studies on CGP accumulation in cyanobacteria, where the accumulation of CGP is known to be affected by many factors and to vary accordingly (Elbahloul, Y. et al., Appl. Environ. Microbiol. 71:7759-7767 (2005)). Moreover, the market available *Spirulina* products surely have gone through numerous clinical and toxicological tests before they were licensed for commercialization. This indicates that extracted CGP and CGP-dipeptides would induce no toxic effects if ingested orally. Moreover, CGP dipeptides are usually uptaken and utilized for growth in bacteria, and showed no bacteriostatic or bactericidal effects during targeted investigations (data not shown). In general, the known effects and applications of *Spirulina* are very similar to those proved for arginine, which suggests that a part of these effects may be actually due to its arginine content (about 6%) including that of CGP.

Bacteria possess three peptide transport systems, two, oligopeptide permease (Opp) and dipeptide permeases (Dpp), belonging to the large family of ABC (ATP-Binding Cassette) transporter and one for di- and tripeptides belonging to the PTR (Peptide TRansporter) family. Only the latter system is conserved in higher eukaryotic organisms starting with yeast (Daniel, H. et al., Physiology 21:93-102 (2006)). In mammals, the carrier system for di- and tripeptides PEPT (SLC15 family) includes 2 variants; the intestinal PEPT1 (SLC15A1) and the renal isoform PEPT2 (SLC15A2). They transport almost all possible di- and tripeptides in stereoselective manner with a preference for L-$\alpha$ amino acids and their derivatives. Peptides containing solely D- or four or more amino acids are not accepted. Because PEPT1 has a prominent expression throughout the small intestine and due to its high transport capacity, all drug substrates of PEPT1 have an excellent oral availability, and thus, PEPT1 has become a prime target for drug delivery (Daniel, H. et al., Physiology 21:93-102 (2006)). The constituting L-amino acids of CGP dipeptides, Asp-Arg and Asp-Lys (recombinant CGP) are linked via α-β peptide bonds. This type of bond and the stereo-structure of CGP dipeptides assume strongly that they would act as substrates for PEPT system, and can be transported from the lumen of the mammalian gut when they are ingested. Thus, the use of CGP and/or the dipeptides thereof would be an ideal approach for the oral administration of the constituting amino acids as therapeutic and/or nutritional agents.

The nutritional and the clinical values of amino acids are known for centuries including those which constitute CGP such as aspartate, arginine and lysine and those which can be still integrated into its structure like citrulline, ornithine, canavanine or glutamate. Synthetic oligomer combinations of these amino acids were proven to have higher bioavailability than free amino acids and thus were often investigated and applied in nutrition and therapy (see before). CGP represents an ideal natural source for such oligomers which can be expected to be more effective in lower doses than their constituting amino acids in the free form. Thus, absorption, safety, and the effect of CGP and its dipeptides are currently under investigation. Moreover, studies on integrating other amino acids in CGP showed promising results (data not shown). The resulting dipeptides could be applied in several therapeutic fields, for instance, aspartate-ornithine in the treatment of liver diseases (Kircheis, G. et al., Hepatology 25:1351-1360 (1997)). Consequently, any future alterations in CGP structure would increase the range of CGP dipeptides and subsequently extend their application scope as therapeutics and/or nutritional supplements.

A triphasic process was established for the large scale production of β-dipeptides from cyanophycin (CGP). Phase I is based on an optimized acid extraction method for the technical isolation of CGP from biomass, a total of 704 g pure CGP were obtained and structurally contained aspartate, arginine, and little lysine. Phase II represents the fermentative production of an extracellular CGPase (CphE), the enzyme was produced from Pseudomonas alcaligenes strain DIP1 at 500 l scale and using 1 g/l citrate as a sole substrate, 17.5 g crude protein powder were gained and showed high degradation activity on CGP. Phase III comprises the degradation of CGP via CphE, 250 g of CGP were degraded to β-aspartate-arginine and β-aspartate-lysine dipeptides with a purity grade of over 99% (TLC, HPLC). The overall efficiency of phase III was 91%, while 78% (wt/wt) of the used CphE powder were recovered and showed sustained activity on CGP. The established process depends on materials and equipments with industrial standards and applicable as it is for every desired scale.

Strains of *P. alcaligenes* including strain DIP1 are known to grow on a wide range of substrates and to require minimal amounts thereof. The high enzyme productivity of such strains was also a main reason for their application in the fermentative production of extracellular lipases (WO 95/30744; Gerritse, G. et al., Appl. Environ. Microbiol. 64:2644-2651 (1998); Moore, E. R. B. et al. Mai 1999. *Pseudomonas*: Nonmedical. In Moore et al. (ed.), The Prokaryotes: An Evolving Electronic Resource for the Microbiological Community, 3$^{rd}$ edition, release 3.0, Springer-Verlag, New York)). These characteristics, in addition to the high stability and activity of the CGPase from strain DIP1 (Sallam, A., and A. Steinbüchel. 2007b.

Anaerobic and aerobic degradation of cyanophycin by the denitrifying bacterium *Pseudomonas alcaligenes* strain DIP1-Role of other three co-isolates in the mixed bacterial consortium. Submitted for publishing), were the main factors to consider this strain ideal for the designed technical process.

Before the final triphasic process was created, several trials were carried out to reach the same goal by cultivating strain DIP1 directly on CGP, however, that strategy was less effective due to the fast consume of CGP-dipeptides by the growing cells, this problem was avoided during the defined procedures of the triphasic process where cells of strain DIP1 are excluded. Furthermore, the dipeptide solutions obtained by the direct cultivation have large volumes and therefore extremely hard to handle, also the presence of small proteins and salts in the resulting dipeptide solutions represented another disadvantage of that strategy. In contrast, the degraded concentrations of CGP by the triphasic process as well as the time for degradation are entirely controllable. Thereby, the out-coming dipeptide solutions are restricted to small and easy to handle volumes. The highest tested concentration (50 g/l) is one of the aspects that can be still optimized for future applications rendering the process to be economically more effective.

Economic factors are generally of great importance for technical processes, therefore, the obtained results during medium optimization and substrate utilization were found satisfactory, citrate which is a cheap substrate in technical quantities, and which was ideal for the applied strain as a sole substrate, was previously applied for the fermentative production of extracellular lipases (Gerritse, G. et al., Appl. Environ. Microbiol. 64:2644-2651 (1998)), however, the need for an optimized medium for the production phase of crude CphE (phase II) emerged through the necessity of accurate monitoring of the turbidity grade during fermentation, especially during the induction and degradation phase. Previous experiences with experimental CGP-degradation showed that unclear media as well as strong growth of cells can be misleading, besides, better growth of cells did not essentially mean higher production of extracellular CGPases (unpublished data).

The CGP acid-extraction method of Frey, K. M. et al., Appl. Environ. Microbiol. 68: 3377-3384 (2002), which was successfully applied during previous studies, was optimized to become suitable for the isolation of pure CGP from any technical amounts of biomass. The most effective change to the original method was the sterile-filtration step of the solved CGP, this procedure guaranteed for the complete removal of any cell debris that are not soluble in diluted HCl. In contrast, the increased purification steps, with diluted acid and water, may have unnecessarily increased the loss of CGP, which explains the difference between the obtained CGP and the expected amount. The loss of CGP as well as the time needed for its extraction can be minimized by centrifugating CGP instead of leaving it to settle at 4° C.

Alternatively, the overall productivity of this extraction method can be drastically increased if an effective instrument such as cross flow is applied, in this case, 2 cassettes with 2 different COPs are required; one larger and the other smaller than the molecular size of the CGP to be isolated, the 2 cassettes are to be applied for the alternating filtration of CGP in the solved and the precipitated states of CGP, respectively. However, the relatively high prices and the yet limited life of such ultrafiltration cassettes leave their application to be a matter of costs.

During the fermentative production of the crude CphE (phase II), the induction with CGP was employed within the stationary phase to guarantee for a maximum production of CphE, and to exclusively refer the turbidity changes to the amount of CGP in the medium.

The pH of the medium increased to exceed the tolerated range (pH 6.9-7.5) and was controlled by the addition of HCl, this is most probably due to the release of ammonia by cells of strain *P. alcaligenes* DIP1. A similar physiological behavior was also documented for this strain during previous investigations on CGP degradation (Sallam, A., and A. Steinbüchel. 2007b. Anaerobic and aerobic degradation of cyanophycin by the denitrifying bacterium *Pseudomonas alcaligenes* strain DIP1-Role of other three co-isolates in the mixed bacterial consortium. Submitted for publishing).

The identical purity grade of the resulting CGP-dipeptides, before and after the different tested filtration systems, is clearly due to the initial lack of impurities in the original dipeptide solution. This represents another advantage for applying a defined enzymatic process in comparison to the direct cultivation strategies with bacterial cells. On the other hand, the quantitative loss of dipeptides due to filtration was expected and unfortunately inevitable; several general factors are known to cause such losses including; filter material, cut off points, and/or the characteristics of the filtered substance itself. This explains also the loss of 9% of CGP and 22% of crude CphE during the degradation phase (phase III). Besides, only new filter-membranes were tested (0.5-10 kDa. COPs), and thereby the lost amounts of CGP-dipeptides most probably attached to the membranes surfaces until saturation.

Even though, the overall process affectivity of 91% is quite high, several aspects can be even more improved and thus are under optimization, these aspects include higher productivity of crude CphE, possible technical purification strategies for CphE, and more effective conditions for the degradation phase (unpublished data). The commercial value of CGP-dipeptides are directly related to the production costs of CGP itself, though, over the last few years, the production of CGP was intensively investigated and optimized using several bacterial strains, thereby, mounting CGP contents are being achieved using new and more suitable economic substrates, these developments seem to move fast in the direction of commercial CGP production (see above), this way was also needed by other known bacterial poly(amino acids) such as poly(glutamic acid) and poly(ε-lysine) to become commercialized for technical as well as food applications (reviewed by Oppermann-Sanio F. B. et al., Naturwissenschaften 89:11-22 (2002); Obst, M. et al., Biomacromolecules 5:1166-1176 (2004)). Until then, the biomedical value of CGP-dipeptides may in fact provide a balanced relation to the actual production costs of CGP. Therefore, the biomedical effects of CGP-dipeptides are currently under investigation (Sallam, A., and A. Steinbüchel. 2007c. Potential of cyanophycin and its β-dipeptides as possible additives in therapy, food and feed industries).

A previously applied biotechnological process for the large scale production of β-dipeptides from cyanophycin (CGP) was optimized; the original process consisted of three phases; phase I: large scale extraction of pure CGP from biomass, phase II: large scale production of crude cyanophycinase ($CphE_{al}$) from *Pseudomonas alcaligenes* strain DIP1, phase III: CGP degradation to its dipeptides. Optimal cultivation conditions were determined for the second phase; 2 g l$^{-1}$ citrate, pH 6.5 and cultivation temperature of 37° C. Optimal concentration for CGP as inductor for $CphE_{al}$ was 50 g l$^{-1}$ which represents ⅕ of the concentration applied previously. Maximum enzyme concentrations were obtained 5 h after induction. The same concentration of CGP-dipeptides showed similar induction efficiency after only 3 h. Also an optimum of 4 g l$^{-1}$ L-aspartate induced $CphE_{al}$, however, with ⅓ efficiency compared to CGP. $CphE_{al}$ was purified via substrate-specific binding on CGP. The purified enzyme was characterized and came out to be a serine protease with maximum activity at 50° C. and pH 7-8.5. Conditions for phase III of the original process (CGP degradation); 50 g CGP, 10 g l$^{-1}$ crude $CphE_{al}$ and incubation for 10 h at 30° C. could be optimized to; 100 g l$^{-1}$ CGP, 10 g l$^{-1}$ crude $CphE_{al}$ and incubation for only 4 h at 50° C. CGP was degraded to β-aspartate-arginine and β-aspartate-lysine dipeptides with purity grade of over 99% (HPLC). These optimizations rendered the technical process more cost, time and effort effective. Prior to the production of CGP on protamylasse at 500-l scale fermentation. Pre-tests on the available charge of protamylasse revealed that 7% (vol/vol) was optimum for CGP production, however, during the previous study of Elbahloul, Y. et al., Appl. Environ. Microbiol. 71:7759-7767 (2005) on a former charge of protamylasse, the optimum concentration was found to be 6% (vol/vol). This is due to that protamylasse, which is a residual compound of industrial starch production, is a complex medium with a composition that can vary from charge to charge and thus must be adjusted before application as cultivation medium.

During fermentation, and after the first 6 h, temperature was elevated to 37° C. in order to inactivate the temperature-sensitive λ-repressor (c1857) and thereby enable the induction of CGP-synthetase (CphA) gene. At this time point, cells of recombinant *E. coli* strain were already for two h in the exponential growth phase. This fermentation course was proved to be optimum for induction of the CGP-synthetase as well as for maximum intracellular accumulation of CGP (Frey, K. M. et al., Appl. Environ. Microbiol. 68:3377-3384 (2002)).

Also after 6 h of fermentation, turbidity of the medium showed a sudden jump with parallel increase in the automatically controlled stirring. This can be explained by the decrease of oxygen in the medium due to strong cell growth in addition to the temperature elevation to 37° C. Obviously, oxygen content in the medium became lower than the pre-adjusted minimum and caused the automatic increase of stirring, this in turn led to high formation of foam and air bubbles and subsequently to false $OD_{850\,nm}$ values. The manual addition of antifoam emulsion caused a fast fall of turbidity to reach the normal level.

The fermentation was terminated when maximum CGP accumulation in the cells was microscopically estimated (after 15 h). However, later analysis of fermentation samples indicated that a better harvesting time would have been after 13 h of incubation. At that time point, CGP content was about 13% (wt/wt of CDM) while after 15 h it declined to 10% (wt/wt of CDM). This lost was clearly due to the inaccuracy of the microscopic estimation of CGP content which was the only possible method during fermentation. Moreover, the decrease of CGP content is most probably due to plasmid losses that occurred with time during incubation (Elbahloul, Y. et al., Appl. Environ. Microbiol. 71:7759-7767 (2005)). After extraction and purification of the polymer, HPLC analysis revealed a high purity grade for CGP and that it consists of the three amino acids aspartate (47.7 mol %), arginine (45.6 mol %) and lysine (6.8 mol %). SDS-PAGE showed that CGP has a molecular size of 25-30 kDa. These characteristics are in strong agreement with those of previously produced CGP by the same strain on several media (Frey, K. M. et al., Appl. Environ. Microbiol. 68:3377-3384 (2002); Elbahloul, Y. et al., Appl. Environ. Microbiol. 71:7759-7767 (2005)).

Recently, a simple mineral salt medium (SM-Medium) with 1 g l$^{-1}$ citrate was applied for the large scale production of CphE$_{al}$ from *P. alcaligenes* strain DIP1. This medium was favorable due to its simple and cost-saving composition as well as due to its suitability for the used strain (Sallam, A., and A. Steinbüchel. 2008b. Biotechnological process for the technical production of β-dipeptides from cyanophycin. Under preparation). However, during this study, Even though the optimal citrate concentration for growth was 6 g l$^{-1}$, no CphE$_{al}$ was produced in such cultivations. Maximum production of CphE$_{al}$ occurred in cultures grown on 2 g citrate; this indicated that the enzyme is induced only under substrate limitation. Other experiments for temperature and pH optima indicated 37° C. and pH range of 5.5-7.5 with an optimum at 6.5 to be optimal for strain DIP1 as well as for the production of CphE$_{al}$. This enhanced the efficiency of the production process which was initially applied on 1 g l$^{-1}$ citrate, pH 7.5 and an incubation temperature of 30° C. (Sallam, A., and A. Steinbüchel. 2008b. Biotechnological process for the technical production of β-dipeptides from cyanophycin. Under preparation).

Extended investigations on CphE$_{al}$ induction revealed that only a fifth (50 mg l$^{-1}$) of the previously applied CGP concentration (250 mg l$^{-1}$) was sufficient to render the same effect. Also CGP-dipeptides were sufficient in the same concentration (50 mg l$^{-1}$) to induce CphE$_{al}$ with the same efficiency. However, the shorter incubation period (3 h) required until harvesting for cultures induced with dipeptides indicates that CGP-dipeptides are the actual inductors for CphE$_{al}$ and not CGP itself. Additionally, aspartate was a successful inducer for CphE$_{al}$, but other than CGP-dipeptides, a concentration of 4 g l$^{-1}$ and a further incubation period of 5 h were required for maximum CphE$_{al}$ production, this represented a CphE$_{al}$ production efficiency of only one third of that of CGP or the dipeptides thereof. Thus, choosing the inductor in future applications remains case and cost dependant.

The third phase of the original process (large scale degradation of CGP via crude CphE$_{al}$) was found to be much more effective at 50° C. instead of 30° C. This optimization rendered much higher concentrations of CGP (up to 100 g l$^{-1}$) to be easily degradable in only a forth of the degradation time at 30° C. This is in accordance with the Van 't Hoff equation where velocity of a reaction is doubled by a temperature increase of 10 kelvin (10° C.). Also volumes of degradation mixtures and the risk of their contamination are minimized at such elevated temperature. At both incubation temperatures 30° C. and 50° C., degradation time showed a collinear increase with decreasing concentrations of crude CphE$_{al}$ and with increasing CGP concentrations. Thus, the resulting formula can be helpful to apply optimum degradation parameters during future process applications. Because the efficiency of the degradation phase is much higher at 50° C., the formula was calculated for application at 50° C. and is subsequently suitable for CGP concentrations up to 100 g l$^{-1}$.

Organic solvents or ammonium sulfate precipitation provided weak purification effect and low enzyme recovery rates. On the contrary, the developed procedure by specific binding to CGP proved to be highly effective and has the advantage of separating CphE$_{al}$ from other proteins in crude solutions using one substance (CGP). The purification method ends with the degradation of the CGP matrix to its dipeptides; these are in the same time the valuable end products of the process and thus can be directed further to the main production stream (no material loss). The purification method is easy to up-scale and to be integrated in future process applications if desired.

Two formulas were created to increase the efficiency of the second phase of the original process (large scale production of crude CphE$_{al}$) and the possible purification thereof. The first formula (s.a.) is based on the photometrical analysis of CphE$_{al}$ and enables fast determination of CphE$_{al}$ content in crude supernatants. The determined concentration of CphE$_{al}$ can be then integrated into the second formula to estimate the required amount of CGP to bind, and thereby purify, the complete content of CphE$_{al}$ in the supernatant. This scheme provides a trustable instrument for future production charges of crude CphE$_{al}$ which might differ largely in their protein composition.

During experiments for substrate-specificity of the purified CphE$_{al}$, not only CGP was degraded but also BSA, however, to lower extent. This indicates that the CGPase from *P. alcaligenes* strain DIP1 might be less specific than the previously characterized CphE$_{Pa}$ and CphE$_{Bm}$ from *P. anguilliseptica* strain B1 and *Bacillus megaterium* strain BAC19, respectively. A more plausible explanation for this unspecific effect is the presence of few other proteins in the purified enzyme solution. Even though these proteins were visible in SDS-PAGE only in highly concentrated samples and with intensive silver nitrate staining; only a minimum amount of a non-specific protease might produce such an effect on the tested substrates other than CGP.

CphE$_{al}$ from *P. alcaligenes* strain DIP1 was largely inhibited by both serine-protease inhibitors Pefabloc® and PMSF. This indicates that this CGPase most probably belongs to serine-type proteases. This is in agreement with the results for the previously characterized CGPases; CphB, CphE$_{Pa}$ and CphE$_{Bm}$. Moreover, CphE$_{al}$ was totally inhibited by the tryptophan oxidizer N-bromosuccinimide that shows that a tryptophan residue might be involved in the catalytic mechanism of the enzyme. Also this points out high similarity between CphE$_{al}$ and the extracellular CphE$_{Pa}$ and CphE$_{Bm}$. CphE$_{al}$ samples which were treated with Leupeptin or EDTA showed no activity inhibition on CGP-overlay agar plates, however, HPLC analysis of samples treated with EDTA showed inhibition of the CGPase of about 75%. This is due to formation of large amounts of precipitates during OPA-derivatization and not due to enzyme inhibition (Obst, M. et al., J. Biol. Chem. 277:25096-25105 (2002); Obst, M. et al., Biomacromolecules 5:153-161 (2004)). Biochemical characteristics of CphE$_{al}$ of *P. alcaligenes* strain DIP1 in comparison to the previously characterized CphB, CphE$_{Pa}$ and CphE$_{Bm}$ from *Synechocystis* sp. PCC6803, *P. anguilliseptica* strain B1 and *Bacillus megaterium* strain BAC19, respectively, are demonstrated in table 3. Although several characteristics of the purified CphE$_{al}$ were relatively similar to those from CphE$_{Pa}$ and CphE$_{Bm}$, some relevant differences can be observed such as molecular size and optimum temperature. The latter was 50° C. for CphE$_{al}$, which is the highest temperature optimum for all known CGPases and thereby provides a great benefit for applying this enzyme in the pure as well as in the crude form. The purified enzyme showed an optimum pH range of 7-8.5 with an optimum of 8.5 which shifts from that determined for the crude enzyme (5.5-7.5 with an optimum of 6.5). This is most probably due to the presence of many other proteins in the crude extract representing a complex milieu; interactions within such milieu may in turn affect the structure and/or properties of the CGPase. The cell line *Pseudomonas alcaligenes* DIP1 was deposited on Jun. 10, 2008 at the DMSZ, Deutsche Sammlung von Mikroorganismen and Zellkulturen GmbH, Mascheroder Weg 1b, 38124 Braunschweig, Germany under deposition No. DSM 21533.

The invention is further described in the following examples, which are however, not to be construed as limiting the invention.

EXAMPLES

Materials and Methods

Sampling and Samples Preparation:

The gut flora samples were collected from freshly slaughtered healthy exemplars (Table 1). Except for ruminants (feeding history could not be determined), all chosen animals, birds and fishes were at least partially free living or free grazing. Samples were collected from several sites (Table 1) along the digestive tract of each source animal by completely filling 50 ml sterile falcon tubes, which were kept at 4° C. until use. Samples were diluted (Table 1) with sterile normal saline and then filtered (folded filter, Schleicher & Schuell, Dassel, Germany) from solid materials under sterile conditions. Faecal samples were chopped in sterile saline and filtered as described above.

Media:

For enrichment of bacteria capable of CGP degradation under anaerobic conditions, the following basal medium (BM) was applied: 1.0 g $NH_4Cl$, 3.0 g $KH_2PO_4$, 3.0 g $K_2HPO_4$, 0.1 g KCl, 0.5 g $MgCl_2.6H_2O$, 0.1 g $CaCl_2.2H_2O$, 0.5 g NaCl, 0.5 g cysteine-HCl, 0.5 g yeast extract (unless otherwise indicated in text), 10 ml of SL10 trace elements solution, and 1 mg of resazurin per l of distilled water. pH was adjusted to 7.0 with KOH. The medium was boiled, and after $Na_2S.9H_2O$ had been added to a final concentration of 0.04% (wt/vol), it was immediately transferred to an anaerobic chamber (Type A—manual air lock; Coy Inc., Grass Lake, Mich., USA) containing an atmosphere of Formier gas ($N_2$: $H_2$, 95:5%, vol/vol). After cooling to room temperature, 10 ml aliquots were dispensed into Hungate tubes, sealed, removed from the anaerobic chamber and subsequently sterilized by autoclaving at 121° C. for 20 min. Aerobic cultivations were conducted in 100 ml Klett flasks containing BM medium lacking the reducing agents cysteine-HCl and $Na_2S.9H_2O$.

Luria Bertani (LB) medium (Sambrook, J. et al., Molecular cloning: a Laboratory Manual, 2nd ed. Cold Spring Harbor, N.Y.: Cold Spring Harbour Laboratory (1989)) was used for the purification of CGP degrading bacteria and for maintenance of viable cultures.

For the isolation of strain P. alcaligenes DIP1 a modified mineral medium of Dufresne, A. et al., Macromolecules 31:6426-6433 (1998), was used (SM-medium); 1.0 g $NH_4Cl$, 5.0 g $KH_2PO_4$, 1 g $MgSO_4.7H_2O$ (sterilized and added separately) and 10 ml of trace elements stalk solution, per l tap water. The trace elements stock solution contained nitrilotriacetic acid (70 mM, pH 6.5), $FeSO_4.7H_2O$ (5 g/l), $MnCl_2.4H_2O$ (0.85 g/l), $CoCl_2.6H_2O$ (0.14 g/l), $CuCl_2.2H_2O$ (0.085 g/l), $H_3BO_3$ (0.17 g/l), $ZnSO_4.7H_2O$ (0.9 g/l), and $Na_2MoO4.2H_2O$ (0.09 g/l). pH of the medium was adjusted to 7.0 and subsequently sterilized by autoclaving at 121° C. for 20 minutes.

Liquid cultivations were applied in Erlenmeyer flasks with baffles and incubated on a Pilotshake RC-4/6-W horizontal shaker (Kühner A G, Birsfelden, Switzerland) at 150 rpm. To prepare CGP overlay agar plates, 1.2% (wt/vol) bacto-agar was added to a CGP suspension (1-2 g/l), this mixture was subsequently sterilized by autoclaving at 121° C. for 20 minutes and after cooling to 45° C., it was poured as thin layers over the previously prepared SM agar plates.

To prepare CGP-overlay agar plates, 1.2% (wt/vol) bacto-agar was added to a CGP suspension (1-2 g l$^{-1}$), this mixture was subsequently sterilized by autoclaving at 121° C. for 20 minutes and after cooling to 45° C., it was poured as thin layers over previously prepared SM agar plates.

Source and Isolation of CGP:

"Recombinant" CGP was isolated from lyophilized cells of Ralstonia eutropha H16-PHB$^-$4-Δeda (pBBR1MCS-2:: cphA$_{6308}$/edaH16) (Voss, I. et al., Metabol. Eng. 8:66-78 (2006)) and purified according to a modified acid extraction method (Frey, K. M. et al., Appl. Environ. Microbiol. 68:3377-3384 (2002)). CGP was isolated from Spirulina commercial products according to the method described previously for cyanobacteria (Simon, R. D. et al., Biochim. Biophys. Acta 420:165-176 (1976)).

To isolate and purify CGP on larger scales, the acid extraction method (Frey, K. M. et al., Appl. Environ. Microbiol. 68:3377-3384 (2002)) was optimized as follows; The CGP-containing dry mass was suspended in tap water to give a final concentration of 0.1 g/ml. pH was reduced to 1 with concentrated HCl (32%) and stirred overnight. The suspension was centrifuged at 17000 rpm with CEPA Z61 continuous centrifuge (CEPA, Carl Padberg Zentrifugenbau GmbH, Lahr, Germany), the pellet was re-suspended in 20 l HCl 0.1 N, stirred for 1 h, centrifuged again and the supernatant was added to the first charge while the pellet was discarded. The CGP-containing supernatant was neutralized (pH 7.3) with NaOH (50%) in 30 l glass bottles so that CGP precipitates. The milky suspension was left to settle overnight in 4° C. before the supernatant was discarded. CGP was repeatedly solved and neutralized for 3 more times to remove all impurities, which are insoluble in diluted HCL. The resulting CGP was resolved in 30 l of HCL 0.1 N and passed through a 0.2 μm Sartobran-P filter unit type 00 (Sartorius AG, Göttingen, Germany). The solution was neutralized again (pH 7.3) with NaOH, left overnight to settle, the supernatant was discarded. To remove any water-soluble impurities and desalt CGP, the pellet was washed 3 successive times with 5 bed volumes of distilled water. Finally, CGP pellet was centrifuged at 20000 rpm (CEPA Z41 contentious centrifuge), frozen at −30° C. and lyophilized in a BETA 1-16 type freeze-dryer (Christ Gefriertrocknungsanlagen, Osterode, Germany).

Sterilization of CGP:

To prepare sterile stock suspensions of CGP, diethyl ether was added to CGP with ratio 3:1 (vol/wt). After 15 min, the solvent was discarded and after complete evaporation a fine suspension was obtained by dissolving CGP in sterile 0.1 N HCl and then precipitating the polymer at pH 7.3 by adding an equal volume of sterile 0.1 N NaOH. Alternatively, CGP was first dissolved in 0.1 N HCl, passed through a filter (pore size 0.2 μm, Millipore GmbH, Eschborn, Germany) and finally re-precipitated as described above. The concentrations of CGP in stock solutions were adjusted by sedimentation of CGP upon short centrifugation (3500×g for 2 minutes) or by simply leaving CGP to sediment overnight at 4° C. In both cases, the supernatant was then partially discarded to finally obtain the desired concentration of CGP. Experiments for anaerobic CGP degradation were conducted in anaerobically prepared Hungate tubes containing 10 ml BM with or without 0.5 g l$^{-1}$ yeast extract. Sterile CGP suspensions were injected directly into the anaerobically prepared BM Hungate tubes to final concentrations of 1 g l$^{-1}$. The visual disappearance of CGP in the tubes indicated its degradation. To prepare CGP overlay agar plates, 1.2% (wt/vol) bacto-agar was added to a CGP suspension, this mixture was subsequently sterilized by autoclaving at 121° C. for 20 min and after cooling to 45° C. it was poured as thin layers over the previously prepared BM agar plates.

Anaerobic Degradation of CGP by Samples of Mammalian, Avian and Fish Gut Flora:

To simulate the natural conditions of the habitats where the flora samples were obtained from, the prepared samples were used as inoculum and as nutritional supplement at the same time. Sterile anaerobic Hungate tubes containing 1 g l$^{-1}$ CGP in BM medium (without yeast extract) were inoculated to a final concentration of 10% and incubated at 37° C. until CGP degradation occurred.

Screening for CGP Degrading Bacteria in Gut Flora:

To isolate CGP degrading bacteria, 100 µl aliquots of the prepared flora samples were spread on aerobically prepared BM agar plates with CGP-overlays. During incubation for several days at 37° C., plates were inspected for the appearance of halos caused by CGP degrading bacterial colonies. Also during incubation, a colony count procedure was applied to determine the ratios between CGP degrading bacterial colonies and the non-degrading ones.

Isolation of CGP Degrading Axenic Cultures:

Morphologically distinct CGP degrading bacterial colonies were selected and further purified by transferring material from colonies showing degradation halos to fresh CGP-overlay agar plates for three successive generations. Further three purification steps were applied on LB agar plates before the axenic culture were tested on CGP-overlay agar plates to confirm that they retained the capability to degrade CGP.

Purity Control:

The purity of the isolated axenic cultures was periodically confirmed by microscopy and also by cultivation on different media under anaerobic as well as aerobic conditions.

Analytical Techniques:

Free amino acids and small peptides (CGP-dipeptides) were detected by reversed phase HPLC (Kontron Instruments, Neufahrn, Germany) after pre-column derivatization of their free amino groups with o-phtaldialdehyde (OPA) reagent as described before (Aboulmagd, E. et al., Arch. Microbiol. 174:297-306 (2000)). For analysis of CGP samples, the polymer was in advance subjected to acid hydrolysis (6 N HCl, 95° C., overnight). Similarly, acid hydrolysis was applied for the qualitative and the quantitative confirmation of the dipeptide-constituting amino acids. The HPLC system was equipped with a B801 column (Prep Nova-Pak HR 3.9×300) (Knauer GmbH, Berlin, Germany), and equilibrated with starting eluent (81%, vol/vol, Na-acetate (50 mM): 19%, vol/vol, methanol). OPA derivatives of amino acids were eluted with a methanol gradient (19-75%, vol/vol) at 40° C. and with flow rate of 1.0 ml/min, and then detected fluorometrically at 330/450 nm (excitation/emission) employing a model 1046A fluorescence detector (Hewlett Packard, Waldbronn, Germany). For calibration, chromatographically pure amino acids were used (Kollection AS-10 from Serva Feinbiochemica, Heidelberg, Germany) or using dipeptides produced by total enzymatic hydrolysis of CGP employing the extracellular CGPase of P. alcaligenes DIP1 (CphE$_{al}$) (Sallam, A. et al., Submitted for publication (2008)).

Bacterial growth was monitored by measuring the increase in turbidity at 578 nm after insertion of the Klett-flasks into an Eppendorf 1101M spectrophotometer (Eppendorf, Hamburg, Germany).

Thin layer chromatography (TLC) analysis was applied on Silica gel 60 plates (Merck, Darmstadt, Germany), the starting eluent of the HPLC was used as rum buffer also for TLC, for staining, 20% (wt/vol) Ninhydrin solution in aceton was applied. Sodium dodecyl sulfate-polyacrylamide gel electrophoresis (SDS-PAGE) was performed in 11.5% (wt/vol) gels after Laemmli, U. K., Nature 227:680-685 (1970). Proteins and cyanophycin were stained with Coomassie staining method (Weber, K. et al., J. Biol. Chem. 244:4406-4412 (1969)) and afterwards with silver-staining method (Heukeshoven, J. et al., Electrophoresis 6:103-112 (1985)) to render proteins with lower concentrations visible.

DNA Extraction and Analysis of 16S rRNA Genes:

The isolation of total genomic DNA from axenic cultures was performed as described before (Rao, R. N. et al., Methods Enzymol. 153:166-198 (1987)). 16S rRNA genes were amplified by PCR from total DNA using standard oligonucleotide primers (MWG-BIOTECH AG, Ebersberg, Germany). PCR products were purified using a Nucleo-trap CR kit (Macherey-Nagel, Düren, Germany) and then directly sequenced. DNA sequencing was performed in custom at the institute for clinical chemistry and laboratory medicine (W.W.U. Münster, Germany) on a capillary sequencer (ABI Prism 3730 DNA analyser) and sequences were analyzed by data collection software v3.0 (both from Applied Biosystems, Darmstadt, Germany). Sequence reactions were prepared using Big-Dye® terminator v3.1 cycle sequencing kit (Applied Biosystems, Darmstadt, Germany) according to procedures indicated by the manufacturer, and the following sequencing primers:

27f
(5'-GAGTTTGATCCTGGCTCAG-3'; SEQ ID NO: 1), 343r
(5'-CTGCTGCCTCCCGTA-3'; SEQ ID NO: 2), 357f
(5'-TACGGGAGGCAGCAG-3'; SEQ ID NO: 3), 519r
(5'-G(T/A)-ATTACCGCGGC(T/G)GCTG-3'; SEQ ID NO: 4), 536f
(5'-CAGC(C/A)GCCGCGGTAAT(T/A)C-3'; SEQ ID NO: 5), 803f
(5'-ATTAGATACCCTGGTAG-3'; SEQ ID NO: 6), 907r
(5'-CCGTCAATTCATTTGAGTTT-3'; SEQ ID NO: 7), 1114f
(5'-GCAACGAGCGCAACCC-3'; SEQ ID NO: 8), 1385r
(5'-CGGTGTGT(A/G)CAAGGCCC-3'; SEQ ID NO: 9)
and 1525r
(5'-AGAAAGGAGGTGATCCAGCC-3'; SEQ ID NO: 10)

(MWG-BIOTECH AG, Ebersberg, Germany).

Sequence analysis and alignment, as well as the construction of the phylogenetic tree were applied as described previously (Sallam, A. et al., Submitted for publication (2008)): nucleic acid sequence data were analyzed with the Contig Assembly Program (CAP) online software. Sequences were aligned with previously published sequences of representative strains and other bacteria using the blast function available on the National Center for Biotechnology Information (NCBI) database. Reference sequences were aligned using the ClustalX 1.8 software and the phylogenetic tree was constructed using the programs TreeView 1.6.5 and NJplot. Bootstraping was applied to evaluate the tree topology by performing 100 resemblings.

Cultivation at 500 l Scale:

Cultivation at 500 l scale was performed in a Biostat D650 stainless steel bioreactor (B. Braun Biotech International, Melsungen, Germany), which had a total volume of 650 l (64 cm inner diameter and 198 cm height) and a d/D value relation (relation of stirrer diameter to vessel diameter) of 0.375. This bioreactor was equipped with three stirrers, each containing six paddles and a Funda-Foam mechanical foam destroyer (B. Braun Biotech International, Melsungen, Germany). In addition, ports were used for sterilizable probes to measure dissolved oxygen ($pO_2$) (model 25; Mettler Toledo GmbH, Steinbach, Switzerland), pH (model Pa/25; Mettler-Toledo GmbH), foam (model L300/Rd. 28; B. Braun Biotech International, Melsungen, Germany), temperature (pt 100 electrode; M. K. Juchheim GmbH, Fulda, Germany), and optical density at 850 nm (model CT6; Sentex/Monitek Technology Inc.). The operations were controlled and recorded by a digital control unit in combination with the MFCS/win software package (B. Braun Biotech International). Cultivations were done at 30° C. and $pO_2$ was adjusted to exceed 40% saturation in the medium, which was automatically controlled by stirring, aeration rate was kept stable at 0.7 vvm (volume per volume×minute). The initial pH of the medium was 6.9 and its increase up to 7.5 during growth was tolerated, otherwise, pH was controlled by the addition of 4 N HCl.

Cell Separation, Concentration, and Desalting of Supernatant-Proteins:

Cells were harvested by centrifugation with a CEPA type Z41 or type Z61 continuous centrifuges (Carl Padberg Zentrifugenbau GmbH, Lahr, Germany). Proteins with molecular size over 30 kDa were concentrated and subsequently desalted (5 bed volumes of $H_2O$) using a cross flow Sartocon® polyethersulfone-cassette with a COP (Cut-Off Point) of 30 kDa and a stainless steel holder of type Sartocon® 2 Plus (Sartorius AG, Göttingen, Germany).

Growth on Different Substrates:

Substrate utilization was investigated in 100 ml Klett-flasks with baffles; each flask contained 10 ml of SM medium and 1 g $l^{-1}$ of one of the following substrates: lactate, citrate, succinate, acetate, propionate, gluconate, glucose, fructose, sucrose, and glycerine. Stock solutions of all substrates were sterilized by filtration (pore size 0.2 µm, Millipore GmbH, Eschborn, Germany). Experiments were performed in duplicates, which were inoculated from a preculture grown under the same test conditions. Growth was monitored by the increase in $OD_{578\,nm}$ after an incubation period of 24 h at 30° C.

Fermentative Production of Cyanophycin:

CGP was produced in 500-l scale fermentation using a recombinant strain of *E. coli* DH1 harboring plasmid pMa/c5-914::cphA$_{PCC6803}$ (Frey, K. M. et al., Appl. Environ. Microbiol. 68:3377-3384 (2002)). As substrate and medium, the previously applied protamylasse (Avebe, Veendam, The Netherlands) medium was used and prepared by dilution, sieving and centrifugation as described by (Elbahloul, Y. et al., Appl. Environ. Microbiol. 71:7759-7767 (2005)).

To determine the optimum concentration of the available charge of protamylasse for CGP production, 100 ml cultivations on protamylasse medium with concentrations between 4-8% (vol/vol) were tested in 200 ml baffled flasks; the medium had pH of 7.5 and contained 100 mg $l^{-1}$ ampicillin. After inoculation, flasks were incubated at 37° C. for 15 h under shaking (120 rpm) (shaker type G 25, New Brunswick Scientific GmbH, Nürtingen, Germany). Finally, CGP content was estimated in a 50 ml sample from each flask.

Prior to fermentation, 16-l of preculture was cultivated in 2-l baffled-flasks each containing 1-l of protamylasse medium (7%; vol/vol, pH 7.5), 100 mg $l^{-1}$ ampicillin and 0.15% (vol/vol) silicon-antifoam emulsion (50%; vol/vol, Wacker Silicones, Burghausen, Germany) and were incubated at 30° C. for 20 h under shaking (110 rpm, shaker type RC-6-W, Adolf Kühner AG, Birsfelden, Switzerland).

Main cultivation was performed in a Biostat D650 stainless steel bioreactor (B. Braun Biotech International, Melsungen, Germany) with total volume of 650 l (64 cm inner diameter and 198 cm height) and a d/D value (stirrer diameter to vessel diameter) of 0.375. The bioreactor was equipped with three stirrers, each containing six paddles and a Funda-Foam mechanical foam destroyer (B. Braun Biotech International, Melsungen, Germany). In addition, ports were used for sterilizable probes to measure dissolved oxygen ($pO_2$) (model 25; Mettler Toledo GmbH, Steinbach, Switzerland), pH (model Pa/25; Mettler-Toledo GmbH), foam (model L300/Rd. 28; B. Braun Biotech International, Melsungen, Germany), temperature (pt 100 electrode; M. K. Juchheim GmbH, Fulda, Germany), and optical density of 850 nm (model CT6; Sentex/Monitek Technology Inc.). Operations were controlled and recorded by a digital control unit in combination with the MFCS/win software package (B. Braun Biotech International).

The bioreactor was filled with 400-l of 7% protamylasse-medium (pH 7.5) and 75 ml antifoam solution, in-situ sterilized and after cooling to 30° C., it was inoculated with 4% (vol/vol) of preculture after addition of 100 mg $l^{-1}$ sterile ampicillin solution. Cultivation was run at 30° C. for the first 6 h, pH of the medium was maintained at 7.5 by the addition of 6 M NaOH or 6 M HCl. $pO_2$ was kept constant at 20% and was adjusted automatically by stirring, aeration rate was kept stable at 0.17 vvm (volume per volume×minute). Foaming was controlled automatically by the mechanical foam-destroyer or by the addition of antifoam sterile solution (50%, vol/vol). After 6 h of incubation, temperature was elevated to 37° C. until the fermentation was terminated. Cells were harvested by centrifugation with a CEPA type Z61 continuous centrifuge (Carl Padberg Zentrifugenbau GmbH, Lahr, Germany).

Large-Scale Extraction and Purification of CGP:

To obtain pure CGP from the resulting wet biomass, the previously optimized acid extraction method for large-scale extraction and purification of CGP was applied (Sallam, A., and A. Steinbüchel. 2008b. Biotechnological process for the technical production of β-dipeptides from cyanophycin. Under preparation). Finally, the extracted CGP was frozen at −30° C. and lyophilized in a BETA 1-16 type freeze-dryer (Christ Gefriertrocknungsanlagen, Osterode, Germany).

Sterilization of CGP:

CGP was sterilized by diethyl ether or by solving in 0.1 N HCl and sterile-filtration as described before (Sallam, A., and A. Steinbüchel. 2007b. Anaerobic and aerobic degradation of cyanophycin by the denitrifying bacterium *Pseudomonas alcaligenes* strain DIP1-Role of other three co-isolates in the mixed bacterial consortium. Submitted for publishing). The desired concentrations of CGP in stock solutions were adjusted by sedimentation of CGP upon short centrifugation (2800×g for 2 min) or by leaving CGP to settle overnight at 4° C., the supernatant was then partially discarded to obtain the desired concentration of CGP.

Analytical Techniques:

Bacterial growth and CGP degradation were monitored by measuring the change in turbidity after insertion of Klett-flasks into a Klett-photometer (Manostat Corporation, New York, USA), or by measuring OD in 1 ml samples at 600 nm with a Libra S5 photometer (Biochrom Ltd., Camebridge, UK). Sodium dodecyl sulfate-polyacrylamide gel electrophoresis (SDS-PAGE) was performed in 11.5% (wt/vol) gels after Laemmli, U. K., Nature 227:680-685 (1970). In-gel-renaturation of proteins was applied after (Lacks, S. A. et al., J. Biol. Chem. 225:7467-7473 (1980)). Proteins and cyanophycin were stained with Coomassie staining method (Weber, K. et al., J. Biol. Chem. 244:4406-4412 (1969)) or with silver-staining method (only for proteins) (Nesterenko, M. V. et al., J. Biochem. Biophys. Methods 3:239-242 (1994)). Concentrations of total protein and CGP were determined using Bradford reagent as described by (Elbahloul, Y. et al., Appl. Environ. Microbiol. 71:7759-7767 (2005)). large-size proteins in cultivation samples were concentrated, desalted and separated from CGP-dipeptides by ultrafiltration using 10 kDa-membrane Vivaspin tubes (Vivascience AG, Hannover, Germany), or using an Amicon-chamber (Amicon, Beverly, USA) with 10 kDa-membranes (Millipore Corporation, Bedford, USA) for larger volumes. Free amino acids and dipeptides were detected by reversed phase HPLC (Kontron Instruments, Neufahrn, Germany) after pre-column derivatization of their free amino groups with Orthophtaldialdehyde (OPA) reagent as described before (Aboulmagd, E. et al., Arch. Microbiol. 174:297-306 (2000)). For analysis of constituting amino acids of CGP or CGP-dipeptide, samples were subjected in advance to acid hydrolysis (6 N HCl, 95° C., overnight). HPLC system was equipped with a B801 column (Prep Nova-Pak HR 3.9×300) (Knauer GmbH, Berlin, Germany) and equilibrated with starting eluent (81%, vol/vol, Na-acetate (50 mM): 19%, vol/vol, methanol). OPA derivatives of amino acids were eluted by a methanol gradient (19-75%, vol/vol) at 40° C. with 1.0 ml min$^{-1}$ flow rate, and then detected fluorometrically at 330/450 nm (excitation/emission) employing a model 1046A fluorescence detector (Hewlett Packard, Waldbronn, Germany).

Determination of CphE$_{al}$ Activity and Concentration:

The activity of the cyanophycinase (CphE$_{al}$) was inspected by formation of degradation halos on CGP-overlay agar plates by small aliquots of concentrated enzyme solutions, for this, 5 ml culture samples were centrifuged at 2800×g for 30 min (Megafuge 1.0 R, Heraeus Sepatech GmbH, Osterode, Germany) and 4 ml of the resulting supernatant were concentrated 100 folds by ultrafiltration. For the quantitative determination of the enzyme in culture samples, a photometric method was developed as follows; 2 µl of the concentrated culture supernatant were added to 1 ml of a CGP suspension (100 mg l$^{-1}$) and incubated at 30° C. for 30 min in a tube rotator (3 rpm, type 502 S, Watson-Marlow GmbH, Rommerskirchen, Germany). Finally, OD$_{600\ nm}$ of samples was measured to indicate the decrease in CGP amount due to degradation; this in turn was used to indicate the concentration of CphE$_{al}$ in solutions through the respective calibration curve.

Optimal Concentrations and Conditions for CGP Degradation:

Using a crude CphE$_{al}$ powder obtained during a previous 500-l fermentation with P. alcaligenes strain DIP1 (Sallam, A., and A. Steinbüchel. 2008b. Biotechnological process for the technical production of β-dipeptides from cyanophycin. Under preparation), and to determine the optimum ratio between CGP concentration and crude CphE$_{al}$ in relation to the required degradation time, serial dilution (50-100 g l$^{-1}$) of pure CGP suspensions (in water, pH 7.3) were prepared in Eppendorf tubes with total volume of 1 ml each, different amounts of crude CphE$_{al}$ powder [4.6% (wt/wt) CphE$_{al}$ content] were added to each prepared CGP concentration, reaction tubes were incubated at 30° C. in a tube rotator (3 rpm) to reveal the required incubation periods for complete CGP degradation.

Experiments to determine the optimum pH for CGP degradation were conducted in Eppendorf tubes containing 1 ml CGP suspension (100 g l$^{-1}$) with pH values between 5.0 and 9.0, reaction tubes contained in addition 10 g l$^{-1}$ crude CphE$_{al}$ and were incubated at 30° C. for 30 min. Reaction mixtures for optimum degradation temperature contained similar concentrations of CGP (pH 7.0) and CphE$_{al}$ and were incubated at 15, 20, 25, 30, 35, 37, 40, 50, 60 or 70° C. for 30 min. After both experiments, CGP degradation in all tubes was calculated in percent and compared together.

Purification of CphE$_{al}$ by Organic Solvents and Ammonium Sulfate Precipitation:

1 ml of concentrations between 10-100% (vol/vol) of cold ethanol, acetone or methanol were added to 50 µl of a concentrated crude CphE$_{al}$ solution (14 g l$^{-1}$) in Eppendorf tubes, reactions mixtures were incubated for 60 min at −20° C. After reaction tubes were centrifuged for 5 min at 16000×g, the pellets were dried and re-suspended in 50 µl sodium phosphate buffer (pH 7.0). Ammonium sulfate fractionation was applied by the stepwise increase in the percent-ammonium sulfate saturation (10-100%) in 10 ml of crude CphE$_{al}$ solution (3.5 g l$^{-1}$), in each step, tubes were incubated at room temperature for 30 min and centrifuged for 10 min at 16000×g, pellets were suspended in sodium phosphate buffer (pH 7.0) then desalted by ultrafiltration. All protein pellets were assayed for CGP degradation on CGP-overlay agar plates as well as for protein content in SDS-PAGE.

Specific Substrate Purification of CphE$_{al}$:

A purification method for CphE$_{al}$ was developed depending on the strong affinity of the enzyme in the crude extract to its insoluble substrate (CGP), where only CphE$_{al}$ binds to CGP and thus can be harvested by precipitation. To determine the time required for the complete binding of the enzyme to CGP at pH 7.0, 0.5 ml of a concentrated crude CphE$_{al}$ solution (14 g l$^{-1}$) was added to 0.5 ml of a CGP suspension (100 g l$^{-1}$). After each of the first 10 incubation minutes, 2 µl aliquot from the reaction supernatant (after short centrifugation) was tested for degradation activity on CGP-overlay agar plates, diminishing of degradation halos indicated complete binding of CphE$_{al}$ to CGP. The actual purification processes was performed in a similar 1 ml reaction mixture and proceed as follows: after the complete binding of CphE$_{al}$ to CGP, the mixture was centrifuged for 30 seconds (16000×g), supernatant was discarded and the pellet was washed 5 times with 10 ml of sodium phosphate buffer (50 mM). Afterwards, the pellet was suspended in 1 ml phosphate buffer and incubated overnight at 30° C. under rotation (3 rpm) until the complete degradation of CGP occurred. The mixture was centrifuged (5 min, 16000×g), CGP-dipeptides were then removed by ultrafiltration and the concentrated protein fraction of the supernatant was analyzed for purity by SDS-PAGE.

Characterization of CphE$_{al}$ from P. alcaligenes Strain DIP1:

To determine temperature stability of the purified CphE$_{al}$, 10 µl aliquots were incubated for 20 min at different temperatures (10-80° C.), 3 µl thereof were then tested for degradation activity on CGP-overlay agar plates at 30° C. For the optimum degradation temperature, 3 µl aliquots of the purified CphE$_{al}$ solution were added to 1 ml CGP suspensions (100 g l$^{-1}$ in 50 mM Na-phosphate buffer, pH 7.0) and incubated for 20 min at different temperatures (10, 20, 30, 40, 45, 50 and 60° C.). For the optimum degradation pH of CGP by the purified CphE$_{al}$, 3 µl aliquots of the purified CphE$_{al}$ stalk solution were added to 1 ml CGP suspensions (100 g l$^{-1}$ in 50 mM Na-phosphate buffer) with different pH values (5, 5.5, 6, 6.5, 7, 7.5, 8, 8.5 or 9) and incubated for 30 min at 30° C. Finally, CGP degradation was determined photometrically in reaction tubes of both experiments as described above. Substrate specificity of purified CphEal was tested as described before (Obst, M. et al., Biomacromolecules 5:153-161 (2004)) on the following polypeptide substrates CGP, bovine casein (Hammersten-grade) (Merck, Darmstadt, Germany), bovine serum albumin (BSA) (Roth, Karlsruhe, Germany), and poly($\alpha,\beta$-D/L-aspartic acid) (Bayer AG, Leverkusen, Germany).

To reveal the effect of enzyme inhibitors on the purified CphE$_{al}$, 50 µl aliquots of the purified enzyme stalk solution were added to 450 µl of Na-phosphate buffer (50 mM) and incubated for 2 h at 30° C. in the presence of one of the following Group-specific inhibitors; Leupeptin (thiol-proteases), EDTA (metalloproteases), Pefabloc (serine-proteases), PMSF (serine-proteases) or N-bromosuccinimide (tryptophan residues). 5 µl sample of each reaction mixture was assayed for activity on CGP-overlay agar plates. Afterwards, 5 µl aliquots of a CGP stalk suspension (50 g l$^{-1}$) were added to the reaction tubes, incubated for further 15 min, centrifuged, and screened for degradation products via HPLC.

Example 1

Anaerobic Degradation of CGP by Samples from Mammalian, Avian and Fish Gut Flora The filtered flora samples contained a large number of different bacteria as well as high content of substrates. To simulate the natural conditions inside the digestive tracts where these samples were obtained from, the flora solutions were used as inoculum and as nutritional supplement at the same time. Sterile anaerobic Hungate tubes containing BM medium and 1 g l$^{-1}$ CGP as sole substrate were inoculated in a concentration of 10%. All inoculated anaerobic tubes showed complete CGP degradation under these conditions. The incubation periods required for the complete degradation of CGP in the tubes ranged from 12 to 48 h.

Screening for CGP Degrading Bacteria in Gut Flora:

To isolate CGP degrading bacteria, 100 µl aliquots of the prepared flora samples were spread on CGP-overlay agar plates. During incubation for several days at 37° C., plates showed that occurrence of CGP degrading bacteria varied largely among different flora (Table 1). The highest incidence was in case of cecum flora from rabbit (Egypt), sheep (Germany) and digestive tract flora from carp fish (Germany). Also the morphological characteristics of the degrading colonies, the required incubation period, form and intensity of halos caused by CGP degradation varied largely among different flora samples as well as among colonies within each sample. This indicated the presence of distinctive bacterial species with diverse capabilities of CGP degradation.

Isolation and Purification of CGP Degrading Strains:

Morphologically distinct CGP degrading bacterial colonies were selected and further purified by transferring colonies showing degradation halos to fresh CGP-overlay agar plates. During purification work, many CGP degrading colonies lost their ability to induce degradation halos as axenic cultures and were therefore disregarded. Similarly, several CGP degrading consortia showed extreme difficulties to be obtained as axenic cultures and were also omitted from further purification procedures. On the other hand, the purification phase resulted in 62 axenic cultures, which showed morphologically distinctive characteristics with retained capability of CGP degradation. As demonstrated in Table 1, CGP degrading bacteria were isolated from different sites along the digestive tract of each animal. This is in accordance with the facts known about the degradation of dietary protein for example in ruminants; while the rumen is the major degradation site for dietary protein, undigested protein (bypass or escape protein) moves with the digesta into the lower digestive tract, where a portion thereof is broken down by the animal's enzymes or by the lower gut flora to be then absorbed before the rest gets excreted. The degradation of bypass protein is important for specific physiological functions such as milk production (Holter, J. B. et al., J. Dairy. Sci. 76:1342-1352 (1993)).

Degradation of CGP by Axenic Cultures Under Anaerobic and Aerobic Conditions:

The 62 axenic cultures were examined for the capability to degrade CGP in liquid media under aerobic conditions. This was applied in BM medium containing 1 g l$^{-1}$ CGP and 0.5 g l$^{-1}$ yeast extract and signified the capability of all axenic cultures to degrade CGP (Table 1). Anaerobic CGP degradation experiments in Hungate tubes containing similar medium in addition to reducing agents, revealed that from the 62 isolated strains, 46 could degrade CGP anaerobically as well. Of those, 38 degraded CGP completely while the rest showed partial CGP degradation. The incubation periods required for the anaerobic CGP degradation by axenic cultures ranged from 24 h to 7 days at 37° C.

Degradation Products of CGP:

Directly after the complete degradation of CGP by the 62 pure isolates in aerobic and anaerobic cultures, degradation products of CGP in culture supernatants were determined by HPLC after pre-column derivatization with OPA reagent as mentioned in the methods section. As expected, HPLC analysis revealed that all isolates degrade CGP to its constituting dipeptides. Similar analysis for supernatant samples that have been subjected in prior to acid hydrolysis revealed the presence of the three CGP-constituting amino acids; aspartate, arginine and lysine. The detection of the latter three amino acids is in accordance with the known composition of recombinant CGP which was applied for these experiments, where approximately 6 Mol % of the arginine moieties are replaced with lysine (Voss, I. et al., Metabol. Eng. 8:66-78 (2006)).

Taxonomic affiliation of the CGP degrading axenic cultures: The morphological characteristics of the isolated axenic cultures suggested that approximately 50% of the isolates belong to the genera *Bacillus* and *Pseudomonas*, while the remaining isolates belong to other genera including *Streptomyces* and *Micromonospora*. To provide a clearer insight on the phylogeny of the CGP degrading bacteria in the examined gut flora, eight strains from the 62 were further identified by 16S rDNA sequencing. As shown in table 1, three isolates; 17, 35, 49 from rumen flora of sheep (Germany), cecum flora of turkey (Egypt), and the digestive tract flora of tilapia fish (Egypt), respectively, were identified as members of the genus *Bacillus* with 16S rDNA sequence similarity of over 99% to *B. megaterium* AC46b1, *B. megaterium* MPF-906 and *B. Koguryoae* SMC4352-2$^T$, respectively. Two isolates; 15 and 47 from colon flora of cow (Germany) and cecum flora of pigeon (Egypt) were found to belong to the genus *Brevibacillus* with 16S rDNA sequence similarity of over 98% to *B. reuszeri* DSM9887$^T$ and *Brevibacillus* sp. SE004, respectively. Strain 31, isolated from rabbit cecum (Germany) was affiliated to the genus *Streptomyces* with sequence similarity of over 98% to *S. avermitilis* NCIMB 12804$^T$. 16S rDNA sequence analysis also showed that strain 38 from duck cecum (Germany) belongs to genus *Micromonospora* and has a sequence similarity of over 99% to *Micromonospora* sp. 0138. Finally, a representative of genus *Pseudomonas* was also found among the identified isolates; strain 52 from carp fish (Germany) showed 16S rDNA sequence similarity of over 99% to the CGP degrading bacterium *P. alcaligenes* DIP1.

The constructed phylogenetic tree (FIG. 1) shows the relationship between the eight identified strains from diverse animal, avian and fish flora to their closely related strains and to other bacteria. Moreover, the taxonomic position of all known bacteria capable of extracellular CGP degradation is demonstrated in the phylogenetic tree. Further Table 2 provides an overview on the wide spread, habitats, and phylogeny of bacteria capable of extracellular CGP degradation.

CGP in *Spirulina platensis* Commercial Products:

The market name *Spirulina*, which is often associated with several nutritional benefits and thus used as additives for human and animals (Narasimha, D. L. R. et al., J. Sci. Food Agric. 33:456-460 (1982); Kihlberg, R., A. Rev. Microbiol. 26:427-466 (1972); Lu, J. et al., Aquaculture 254:686-692 (2004); Ross, E., Poult-Sci. 69:794-800 (1990))). To investigate whether this is associated with the presence of CGP, three *Spirulina* products available on the German market were inspected for the presence of CGP. Two products; from Sanatur GmbH (Singen, Germany) and Greenvally GmbH (Berlin, Germany) consisted of 100% *Spirulina* platensis, while the third variant from Aurica GmbH (Schwalbach-Elm, Germany) contained 40% thereof. 10 g CDM of each of the three products that corresponds approximately the double of the usual daily dose were prepared by grinding to a fine powder before CGP isolation. The three market variants showed CGP contents of 0.06%, 0.13% and 0.15%, respectively. Confirmatory HPLC analysis of hydrolyzed samples of the isolated CGP revealed, as expected, the typical constituting amino acids of cyanobacterial CGP; aspartate and arginine.

Example 2

Development of an Optimal Process for the Production of β-Dipeptides from CGP

Several factors were first optimized on small scale, for example; a required suitable and economic media, highly concentrated suspensions of CGP which can be practically prepared for degradation, and to define the necessary amount of the extracellular enzyme to achieve the complete CGP-degradation in a relatively short incubation period.

The change in $OD_{600\,nm}$ During the production of CphE due to the addition of the inductor (CGP) and its subsequent degradation, represents a definite sign for the release of the CphE, therefore, a clear medium and a controlled growth of cells were necessary, this was achieved through the final medium composition mentioned in materials and methods section. Moreover, among the tested substrates, strain *P. alcaligenes* DIP1 showed best growth on citrate (FIG. 3), the applied concentration of citrate (1 g/l) as sole substrate guaranteed for a reasonable but in the same time controlled growth turbidity of cultures during the induction and degradation phases.

To determine a balanced ratio between CGP and the crude CphE concentrations for the degradation phase of the large scale process (phase III, see under), the following small scale experiments were conducted; serial dilution (10-50 g/l) of pure CGP suspensions (in water, pH 7.3) were prepared in Eppendorf tubes with total volume of 1 ml each, Furthermore, a serial dilution (1-10 g/l) of crude CphE was tested on each prepared CGP concentration, the reaction tubes were incubated at 30° C. in a tube rotator with rotation rate of 3 rpm. The experiments showed a relatively constant increase in CGP degradation time when lower concentrations of crude CphE were used. The highest tested concentration of CGP (50 g/l) could be degraded within 10 h in the presence of 2 g/l crude CphE powder (FIG. 4).

Large Scale Production of CGP-Dipeptides:

To enable the routine production of large quantities of pure CGP-dipeptides, a triphasic process was constructed; Phase I: large scale isolation and purification of CGP, Phase II: large-scale production of crude CphE powder, Phase III: degradation of CGP to its dipeptides.

Phase I (Large Scale Isolation and Purification of CGP):

To obtain a large amount of CGP, 4776 g cell dry mass of CGP-containing cells were used, this amount was previously produced during one 500 l fermentation with Ralston/a eutropha H16-PHB⁻-4-Δeda (pBBR1MCS-2::cphA$_{6308}$/edaH16). CGP content of this biomass charge was 32% (wt/wt) (Voss, I. et al., Metabol. Eng. 8:66-78 (2006)). Additionally, several other dry biomass charges from lab-scale fermentations with *R. eutropha* H16-PHB⁻-4-Δldh/Ωkm-cphA$_{6308}$ were mixed (a total of 2490 g) and considered as a secondary charge. CGP was extracted and purified from each charge separately according to the modified acid extraction method mentioned in materials and methods section. The resulting CGP wet mass was 1948 g for the main cell charge and 295 g for the secondary charge, after dry-freezing of the purified CGP, 621.83 g and 82.17 g of pure CGP were obtained from both charges, respectively.

HPLC analysis of the individual amino acid constituents of the isolated CGP from both cell charges revealed that the polymer was mainly composed of aspartate and arginine and that it contained only little lysine of 4.5% (mol/mol). SDS polyacrylamide gel electrophoresis revealed that the isolated CGP in both charges has a molecular weight of about 20 to 30 kDa. Moreover, Both HPLC analysis and SDS polyacrylamide gel electrophoresis indicated the lack of any impurities in the obtained CGP. Thus, both CGP charges could be mixed together to a final amount of 704 g of pure CGP.

Phase II (Large Scale Production of Crude CphE Powder):

To continue towards the development of a process for the commercial production of CGP-dipeptides, the production of enough amount of crude CphE from *P. alcaligenes* DIP1 was necessary, therefore, the strain was cultivated at 500 l scale in a Biostat D650 bioreactor. The preculture of *P. alcaligenes* DIP1 was cultivated in 2 l baffled-flasks containing 1 l of SM medium with 1 g/l sodium citrate; the flasks were incubated under shaking for 12 h at 30° C. The bioreactor was filled with 420 l of SM medium containing 1 g/l sodium citrate, sterilized, and inoculated with 4% (vol/vol) preculture. Initial pH was adjusted to 6.9. During fermentation, Cells of strain *P. alcaligenes* DIP1 started to grow slightly after the first fermentation h and reached $OD_{600\,nm}$ value of 0.4 to inter the stationary phase after nearly 9 h. The excretion of CphE was induced by the addition of 0.25 g/l sterile CGP suspension after the first 2 h of the stationary phase, the addition of the inductor (insoluble CGP) increased the $OD_{600\,nm}$ immediately from 0.55 to 0.98, the complete degradation of the added CGP required 2 h and was indicated by the decrease of $OD_{600\,nm}$ to reach a value close to that before induction. One h later, cells started to grow slightly which is most probably due to the presence of CGP-dipeptides in the medium. The fermentation was terminated after a total cultivation period of 14 h (FIG. 5).

For harvesting, concentration and desalting of proteins in the supernatant including the excreted extracellular cyanophycinase, a continuous system was prepared while the fermentation was running (FIG. 6); for harvesting, a CEPA Z41 continuous centrifuge was used to separate the cells while the supernatant was collected in a central 100 l tank. To concentrate the collected supernatant simultaneously, a cross flow unit with a 30 kDa cassette was connected to the central tank; the concentrated retentate containing proteins with molecular size larger than the COP of the filter cassette (30 kDa) was re-pumped into the tank, while the permeate was directly discarded. The flow rate of the cross flow was adjusted to maintain the volume in the tank at about 50 l. For cooling, an ice bag was introduced into the central tank to maintain the temperature of the solution under 20° C. After harvesting came to an end, the concentration process continued until only 5 l concentrate remained in the tank. For desalting, the concentrate was washed with 5 bed volumes of $H_2O$. During each of the previous steps, samples were collected and checked for CGP-degradation activity on CGP-overlay agar plates (FIG. 2). Finally, the concentrate was frozen at −30° C. and lyophilized to obtain a final dry weight of crude protein powder of 17.5 g.

Phase III (Degradation of Pure CGP to its Dipeptides):

The large scale degradation of CGP to its dipeptides was applied on 250 g pure CGP and using 10 g of the crude CphE powder, these amounts represent the highest—easy to prepare—CGP concentration (50 g/l) and the sufficient concentration of crude CphE (2 g/l) to assure the complete degradation within 12 h as determined by the small scale experiments. The 250 g CGP powder were resolved in 5 l of 0.1 M HCL, neutralized to pH 7.3, left to sediment in 4° C., and finally desalted by washing 3 times with tap water to obtain the desired concentration in a total volume of 5 l. Afterwards, the 10 g of the crude CphE powder were added to the CGP suspension and incubated for 12 h at 30° C. under weak stirring. After the complete degradation of CGP, the dipeptide solution was sterile-filtered, separated from the crude protein components with the same cross flow system used during phase II, frozen at −30° C., and finally lyophilized to obtain 227.5 g of CGP-dipeptides.

In order to determine if further filtration steps are necessary for the purification of CGP dipeptides, several 20 ml aliquots (taken before the later freezing and lyophilization steps) were filtered with different membranes having the following COPs; 10, 5, 1, and 0.5 kDa. After filtration, the loss of CGP-dipeptides was evaluated by determining the dry weight of lyophilized 1 ml aliquots before and after filtration, as well as by HPLC analysis. Compared to the original dipeptide solution, the maximum dry weight loss during filtration was in the case of the membrane with the smallest COP (0.5 kDa) which was 78.5% (wt/wt), the membrane with 1 kDa caused a loss of 47.8% (wt/wt), while that with 5 kDa caused a loss of 11.6% (wt/wt), the filter-membrane with higher COP (10 kDa) showed a minimal loss of 7.4% (wt/wt).

The purity grade of the dipeptides resulting from all filtration systems was monitored by TLC as well as HPLC analysis, all filtered dipeptide samples showed the same high grade of purity (FIG. 7, I). Thus, no further filtration steps were needed for the main dipeptide charge. The cross flow with the 30 kDa cassette was clearly the most practical instrument also to regain the protein portion of the degraded CGP solution. The regained protein solution was frozen and lyophilized again. The activity test for the regained powder on CGP-overlay agar plates showed that CphE survived all the previously mentioned procedures and retained its activity (FIG. 2). The recovery rate for the crude powder was 78%.

For the final quality control of the resulting dipeptide powder, direct samples as well as acid hydrolyzed samples were examined by TLC; only one spot was indicated for the direct samples (FIG. 7, I) while the hydrolyzed ones showed the typical spots for the standard amino acids aspartate, arginine and lysine (FIG. 7, II). Also, the confirmatory HPLC analysis for the acid hydrolyzed samples revealed only the typical peaks for these 3 constitutive amino acids. On hand of these results, the purity of the dipeptide powder was estimated to be over 99%. The final outcome (227.5 g pure dipeptides) from the degradation of 250 g CGP indicates that the overall efficacy of the whole process represents 91%, which may be even more increased through future optimizations.

Example 3

Fermentative Production of Cyanophycin at 500 l Scale

A sufficient amount of CGP for this study was produced in 500-l scale fermentation after (Elbahloul, Y. et al., Appl. Environ. Microbiol. 71:7759-7767 (2005)). However, the recombinant strain *E. coli* DH1 (pMa/c5-914::cphA$_{PCC6803}$) was cultivated on 7% protamylasse (vol/vol); this concentration was proved to be optimum for CGP production during pre-experiments on the available charge of protamylasse.

During fermentation (FIG. 8) and after the first 6 h of incubation, temperature was elevated to 37° C. to enable the induction of the CGP-synthetase (CphA) gene (Frey, K. M. et al., Appl. Environ. Microbiol. 68:3377-3384 (2002)). Samples taken each h showed, as expected, a progressive intracellular accumulation of the polymer which reached maximum after 13 h (microscopically estimated) and remained constant afterwards (FIG. 9). $OD_{600\ nm}$ reached 18.3 after 15 h and the fermentation was then terminated, however, later analysis revealed maximum CGP accumulation of 13% (wt/wt of CDM) to be after 13 h of fermentation and that it sank to 10% (wt/wt of CDM) at the harvest time (15 h). After CGP extraction from the resulting 4626 g wet-mass of cells (1372 g CDM), 135 g of pure CGP powder were obtained, HPLC analysis of CGP indicated only the constitutive amino acids aspartate, arginine in addition to lysine which represented 6.8 Mol % of the polymer. SDS-PAGE confirmed the purity of CGP and showed a molecular weight of 25-30 kDa.

Optimum Growth Conditions for *P. alcaligenes* Strain DIP1:

Testing SM-medium with different concentrations of citrate (0.5-10 g $l^{-1}$), which was previously proved to be an optimal substrate for strain DIP1 (Sallam, A., and A. Steinbüchel. 2008b. Biotechnological process for the technical production of β-dipeptides from cyanophycin. Under preparation), showed that 6 g $l^{-1}$ produces maximal growth (475 Klett units after 13 h at 30° C.). Cultures of strain DIP1 cultivated on 6 g citrate under the same conditions but having different pH values (5.5-8.5) showed that strain DIP1 has an optimum growth pH of 6.5, while cultivations at different incubation temperatures (15-45° C.) revealed 37° C. as the optimum temperature for growth.

Optimum Cultivation Conditions for Maximum CphE$_{al}$ Production by *P. alcaligenes* Strain DIP1:

To conclude the optimum cultivation conditions for maximum production of CphE$_{al}$ by strain DIP1, cells were cultivated on different concentrations of citrate under optimum growth conditions, when cells reached the stationary phase; CphE$_{al}$ production was induced by the addition of 0.25 g CGP.

During the following 5 h, supernatant samples were concentrated (100 folds) and screened for degradation activity on CGP-overlay agar plates as well as photometrically. Supernatant samples from cultures with citrate concentrations below 0.5 or higher than 4 g $l^{-1}$ did not show any degradation activity, while the maximum activity and subsequently maximum CphE$_{al}$ production was monitored after 5 h of induction for cultures grown on 2 g $l^{-1}$ citrate. Further cultivation experiments under optimal production conditions confirmed that cells of strain DIP1 reach the stationary phase after about 13 h of incubation and proved this time point to be optimal for the induction of $CphE_{al}$. Thus, the following conditions were considered optimum for $CphE_{al}$ production; SM-medium with 2 g l$^{-1}$ citric acid, pH 6.5, 37° C., induction after 13 h, and harvesting during the 16$^{th}$ incubation h.

Optimum Induction of $CphE_{al}$ with CGP and Alternative Inductors:

Besides CGP, other possible inductors were tested in cultures of strain DIP1; β-Dipeptide from CGP, synthetic dipeptides (α-arginine-aspartate, α-lysine-aspartate, α-ornithine-aspartate) (Sigma-Aldrich, St. Louis, Mo., USA), α-polyaspartate (Bayer AG, Leverkusen, Germany), poly-ε-Lysine (Chisso, Tokyo, Japan), L-aspartate, L-arginine, L-lysine, L-citrulline, L-ornithine as well as aspartate analogues [N-acetyl-aspartate, ureidosuccinic acid (N-Carbamoyl-aspartate)]. All inductors were tested first at a concentration of 0.25 g l$^{-1}$ and $CphE_{al}$ production was assayed on CGP-overlay agar plates and also photometrically. Only CGP, the dipeptides thereof and aspartate induced significant amounts of $CphE_{al}$. Subsequently, optimum concentrations and optimum $CphE_{al}$ harvesting time were investigated in cultures induced with these three inductors; for CGP, concentrations between 0.001-3.0 g l$^{-1}$ were tested, the inductive effect increased with concentrations up to 0.05 g l$^{-1}$ while higher concentrations showed the same efficiency. Maximum $CphE_{al}$ production was obtained after 5 h from induction with 0.05 g l$^{-1}$ CGP.

Cultures cultivated under similar conditions but induced with CGP-dipeptides within the same concentration range tested for CGP, showed similar results regarding the concentration of inductor, however, maximum $CphE_{al}$ production was obtained after only 3 h of induction. Also aspartate proved to be a suitable inductor where maximum $CphE_{al}$ production was obtained with 4 g l$^{-1}$ aspartate after 5 h of induction; however, in comparison to cultures induced with optimum CGP concentration (0.05 g l$^{-1}$), $CphE_{al}$ production after induction with aspartate represented only the third.

Optimum Conditions for CGP Degradation to Dipeptides Via Crude $CphE_{al}$:

In order to decrease the handled reaction volumes and the time required for the third phase (CGP degradation) of the original process, degradation time of higher CGP concentrations (50-100 g/l) were tested at 30° C., this showed a collinear increase in degradation time with decreasing concentrations of crude $CphE_{al}$ and with increasing CGP concentrations. In presence of 10 g l$^{-1}$ crude $CphE_{al}$, the shortest degradation period (4 h) was monitored for the lowest tested concentration of CGP (50 g l$^{-1}$) while 16 h were required to degrade the highest tested CGP concentration (100 g l$^{-1}$).

Experiments for estimating the optimum pH and temperature for CGP degradation by the crude $CphE_{al}$ powder were conducted separately as described in materials and methods section. Photometrical determination of the remaining CGP in reaction tubes indicated that maximum CGP degradation (45%) occurred at pH 6.5, however, pH range from 5.5 to 7.5 revealed close results. On the other hand, CGP degradation increased with increasing temperature to reach a maximum of 90% at 50° C. Thus, experiments for the optimum relation between the concentrations of CGP and $CphE_{al}$ were repeated under the optimum parameters (50° C., pH 6.5). This reduced the required degradation time (in presence of 10 g l$^{-1}$ crude $CphE_{al}$) for CGP concentrations of 50 and 100 g l$^{-1}$ to 1 and 4 h, respectively. Also under optimum conditions, degradation time showed a collinear increase with decreasing concentrations of crude $CphE_{al}$ and with increasing CGP concentrations. This collinear relation can be helpful to apply optimum degradation parameters during future process applications. The respective formula is calculated for CGP concentrations up to 100 g l$^{-1}$ and based on the concentration of pure $CphE_{al}$ (E), for applying crude extracts, $CphE_{al}$ content must be determined (s.u.) before using the formula;

$$P_{Degradation\ time\ at\ 50°\ C.} = 17.55 - 29.891 E_{[Desired\ concentration\ of\ pure\ CphEal(g/l)]}$$

Purification of $CphE_{al}$ from Crude Supernatant Powder:

To move further towards a more efficient process and to obtain better knowledge about the characteristics of the CGPase from *P. alcaligenes* strain DIP1, several technically applicable methods were tested to purify $CphE_{al}$ from crude powder. Precipitation and purification of the enzyme using solvents such as ethanol, methanol or acetone could not provide satisfactory results due to low recovery rates and low purification effect. However, ammonium sulfate precipitation provided comparably better results with a saturation concentration of 70% but the purity grade was rather too low.

Purification of $CphE_{al}$ Via Specific Substrate Binding:

A simple method was developed to purify the CGPase from *P. alcaligenes* strain DIP1. For this, the insoluble CGP itself was used as a binding matrix to specifically bind $CphE_{al}$ as described in materials and methods section. Pre-tests showed that $CphE_{al}$ binds completely to CGP after the first 5 min, therefore, this was considered as a minimum binding time in further applications. SDS-PAGE of all purification steps showed a gradual purification of the enzyme (FIG. 10A) and that the first two washing steps are necessary to remove other proteins which did not bind to CGP. After degradation of CGP matrix and removing dipeptides by ultrafiltration, a high purity grade of $CphE_{al}$ was obtained. CGP-Overlay agar plates showed high activity of the purified $CphE_{al}$ and the purified protein showed an apparent molecular weight of 45 kDa in SDS-PAGE. Identity of $CphE_{al}$ was confirmed by in-gel-renaturation where it regained activity and formed degradation halos on CGP-overlay agar plates. Concentration of the purified $CphE_{al}$ was 43.2 μg ml$^{-1}$ while the total protein content in the initial crude protein solution was 944 μg ml$^{-1}$. To detect the purity grade of the purified enzyme more accurately, SDS-PAGE was repeated for a larger sample volume (triple volume) and stained for longer time with silver staining; this revealed the presence of few other protein bands in comparably much lower concentrations (FIG. 10B).

Determination of $CphE_{al}$ Content in Fermentation Supernatants:

If the application of pure $CphE_{al}$ is desired in future process applications, concentration of the CGPase has to be estimated in the produced supernatants at first, therefore, a fast test was developed using 1 ml of CGP-suspension with fixed concentration (100 mg l$^{-1}$) which has an $OD_{600\ nm}$ of 0.215. To this solution, 3 μl of solutions with different concentrations (2.7-43.2 μg ml$^{-1}$) of the purified enzyme were added. Reactions were incubated for 60 min at 30° C. under slow rotation (3 rpm). Finally, the extent of CGP degradation was photometrically determined at 600 nm. To guarantee for the reproducibility of the test and the accuracy of the formula thereof (s.u.), test parameters and the measurement range at $OD_{600}$ (0.15-0.215) must be preserved.

$$E_{[CphEal\ content\ in\ crude\ extract\ (\mu g/ml)]} = [0.2404 - D_{(OD600\ nm\ after\ 60\ min)}]/0.0017$$

Required CGP Amounts for the Technical Purification of $CphE_{al}$:

To integrate the enzyme purification procedure in the main production process, also the amount of CGP, which is necessary to bind all $CphE_{al}$ (in supernatants with known $CphE_{al}$ content) has to be determined. In a total reaction volume of 0.5 ml, 50 μl of purified $CphE_{al}$ solutions with different concentrations (1.4-19 μg ml$^{-1}$) were added to different CGP concentrations (0.1-6 g l$^{-1}$). Reaction mixtures were incubated for 10 min at 30° C. under slow rotation (3 rpm). After centrifugation (16000×g, 2 min), reaction tubes were centrifuged and the supernatants were screened for activity on CGP-overlay agar plates. For all tested $CphE_{al}$ concentrations, the minimum CGP-concentrations that did not induce degradation halos were multiplied 3 times for safety and then integrated in a calibration curve. The resulting formula was as follows:

$$C_{[required\ CGP\ concentration\ (g/l)]} = [E_{[CphEal\ content\ in\ crude\ extract(\mu g/ml)]} - 2.4392]/0.9432$$

Biochemical Characterization of the Purified $CphE_{al}$:

The purified $CphE_{al}$ showed maximum CGP degradation activity at 50° C. while complete inactivation of the enzyme occurred at 68° C. Optimum pH range for CGP degradation was 7-8.5 with an optimum at 8.5. Testing substrate specificity of the purified $CphE_{al}$ on CGP, BSA, bovine casein, and poly(aspartic acid) showed the highest degradation activity on CGP. However, also BSA was partially degraded (65% in comparison to CGP). Bovine casein and poly(aspartic acid) were minimally affected by the enzymatic activity of the purified $CphE_{al}$.

To gain information on the catalytic mechanism of $CphE_{al}$, inhibitor experiments were conducted employing different group-specific inhibitors (Table 1). Inhibition of the CGPase was assayed on CGP-overlay agar plates and by HPLC analysis of CGP degradation products. This revealed that the extracellular $CphE_{al}$ is strongly inhibited by serine protease inhibitors Pefabloc and phenylmethylsulfonyl fluoride (PMSF). Also N-bromosuccinimide (tryptophan oxidant) led to a total inhibition of the enzyme. In contrast, formation of degradation halos by $CphE_{al}$ was not affected by the thiol protease inhibitor leupeptin or by the metalloprotease inhibitor EDTA. HPLC analysis confirmed these results except for samples treated with EDTA, which showed inhibition of $CphE_{al}$.

Example 4

Absorption of CGP Dipeptides by Caco2-Cell Cultures

To prove the potential applications of CGP dipeptides in nutrition and therapy, the absorption of these highly soluble dipeptides was tested using cell cultures of Caco2 cells (human-colon epithelial adenocarcinoma cells) in a preliminary study. A Dulbecco's Modified Eagle Medium (DMEM) containing 20% Fetal Calf Serum (FCS) and 1% of 2 mM Glutamine solution was used as cultivation medium. About 7000 Caco2 cells per well were disseminated in a 24-well plate and incubated at 37° C. under an atmosphere of 5% $CO_2$ and about 98% humidity. The cells were checked microscopically on a daily basis until forming monolayer after nearly 50 h. The incubation medium was replaced completely with fresh 700 μl per well of the same medium supplied with 350 μg/ml of CGP dipeptides (90% Asp-Arg: 10% Asp-Lys) or with a mixture of equivalent amounts of free L-aspartic acids, L-arginine and L-lysine. A well line was supplied with fresh 700 μl of the incubation medium without the latter additives and was considered as control. Samples were taken after incubation periods of 0, 13, 22, 67 and 113 h and were analyzed by HPLC as described by Sallam and Steinbüchel (J. App. Microbiol. DOI: 10.1111/j.1365-2672.2009.04221.x) to determine the change of concentrations of the tested dipeptides and amino acids.

HPLC analysis of the medium samples revealed the absorption of approximately 60% of cyanophycin Asp-Arg dipeptides and 68% of cyanophycin Asp-Lys dipeptides after 113 h of incubation. On the other hand, only 41% of free arginine and 51% of free L-lysine were absorbed over the same incubation period. Exceptionally, L-aspartic acid seems to be better absorbed in the free form by Caco2 cells and was absorbed completely in a shorter incubation period of about 67 h. On the contrary, and in comparison to the absorbed amounts of free arginine and free lysine, 31.6% more arginine and 24.4% more lysine were absorbed by the cells in the form of CGP dipeptides. Thus, CGP dipeptides represent a higher bioavailable sources for both amino acids arginine and lysine. These results are the first direct evidence on the potential application of CGP dipeptides in nutrition and therapy and confirm the previous results on the degradation of CGP by the gut flora (Sallam and Steinbüchel J. App. Microbiol. DOI: 10.1111/j.1365-2672.2009.04221.x). The results are also in agreement with previous in vitro and in vivo studies which proved that oligopeptides—in general—have higher bioavailability than their constituting amino acids in the free form (Adibi, S. A., J. Clin. Invest. 50:2266-2275 (1971); Adibi, S. A., Gastroenterology 113:332-340 (1997); Dock, D. B. et al., Biocell 28:143-150 (2004)).

TABLE 1

| Wide spread, phylogeny, and characteristics of CGP degrading bacteria in mammalian, avian and fish gut flora. | | | | | | | |
|---|---|---|---|---|---|---|---|
| Flora source/ Sampling site-(Country) | Dilution factor | Halo forming colonies % | CGP degrading isolates (total) | CGP degrading isolates (anaerobically) | Identified isolates | CGP degradation | |
| | | | | | | Oxic | Anoxic | Genus |
| I. mammalian flora Bovine [Red angus; *Bos taurus*] | | | | | | | | |
| Rumen (Ger) | 100× | 0.9 | 7 | 4 | | | | |
| Colon (Ger) | 100× | 2.1 | 9 | 6 | Strain 15 | + | ± | *Brevibacillus* |
| Ovine: [Swiss black-brown mountain; *Pecora giurassiana*] | | | | | | | | |
| Rumen (Ger) | 100× | 2.3 | 3 | 3 | Strain 17 | + | + | *Bacillus* |
| Reticulum (Ger) | 50× | 1.7 | 4 | 3 | | | | |

TABLE 1-continued

Wide spread, phylogeny, and characteristics of CGP degrading bacteria in mammalian, avian and fish gut flora.

| Flora source/Sampling site-(Country) | Dilution factor | Halo forming colonies % | CGP degrading isolates (total) | CGP degrading isolates (anaerobically) | Identified isolates | CGP degradation Oxic | CGP degradation Anoxic | Genus |
|---|---|---|---|---|---|---|---|---|
| Omasum (Ger) | 100× | 1.6 | 2 | 1 | | | | |
| Abomasum (Ger) | 20× | 1.2 | 1 | 1 | | | | |
| Cecum (Ger) | 100× | 3 | 3 | 3 | | | | |
| Rabbit: [European wild; *Oryctolagus cuniculus*] | | | | | | | | |
| Cecum (Ger) | 50× | 1.9 | 3 | 2 | Strain 31 | + | ± | *Streptomyces* |
| Cecum (Egy) | 50× | 3.5 | 1 | 1 | | | | |
| II. Avian flora Duck: [Muscovy; *Cairina moschata*] | | | | | | | | |
| Intestine (Ger) | 50× | 0.5 | 2 | 2 | | | | |
| Cecum (Ger) | 50× | 0.6 | 1 | 1 | Strain 38 | + | ± | *Micromonospora* |
| Chicken: [Langshan; *Gallus Gallus*] | | | | | | | | |
| Intestine (Ger) | 50× | 0.8 | 1 | | | | | |
| Turkey: [Domestic; *Meleagris gallopavo*] | | | | | | | | |
| Cecum (Egy) | 50× | 1.1 | 3 | 2 | Strain 35 | + | + | *Bacillus* |
| Pigeon: [Common; *Columba livia*] | | | | | | | | |
| Feaces (Ger) | 50× | 1.5 | 5 | 4 | | | | |
| Cecum (Egy) | 50× | 1.0 | 2 | 1 | Strain 47 | + | ± | *Brevibacillus* |
| III. Fish flora Carp; *Cyprinus carpio* | | | | | | | | |
| Digestive tract (Ger) | 50× | 2.5 | 7 | 5 | Strain 52 | + | + | *Pseudomonas* |
| Roach; *Rutilus rutilus* | | | | | | | | |
| Digestive tract (Ger) | 50× | 0.8 | 2 | 2 | | | | |
| Tench; *Tinca tinca* | | | | | | | | |
| Digestive tract (Ger) | 50× | 1.2 | 3 | 3 | | | | |
| Telapia; *Telapia nilotica* | | | | | | | | |
| Digestive tract (Egy) | 50× | 2 | 3 | 2 | Strain 49 | + | + | *Bacillus* |

+; complete CGP degradation.
±; partial CGP degradation.

TABLE 2

Overview on the wide spread, habitats, and phylogeny of bacteria capable of extracellular CGP degradation, isolated previously and during this study.

| | Sample | Sample source | Number of isolates | Identified genera | Most investigated strain | Characterized enzymes |
|---|---|---|---|---|---|---|
| Aerobic Gram-negative bacteria[a] | Marine water, Pond sediment, Sewage sludge | Baltic sea, Germany, Germany | 11 | *Pseudomonas, Stryptomyces* | *P. Anguilliseptica* strain BI. | CphE$_{pa}$ |
| Aerobic Gram-positive bacteria[b] | Forest soil, River water | Germany, Germany | 43 | *Bacillus, Micromonospora* | *B. megaterium* strain BAC19 | CphE$_{Bm}$ |
| Strict anaerobic bacteria[c d] | Pond sediment, Marine water, Sewage sludge, Mudflats, Soil | Germany, Jordan, North sea, Baltic sea | 1 +27 mixed consortia | *Sedimentibacter* | *S. hongkongensis* strain KI | — |

TABLE 2-continued

Overview on the wide spread, habitats, and phylogeny of bacteria capable of extracellular CGP degradation, isolated previously and during this study.

| Sample | Sample source | Number of isolates | Identified genera | Most investigated strain | Characterized enzymes |
|---|---|---|---|---|---|
| Facoltative anaerobic bacteria[e] | Pond sediment | Germany | 1 | Pseudomonas | P. Alcaligenes strain DIP1 | — |
| Aerobic CGP and asparagines degrading bacteria[f] | Marine water River water Soil | Black sea, Turkey Germany, France, Caucasus | 242 | Flavobacterium, Pseudomonas, Comamonas, Photobacter, Oligella, Ochrobacter, Sphingomonas | Flavobacterium sp. | $CphE_{al}$ |
| CGP degrading bacteria from mammalian, avian and fish gut flora[g] | Gut flora | Germany, Egypt | 62 | Bacillus, Previbacillus, Micromonospora, Stryptomyces, Pseudomonas | 8 isolates; strains 15, 17, 31, 35, 38, 47, 49, 52 | — |

[a, b, c, d]Data from Obst, M. et al., J. Biol. Chem. 277: 25096-25105 (2002); Obst, M. et al., Biomacromolecules 5: 153-161 (2004); Obst, M. et al., Appl. Environ. Microbiol. 71: 3642-3652 (2005) and Krug 2001, respectively.
[e]Data from Sallam, A. et al., Submitted for publication (2008).
[f]Data from Zine, S., Diplom thesis, Institut für Molekulare Mikrobiologie und Biotechnologie, Westfälische Wilhelms-Universität, Münster, Germany (2004).
[g]This study.

TABLE 3

Effect of several group-specific inhibitors on the purified $CphE_{al}$ from P. alcaligenes strain DIP1.

| | | | HPLC analysis (Inhibition %[b]) | |
|---|---|---|---|---|
| Inhibitor specificity | Inhibitor | Concentration (mM) (low-high) | low inhibitor concentration | high inhibitor concentration |
| Thiol proteases | Leupeptin | 0.001-0.01 | 10 | 39 |
| Metalloproteases | EDTA | 30-60 | 65[c] | 75[c] |
| Serine proteases | Pefabloc ® | 8-80 | 91 | 100 |
| Serine proteases | PMSF | 1-10 | 0 | 57 |
| Tryptophan residues | NBS | 1-5 | 100 | 100 |
| | Control[a] | — | | 0 |

[a]Control without inhibitor,
[b]The percentage values of inhibition refer to the control, that is, activity of CGPase in the absence of an inhibitor,
[c]Values are not due to inhibition but due to formation of precipitates during OPA-derivatization prior to HPLC analysis.
PMSF: Phenylmethylsulfonylfluoride,
Pefabloc ®: 4-(2-aminoethyl) benzensulfonylfluoride•HCl,
NBS: N-bromosuccinimide.

TABLE 4

Comparison between the biochemical characteristics of $CphE_{al}$ from P. alcaligenes strain DIP1 and previously characterized CGPases.

| | Enzyme properties | | | | | | |
|---|---|---|---|---|---|---|---|
| Bacterium (Enzyme) | Localization | Molecular size (kDa) | Optimum temperature | Optimum pH range | CGP degradation products | Mechanism | Inhibitors |
| Synechocystis sp. PCC 6803 (CphB)[a] | Intra-cellular | 28 | 35° C. | 7-8 | β-Asp-Arg | Exo-peptidase | Pefabloc ®, PMSF, 3,4-dichloro-isocoumarin |
| P. anguilliseptica strain BI $(CphE_{Pa})$[b] | Extra-cellular | 43 | n.d. | 8-8.5 | β-Asp-Arg | Exo-peptidase | Pefabloc ®, PMSF, NBS |
| B. megaterium strain BAC19 $(CphE_{Bm})$[c] | Extra-cellular | 37 | 30-42° C. | 8-8.5 | β-Asp-Arg + (β-Asp-Arg)$_2$ | n.d. | Pefabloc ®, PMSF, NBS |

TABLE 4-continued

Comparison between the biochemical characteristics of CphE$_{al}$ from
P. alcaligenes strain DIP1 and previously characterized CGPases.

| Bacterium (Enzyme) | Localization | Molecular size (kDa) | Optimum temperature | Optimum pH range | CGP degradation products | Mechanism | Inhibitors |
|---|---|---|---|---|---|---|---|
| P. alcaligenes strain DIP1 (CphE$_{al}$)[d] | Extra-cellular | 45 | 50° C. | 7-8.5 | β-Asp-Arg | n.d. | Pefabloc ®, PMSF, NBS |

[a] Data from Richter, R. et al., Eur. J. Biochem. 263: 163-169 (1999),
[b] Data from Obst, M. et al., J. Biol. Chem. 277: 25096-25105 (2002),
[c] Data from Obst, M. et al., Biomacromolecules 5: 153-161 (2004),
[d] This study.
PMSF: Phenylmethylsulfonylfluoride, Pefabloc ®: 4-(2-aminoethyl) benzensulfonylfluoride•HCl, NBS: N-bromosuccinimide, n.d.: not determined.

The invention claimed is:

1. A process for the enzymatic production of a β-dipeptide composition from a preparation of a cyanophycin (CGP) or CGP-like polymer, said process comprising contacting the preparation of the CGP or CGP-like polymer with an CGPase from *P. alcaligenes* having a molecular weight of about 45 kDa, an optimum temperature of about 50° C. and an optimum pH range of 7 to 8.5 for enzymatic activity and having the ability to degrade CGP or CGP-like polymer into β-Asp-Arg, thereby degrading the CGP or CGP-like polymer into β-dipeptides.

2. The process of claim 1, wherein the CGPase is a CGPase from *P. alcaligenes* strain DIP1.

3. The process of claim 1, wherein the CGPase is the *P. alcaligenes* DIP1 CGPase CphE$_{al}$ having been deposited with the DSMZ as DSM 21533.

4. The process of claim 1, wherein:
(i) the β-dipeptide composition is composed of β-Asp-Arg dipeptide or of a mixture of β-dipeptides; and/or
(ii) the β-dipeptide composition is composed of β-dipeptides comprising the amino acid residues present in the CGP-like polymer.

5. The process of claim 4, wherein the β-dipeptides/β-dipeptide units are selected from β-aspartate-arginine and β-aspartate-lysine.

6. The process of claim 1, which further comprises preparing the CGP or CGP-like polymer preparation by culturing a prokaryotic or eukaryotic producing cell line producing CGP or CGP-like polymer.

7. The process of claim 6, wherein the CGP or CGP-like polymer producing cell line is selected from *Escherichia coli, Ralstonia eutropha, Acinetobacter baylyi, Corynebacterium glutamicum, Pseudomonas putida*, yeast strains, and plant biomass.

8. The process of claim 7, wherein the CGP or CGP-like polymer producing cell line is *Ralstonia eutropha* H16-PHB 4-Δeda (pBBR1MCS-2::cphA$_{6308}$/edaH16) or *E. coli* DH1 (pMa/c5-914::cphA$_{PCC6803}$).

9. The process of claim 6, wherein the CGP or CGP-like polymer preparation obtained by cultivating the CGP or CGP-like polymer producing cell line is isolated, purified and/or chemically modified.

10. The process of claim 6, wherein the CGP or CGP-like polymer preparation obtained by cultivating the CGP or CGP-like polymer producing cell line is not isolated or purified prior to being subjected to degradation with the CGPase.

11. The process of claim 1, which further comprises purifying or separating the degradation product.

12. The process of claim 1, which further comprises chemically modifying the degradation product.

* * * * *

UNITED STATES PATENT AND TRADEMARK OFFICE
CERTIFICATE OF CORRECTION

PATENT NO. : 8,980,845 B2
APPLICATION NO. : 12/995762
DATED : March 17, 2015
INVENTOR(S) : Sallam et al.

Page 1 of 1

It is certified that error appears in the above-identified patent and that said Letters Patent is hereby corrected as shown below:

In the specification

Column 1, line 27, "Cyanophycin Granule Polypeptide" -- should read -- <u>C</u>yanophycin <u>G</u>ranule <u>P</u>olypeptide --.

Column 5, line 3, "Raistonia eutropha" -- should read -- Ralstonia eutropha --.

Column 9, line 50, "Raistonia eutropha" -- should read -- Ralstonia eutropha --.

Column 9, line 53, "Raistonia eutropha" -- should read -- Ralstonia eutropha --.

Column 25, line 11, "2 g citrate" -- should read -- 2 g $l^{-1}$ citrate --.

Column 27, line 29, "per I" -- should read -- per 1 --.

Column 27, line 50, "per I tap water" -- should read -- per 1 tap water --.

Column 40, line 45, "6 g citrate" -- should read -- 6 g $l^{-1}$ citrate --.

Signed and Sealed this
Twenty-fourth Day of November, 2015

Michelle K. Lee
*Director of the United States Patent and Trademark Office*

SEQUENCE LISTING

<160> NUMBER OF SEQ ID NOS: 10

<210> SEQ ID NO 1
<211> LENGTH: 19
<212> TYPE: DNA
<213> ORGANISM: Artificial
<220> FEATURE:
<223> OTHER INFORMATION: primer 27f

<400> SEQUENCE: 1
gagtttgatc ctggctcag                                              19

<210> SEQ ID NO 2
<211> LENGTH: 15
<212> TYPE: DNA
<213> ORGANISM: Artificial
<220> FEATURE:
<223> OTHER INFORMATION: primer 343r

<400> SEQUENCE: 2
ctgctgcctc ccgta                                                  15

<210> SEQ ID NO 3
<211> LENGTH: 15
<212> TYPE: DNA
<213> ORGANISM: Artificial
<220> FEATURE:
<223> OTHER INFORMATION: primer 357f

<400> SEQUENCE: 3
tacgggaggc agcag                                                  15

<210> SEQ ID NO 4
<211> LENGTH: 18
<212> TYPE: DNA
<213> ORGANISM: Artificial
<220> FEATURE:
<223> OTHER INFORMATION: primer 519r
<220> FEATURE:
<221> NAME/KEY: misc_feature
<222> LOCATION: (2)..(2)
<223> OTHER INFORMATION: n = T or A
<220> FEATURE:
<221> NAME/KEY: misc_feature
<222> LOCATION: (14)..(14)
<223> OTHER INFORMATION: n = T or G

<400> SEQUENCE: 4

```
gnattaccgc ggcngctg                                                 18

<210> SEQ ID NO 5
<211> LENGTH: 18
<212> TYPE: DNA
<213> ORGANISM: Artificial
<220> FEATURE:
<223> OTHER INFORMATION: primer 536f
<220> FEATURE:
<221> NAME/KEY: misc_feature
<222> LOCATION: (5)..(5)
<223> OTHER INFORMATION: n = C or A
<220> FEATURE:
<221> NAME/KEY: misc_feature
<222> LOCATION: (17)..(17)
<223> OTHER INFORMATION: n = T or A

<400> SEQUENCE: 5
cagcngccgc ggtaatnc                                                 18

<210> SEQ ID NO 6
<211> LENGTH: 17
<212> TYPE: DNA
<213> ORGANISM: Artificial
<220> FEATURE:
<223> OTHER INFORMATION: primer 803f

<400> SEQUENCE: 6
attagatacc ctggtag                                                  17

<210> SEQ ID NO 7
<211> LENGTH: 20
<212> TYPE: DNA
<213> ORGANISM: Artificial
<220> FEATURE:
<223> OTHER INFORMATION: primer 907r

<400> SEQUENCE: 7
ccgtcaattc atttgagttt                                               20

<210> SEQ ID NO 8
<211> LENGTH: 16
<212> TYPE: DNA
<213> ORGANISM: Artificial
<220> FEATURE:
<223> OTHER INFORMATION: primer 1114f

<400> SEQUENCE: 8
gcaacgagcg caaccc                                                   16

<210> SEQ ID NO 9
<211> LENGTH: 17
<212> TYPE: DNA
<213> ORGANISM: Artificial
<220> FEATURE:
<223> OTHER INFORMATION: primer 1385r
<220> FEATURE:
<221> NAME/KEY: misc_feature
<222> LOCATION: (9)..(9)
<223> OTHER INFORMATION: n = A or G

<400> SEQUENCE: 9
cggtgtgtnc aaggccc                                                  17

<210> SEQ ID NO 10
<211> LENGTH: 20
<212> TYPE: DNA
<213> ORGANISM: Artificial
```

-continued

```
<220> FEATURE:
<223> OTHER INFORMATION: primer 1525r

<400> SEQUENCE: 10
agaaaggagg tgatccagcc                                              20
```